United States Patent
Gretton et al.

(10) Patent No.: US 12,201,158 B2
(45) Date of Patent: Jan. 21, 2025

(54) ELECTRONIC VAPING SYSTEM

(71) Applicant: AYR LTD., London (GB)

(72) Inventors: Mark Gretton, London (GB); Ian Murison, London (GB)

(73) Assignee: AYR LTD., London (GB)

(*) Notice: Subject to any disclaimer, the term of this patent is extended or adjusted under 35 U.S.C. 154(b) by 841 days.

(21) Appl. No.: 17/284,695

(22) PCT Filed: Oct. 14, 2019

(86) PCT No.: PCT/GB2019/052922
§ 371 (c)(1),
(2) Date: Apr. 12, 2021

(87) PCT Pub. No.: WO2020/074929
PCT Pub. Date: Apr. 16, 2020

(65) Prior Publication Data
US 2021/0337878 A1    Nov. 4, 2021

(30) Foreign Application Priority Data

| Oct. 12, 2018 | (GB) | 1816618 |
| Nov. 5, 2018 | (GB) | 1818020 |
| Feb. 26, 2019 | (GB) | 1902548 |

(51) Int. Cl.
*A24F 40/51*    (2020.01)
*A24F 15/015*   (2020.01)
(Continued)

(52) U.S. Cl.
CPC .......... *A24F 40/51* (2020.01); *A24F 15/015* (2020.01); *A24F 40/10* (2020.01); *A24F 40/42* (2020.01);
(Continued)

(58) Field of Classification Search
CPC .......... A24F 40/51; A24F 40/53; A24F 40/65; A24F 40/48; A24F 40/10; A24F 40/46;
(Continued)

(56) References Cited

U.S. PATENT DOCUMENTS 10,136,676 B2 * 11/2018 Newns ................ H05B 1/0244
2015/0083147 A1    3/2015 Schiff et al.
(Continued)

FOREIGN PATENT DOCUMENTS

| CN | 106579566 A | * | 4/2017 | ............ A24F 40/48 |
| CN | 107949286 A | * | 4/2018 | ........... A24B 15/167 |

(Continued)

OTHER PUBLICATIONS

CN106579566A-English Translation (Year: 2017).*
(Continued)

*Primary Examiner* — Timothy L Maust
*Assistant Examiner* — Christopher M Afful
(74) *Attorney, Agent, or Firm* — Saul Ewing LLP

(57) ABSTRACT

A re-fillable liquid tip or pod for a vaping device that includes capacitive sensor plates in the tip liquid reservoir. A liquid re-filling device provides liquid to the vaping device, drawn from a refill bottle; the re-filling device includes a capacitance measuring circuit; a microcontroller uses the data from the capacitance measuring circuit to determine if the level of liquid in the tip liquid reservoir is above or below a threshold level; if below, then a liquid pump in the re-filling device is activated to draw liquid from the refill bottle and pump it through the vaping device and up into the tip liquid reservoir. Pumping ceases once the liquid reaches the threshold level.

45 Claims, 35 Drawing Sheets

(51) Int. Cl.
*A24F 40/10* (2020.01)
*A24F 40/42* (2020.01)
*A24F 40/44* (2020.01)
*A24F 40/46* (2020.01)
*A24F 40/48* (2020.01)
*A24F 40/53* (2020.01)
*A24F 40/57* (2020.01)
*A24F 40/60* (2020.01)
*A24F 40/65* (2020.01)
*A24F 40/95* (2020.01)
*A61M 15/06* (2006.01)
*G01F 23/26* (2022.01)

(52) U.S. Cl.
CPC .............. *A24F 40/44* (2020.01); *A24F 40/46* (2020.01); *A24F 40/48* (2020.01); *A24F 40/53* (2020.01); *A24F 40/57* (2020.01); *A24F 40/60* (2020.01); *A24F 40/65* (2020.01); *A24F 40/95* (2020.01); *G01F 23/26* (2013.01); *A61M 15/06* (2013.01)

(58) Field of Classification Search
CPC .......... A24F 40/95; A24F 40/44; A24F 40/57; A24F 40/42; A24F 15/015; A24F 40/60; G01F 23/26
See application file for complete search history.

(56) References Cited

U.S. PATENT DOCUMENTS

| | | | |
|---|---|---|---|
| 2015/0245668 A1* | 9/2015 | Memari | A24F 40/90 |
| | | | 206/250 |
| 2016/0150824 A1 | 6/2016 | Memari et al. | |
| 2017/0347709 A1* | 12/2017 | Laakso | A24F 40/42 |
| 2018/0279688 A1* | 10/2018 | Qiu | A24F 40/48 |
| 2018/0296777 A1* | 10/2018 | Terry | A61M 11/042 |
| 2019/0099567 A1* | 4/2019 | Nettenstrom | A24F 40/40 |
| 2023/0209662 A1* | 6/2023 | Reevell | H05B 1/0244 |
| | | | 392/404 |

FOREIGN PATENT DOCUMENTS

| | | | | |
|---|---|---|---|---|
| EP | 3027072 A1 | | 6/2016 | |
| RU | 2654619 C1 | * | 5/2018 | .......... A24B 15/167 |
| WO | WO-2017045897 A1 | * | 3/2017 | .......... A24B 15/167 |
| WO | WO-2017163044 A1 | * | 9/2017 | ............ A24F 40/10 |

OTHER PUBLICATIONS

CN107949286A-English Translation (Year: 2018).*
RU2654619C1-English Translation (Year: 2018).*
International Search Report, dated Jan. 16, 2020, issued in International Application No. PCT/GB2019/0052922.

* cited by examiner

ELECTRONIC VAPING SYSTEM

CROSS REFERENCE TO RELATED APPLICATIONS

This application claims the priority of PCT/GB2019/052922, filed on Oct. 14, 2019, which claims priority to GB Application No. GB 1816618.1, filed on Oct. 12, 2018; GB Application No. GB 1818020.8, filed on Nov. 5, 2018; and GB Application No. GB 1902548.5, filed on Feb. 26, 2019, the entire contents of each of which being fully incorporated herein by reference.

BACKGROUND OF THE INVENTION

1. Field of the Invention

The field of the invention relates to an electronic vaping system. Vaping systems provide an inhalable aerosol which may contain nicotine or other substances; they are typically used as alternatives to combustible cigarettes.

2. Description of the Prior Art

Vaping devices come in various form factors; the simplest use small pods that attach to a slim body, which contains a battery and simple control electronics. The pod is pre-filled at a factory with a liquid, often called an e-liquid, and includes both a small (typically 0.7 mL to 1.3 mL) reservoir of this liquid, a small wick and a heating element wound around the wick; when the user inhales, a small pressure switch is activated, which in turn cause current to heat the coil and generate an aerosol which is inhaled. Pods might have the equivalent to 10 or 20 cigarettes worth of nicotine, and habitual vapers can use 1 or 2 pods a day. Pods are not recyclable and there is growing concern about the tens of millions of these pods that are currently being discarded in landfill.

Some designs of vaping device are re-fillable and hence do not use these small pre-filled pods. Instead, a user opens a small bottle of the e-liquid, unscrews their vaping device to expose an internal liquid reservoir, and drips or squeezes its contents into the reservoir; this can be somewhat messy and inconvenient however. The overall user interaction with conventional re-fillable e-cigarettes (covering all aspects of how the user controls, re-fills, re-charges and generally interacts with the device) can therefore be complex and this is reflected in their design, which is often rather technical, with various control buttons. The overall user interaction is rarely intuitively clear. This is very different from the straightforward and simple (and, to smokers, deeply attractive) ritual of opening a pack of conventional cigarettes and lighting up. The complex user interaction that characterizes conventional refillable e-cigarettes has none of the simplicity or attractive ritual of opening a packet of cigarettes and lighting up.

Designing a vaping system that replicates the simplicity of a conventional cigarette is a considerable challenge but is key to the mass-market adoption of e-cigarettes by smokers, and is hence key to delivering on their considerable public health potential.

This disclosure builds on the disclosures in the following patent publications, the contents of which are incorporated by reference to the maximum extent permissible: U.S. Pat. Nos. 9,247,773, 10,131,532, 10,149,497, and U.S. Ser. No. 10/285,449.

SUMMARY OF THE INVENTION

The invention is a vaping system including:
(a) an automatically re-fillable liquid reservoir that provides liquid to an atomizer;
(b) a liquid level sensing sub-system that directly or indirectly measures, infers or detects the amount of the liquid, or the level of liquid, in the liquid reservoir, by measuring electrical characteristics of the liquid reservoir that vary depending on the amount or level of liquid in the liquid reservoir; and
(c) a fluid transfer system configured to automatically transfer liquid to the liquid reservoir under the control of the liquid level sensing sub-system.

BRIEF DESCRIPTION OF THE FIGURES

The invention will be described with reference to the following figures, which show features and aspects of the AYR vaping system.

FIG. 20 is a cross-sectional view of the refill liquid bottle with the child-proof cap on.

DETAILED DESCRIPTION

We will describe an implementation of the invention called the AYR™ vaping system. The AYR vaping device includes a number of features which aid manufacturability, recyclability usability or performance. We organise these features into the following four main areas:

A. Mechanical or constructional features
B. Software/electronics features
C. Data and connectivity features
D. Liquid handling and re-filling features A preliminary note on terminology: whilst the primary use case we describe is for an e-liquid vaping device which provides an inhalable nicotine mist or aerosol, some features are applicable more broadly, including for example to vaping devices that do not use liquids but instead heat tobacco but do not burn it; the term 'vaping', 'vaping device' and 'vaporising device', 'personal vaporising device' and TV' should therefore be expansively construed to include e-cigarette type devices of all form factors (including closed pods, or open tanks, or any other system), heat-not-burn type vaping devices, hybrid devices that combine both heat-not-burn with liquid atomisation, and also devices enabling not just nicotine to be inhaled but also other substances, such as CBD and THC, whether for medicinal or recreational purposes.

A 'vaping' or 'vaporising' device may therefore be used to deliver any atomisable liquid; the term 'liquid' and 'e-liquid' should be broadly construed to cover any atomisable liquid, gel or other substance, including nicotine and nicotine salts of varying strengths, liquids with zero nicotine, liquids with CBD, liquids with THC, liquids with medicines, liquids with any botanical or synthetic flavouring or constituents. The term 'atomiser' should be broadly construed to cover any device that can create an atomisation, aerosol, mist or fine droplets for the purpose of inhalation; an atomiser may include a heated element (e.g. a wire coil wound around a wick, or planar heating element formed on a wick, a micro-engineered steel blade or indeed any other system that generate atomisation, aerosol, mist or fine droplets, such as a piezo-electric cold mist generator). A vaping device may be also be a consumer device or a medically approved device.

One specific implementation we will describe, known as the AYR™ system, uses a heated coil mounted within a ceramic wick that transports nicotine bearing e-liquid from a reservoir to the heated coil. The scope of the invention is not however limited to that specific implementation.

A. Mechanical or Constructional Features

AYR Vaping System Overview

Figure 1:
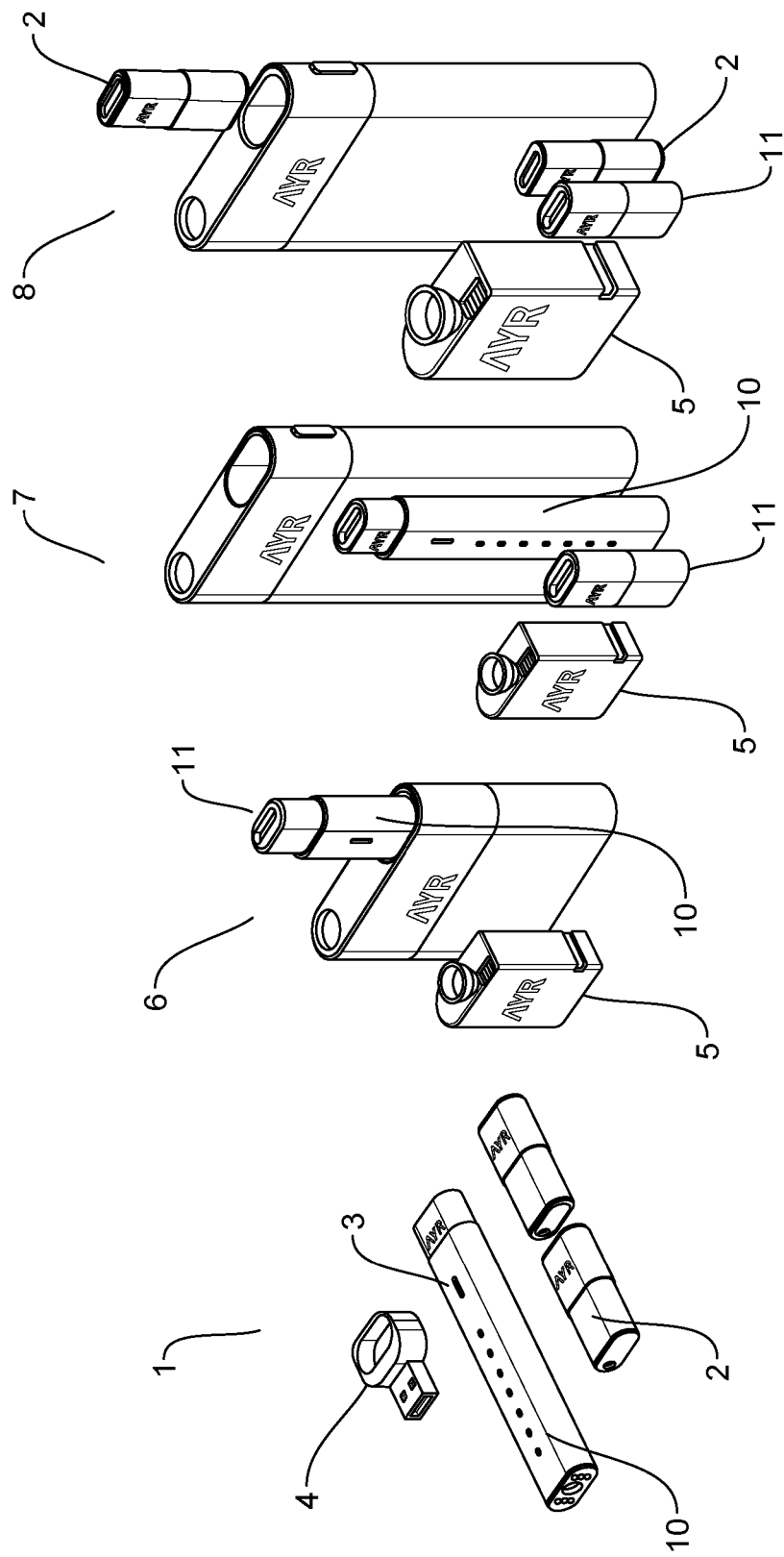
FIG. 1 shows the range of four different vaping devices in the AYR vaping system.

The AYR vaping system is a flexible vaping platform that encompasses four main variants: AYRVape™, AYRBase™, AYRCase™, and AYRMod™. All variants use the same underlying software and hardware, leading to economies in development and manufacturing. We will describe each in turn, at a high level. FIG. 1 shows each of these four variants; running from left to right, we have AYRVape, indicated generally at 1, which has the form-factor of a conventional pod-type pre-filled vaping device, such as a Vype ePod™. This can be used as a stand-alone vaping system, using pre-filled, single use disposable e-liquid pods 2 that are not user refillable. A pod 2 slides into the top of the vaping device body 10; pods 2 are colour coded on their bottom half, with different colours representing different flavours. Pods 2 include an authentication chip that is read by a microprocessor in the device body 10; the authentication chip prevents counterfeits being useable, and also prevents illicit re-filling (e.g. with illegal liquids that have not gone through appropriate safety testing). The authentication chip also stores a complete record of capsule filing date, liquid batch number, and excise duty or tax payment.

Because these pods contain a relatively small quantity of liquid (e.g. 1.5 mL) they have to be replaced perhaps daily for a regular user; this has a significant environmental impact because these pods are not recyclable; it can be frustrating too for users that run out of pods, and they are then more likely to relapse into smoking cigarettes. AYRBase, indicated generally at 6, addresses these problems; it is a desktop docking station that the user slots their vaping device 10 into; but instead of a pod 2 which has been factory filled with liquid, the user slides a special re-fillable pod 11 onto the vaping device body instead; the vaping device body 10 is hence compatible with both pre-filled pods and also re-fillable pods 11. Re-fillable pod 11 includes elements of a liquid level sensing system; a pair of sensor plates in the liquid reservoir, running substantially over half-way up the height of that liquid reservoir. The sensor plates are used to measure capacitance; the capacitance increases as the liquid level in the reservoir rises. A capacitance measuring circuit (typically in the re-filling dock 6) controls the liquid pump: if the capacitance is below a threshold when the vaping device is placed in the dock 6 and a liquid level measurement takes place, then the pump is activated, pumping fresh liquid into the re-fillable pod 11 until the threshold is reached. The pre-filled pods 2 (i.e. factory pre-filled) do not include any sensor plates.

The dock 6 hence automatically fills the specially designed re-fillable pod 11 fitted to the vaping device body 10 with fresh e-liquid. The re-fillable pod 11 has the same external dimensions as the single-use non-refillable pods 2, but is a single colour. The e-liquid comes from a 10 mL liquid refill bottle 5 that is slotted into the base of the dock 6 and connects to a fluid transfer system in the dock 6. Liquid refill bottle 5 is fully re-cyclable and also includes an anti-counterfeit or authentication component so that only authorised bottles are recognised and useable by the dock (or case or vaping device) and user re-filling of the bottles leads to a bottle from which liquid cannot be pumped, making re-filling pointless. Whilst 10 mL is the maximum capacity permitted in the EU, in other markets, much larger bottles could lawfully be used, which may appeal to the cost-conscious consumer. Vaping device 1 is hence a hybrid; it can operate like a conventional vaping device with pre-filled pods, but also as a re-fillable vaping device.

Typically, a user will keep the dock 6 at home or at their office desk; the vaping device 10 and re-fillable pod 11 is re-filled with the user's desired e-liquid flavour in under 10 seconds; when it is withdrawn from the desktop dock, it is in effect a fresh, filled vaping device, without the need to dispose of the pod each time it is re-filled.

Some users will prefer not to have a desktop liquid re-fill and power re-charge dock, but instead include all that functionality in a portable case: this is AYRCase, indicated generally at 7. The portable case stores, and automatically re-charges and re-fills the vaping device 10 and refillable pod or tip 11. It includes a large re-chargeable battery; the re-fill bottle 5 is inserted into the base of the case 7, where it engages with a fluid transfer system in the case.

The final AYR variant is AYRMod, indicated generally at 8: this is a one-piece vaping device with a large battery of at least 2000 mAh for high power vaping; the same refill bottle 5 is now inserted directly into the vaping device 8; the AYRMod vaping device 8 also works with the same re-fillable tip 11 as is used across the AYR range, as well as the same pre-filled tips 2 that also work across the range.

Because the re-fillable tip 11 does not have to be discarded after its liquid has been used up, but can be re-filled and re-used multiple times (typically 10-20 times) it can include more sophisticated and costly atomising technology (such as the wick-less and coil-less Distiller Plate™ or PureTech™ stainless steel blade atomiser from BAT) than a conventional single use disposable pod, leading to better and safer aerosol production. Further details on this blade atomiser technology can be found at WO2018211252 WO2018224823, the contents of which are incorporated by reference to the maximum extent permissible.

The Ayr system uses a closed loop temperature control system which keeps the heating coil to the desired temperature range to ensure the safe and predictable generation of chemicals in the resultant aerosol, for example, avoiding the creation of formaldehydes in the aerosol, or the creation of THC from CBD liquids, both of which can happen if the coil temperature is too high. For nicotine e-liquid with a 50:50 PV/VG mix, this is 280 Celcius, plus or minus 20 Celcius. Accurate temperature control of the heating element has also been found to very significantly increase its lifetime, minimising environmental impact of these items. Accurate temperature control of the atomising element, taken together with using a liquid re-fill bottle, has been found to synergistically minimise the environmental impact of the overall AYR system since the pods last much longer before requiring replacement and the re-fill bottles are themselves recyclable.

We will look more closely now at each variant.
AYRVape Overview

In AYRVape, the AYR vaping device body 10 takes pre-filled, e-liquid pods 2. The pods 2 are 'closed', meaning that each pod is sealed after authorized filling with e-liquid and cannot then be re-filled by the end-user: this ensures compliance with safety regulations (such as the European Tobacco Products Regulation 2014/40/EU) and ensures that only the highest quality e-liquid from an authorized source is present in the cartridge.

Different flavours of pods use different colours on their bottom half; this is the portion that is fully inserted into the vaping device body; a small cut-out 3 in the main vaping device body 10 shows the colour, so the user can see at a glance the flavour being used. The vaping device body 10 includes a USB charger port and can be recharged from a conventional USB charger dock or platform 4.

The internal engineering of the vaporiser or vaping device body 1 differs from a conventional body however because it includes features that enable it to work with a re-fillable tip or pod and not only a conventional pre-filled closed pod (i.e. one that is filled by a manufacturer and sold to the consumer pre-filled and also not meant to be re-filled). It has a fluid ingest nozzle or aperture and valve to which an external source of e-liquid can be connected; in the AYR system, this is a 10 mL e-liquid refill bottle 5. The fluid ingest nozzle or aperture connects via a liquid tube or path; the tube or path carries liquid, (pumped from an external electric pump for the AYRBase 6 and AYRCase 7 variants; pumped from an internal pump for the AYRMod variant 8) to the refillable atomising pod 11 that sits at the top of the body 10; the body includes circuitry that detects the liquid level in the re-fillable tip or pod so that automatic re-filling can start and stop correctly; it also includes temperature regulation circuitry so that the atomiser heats the liquid to the correct temperature; and it also includes the same anti-counterfeit or authentication components as the pre-filled pods 2, so that only authorised pods 11 can be used with the system.

The vaping device 10 may track a wide variety of performance and other data. It may send this data, via physical contacts, to the desktop dock 6 or portable re-fill and re-charge case 7. That dock 6 or case 7 may then include integrated Wi-Fi or 3G/4G/5G connectivity to a web server providing age verification services and data analytics, or may couple or dock with an accessory that provides that connectivity. Alternatively, vaping device 10 may itself include short range wireless connectivity (e.g. Bluetooth or Wi-Fi or UWB) to the user's smartphone, smartwatch, tablet etc or other device (the term 'smartphone' will be used generically to cover any sort of connected device) and use the connectivity capabilities of that smartphone to connect to a remote server; direct connectivity from the vaping device 10 or 8 to the smartphone and then to the web (e.g. via Web Bluetooth and a smartphone browser that both supports Web Bluetooth and runs on iOS and Android, or UWB, or any other suitable system) may also be implemented.

Connectivity to a web server based age verification system enables that server to send an unlock signal (directly or indirectly) to the vaping device 10 directly or via whatever intermediary device or devices are in place, to enable normal vaping use only if that user passes the age requirements of the age verification system. The vaping device 10 also captures a broad range of device and usage information, which may be particularly relevant where the device is used as part of a clinical trial, or where the user is interested in monitoring usage, for example as an aid to a smoking or nicotine cessation program.

AYRBase Overview

As noted above, a pre-filled, non-re-fillable pod 2 can be replaced with a re-fillable pod or tip 11. This takes us to the AYRBase 6 variant; the same AYRVape vaporiser body 10 can be placed in a desktop docking station or base 6; a small (e.g. 10 mL) liquid refill bottle 5 is inserted into the docking station 6 and a small electric micro-pump (e.g. a peristaltic or piezo pump or other low-cost pump) in the docking station then automatically withdraws liquid from the refill bottle 5 and pumps it into the body of the vaping device 10; if then flows up through the body via a liquid path and into the refillable tip 11.

The refillable pod or tip 11 includes a liquid level sensing sub-system (e.g. capacitive sensing plates inside the liquid reservoir in the pod 11 that is being gradually filled with liquid during refilling) which enable the changing capacitance of the reservoir to be measured by capacitive sensing circuitry, which in turn automatically turns the electric micro-pump on when the sensed level of liquid in the tip reservoir is below a defined amount, and off when the level of liquid in the tip reservoir reaches that defined amount and hence sufficient liquid is present in the re-fillable tip reservoir. Once re-filling stops, the vaping device is ready for use.

For AYRBase 6, the dock 6 includes a power charging system to re-charge the rechargeable battery in the vaping device body 10; a typical user might dock the vaping device body 10 into the dock 6; the body 10 then re-fills (which takes under 10 seconds for a complete re-fill of typically 1 mL) from the liquid refill bottle 5 and continues to re-charge the battery in the vaping device; body 10 many users like to dock the vaping device 10, 11 at night, just as they dock or connect their smartphones to a charger. In the morning, the vaping device 10, 11 is ready to use, with a fully re-charged battery and a full liquid reservoir, just like a fresh vaping device.

The AYR refill bottle 5 removes the cost and waste of disposing of conventional, single-use non re-fillable pre-filled pods; these conventional, non re-fillable pre-filled pods are virtually impossible to recycle since they include not only a plastic casing, but a fine wire heating coil and a ceramic wick. AYR refill bottles 5 are however fully recyclable. Further, whilst in the EU, they are limited to 10 mL capacity, in other markets those limits may not apply; hence a 50 mL or 100 mL+ bottle could be used, providing very economical liquid from a fully recyclable source.

A re-fillable AYR pod or tip 11, which uses a conventional heating wire wound around a ceramic core, will itself need to be replaced, typically after 30 mL of liquid has passed through it, since residues build up over time and affect vaping performance. Since a conventional pre-filled tip contains 0.7-1.5 mL of liquid, the AYR refillable tip is being used for 20-40 times as long as a non-re-fillable tip or pod in a conventional system.

Combining a large refill bottle with a very long-lasting atomiser enables economical and environmentally friendly vaping. AYR is hence considerably more environmentally friendly than conventional cartomiser type pod-based vaping devices, such as Juul™ pods. A re-fillable AYR tip using more advanced atomising technology designed for greater longevity, such as a micro-engineered stainless steel blade, e.g. the Distiller Plate™ system from British American Tobacco plc, may need replacing even less frequently, and is hence potentially even more environmentally friendly.

AYRBase 6 includes Wi-Fi connectivity to the user's smartphone; the smartphone can then communicate with a remote server. A small icon, appearing to be an application icon (but not in fact being an application, i.e. something available from the Apple AppStore or Android Play Store or other digital distribution centre) appears on the user's smartphone screen alongside app icons; selecting this small icon then autoruns a routine that loads a specific URL into the smartphone's web browser; this is the URL of a remote server that provides age verification services and can also ingest and analyse usage data from the device.

AYRCase Overview

The same vaping device body 10 with a re-fillable tip 11 can be used not only in the AYRBase 6 docking station, but also in the AYRCase 7 portable case, shown third from the left in FIG. 1. AYRCase 7 includes the same micro-pump as AYRBase 6, and takes the same 10 mL liquid refill bottle. It is however a fully portable solution, enabling the user to take the AYR vaping device 10, 11 away for several days at a time, fully protected in the case 7, and available to be automatically recharged with power and re-filled with atomisable liquid whenever the vaping device 10, 11 is inserted back into the case 7. The vaping device 10, 11 is also still fully compatible with pre-filled pods 2; a user can hence try different flavours of pre-filled pods and then purchase the more costly 10 mL refill bottle 5 once a favourite flavour or flavours has been settled on.

AYRMod Overview

The final variant is a one-piece vaping device with a large battery, typically of at least 2000 mAh called AYRMod 8; smaller or larger batteries are also possible. The same refill bottle 5 is now inserted directly into the vaping device 8; the vaping device 8 also works with the same re-fillable tip 11 as is used across the AYR range. The main difference is that the battery performance is greater, and it hence appeals to users who like the more high-powered 'mod' type vaping device and experience. The AYRMod 8 vaping device is also fully compatible with pre-filled pods 2; a user can hence try different flavours of pre-filled pods and then purchase the more costly 10 mL (or other capacity) refill bottle 5 once a favourite flavour or flavours has been settled on. In some markets, as noted above, regulation permits refill bottles larger than 10 mL and in the markets, AYRMod 8 could use 20 mL or larger refill bottles.

In the table below, we summarise some key AYR features which are absent from a conventional pod-type vaping system.

| AYR System Feature | Conventional Pod System |
| --- | --- |
| Hybrid platform that supports pre-filled pods and also re-fillable pods. | No—restricted just to pre-filled pods. |
| Sophisticated, high performance atomising technology can be used. | No—inherently restricted to low cost disposable atomisers with attendant contamination risks. |
| Key consumable is an ultra low cost, fully re-cyclable closed liquid re-fill bottle or capsule designed for fully automated mass manufacture. | No—the consumable, the pod, is far more complex as it includes an atomiser and is not recyclable. |
| Long shelf life for closed liquid re-fill bottle or capsules, for maximum distributor, retailer and consumer store appeal. | No—shelf life is inherently limited by nicotine/atomiser contamination. |
| Pre-filled pods and 10 mL re-fill bottles all include an authentication chip for counterfeit protection, and to stop user-filling. | No—authentication chip is absent; counterfeits increasingly common and the danger of illicit liquids is becoming apparent. |
| Modular design supports a family of different products, appealing to different users and channels, and enabling fast product iteration, fast response to test results and to changing market conditions and consumer needs, and all | No—just a single product. |

-continued

| AYR System Feature | Conventional Pod System |
|---|---|
| with the possibility of substantial equivalence under PTMA. | |
| Collects and shares rich data enabling powerful behavioural insights and e-fulfilment—driving consumer engagement and the future innovation pipeline. | No—data capture is wholly absent; no automatic e-fulfilment. |
| Vaping session length can be made equivalent to smoking a cigarette for an intuitive awareness of e-liquid consumption. | No—all day grazing common. |
| Single bottle or capsule design (e.g,. 5 ml-10 mL) can be used across a large family of devices, going right up to sub-ohm mods, for maximum distributor, retailer and consumer appeal, and enhanced cost reduction through maximum economies of scale. | No—pods are for just a single design of device. |
| Accurate closed-loop control of the atomiser temperature to ensure predictable vapour constituents and extended atomiser lifetime | No—atomiser temperature can vary widely. |

The table below lists the sorts of data (all of which is time stamped) that is collected by the AYR vaping system and, subject to user consent and applicable data protection laws, sent to a remote server for analysis.

| Data Captured by AYR |
|---|
| Vaping device handling status: unlocked |
| Vaping device handling status: locked |
| Vaping device handling status: inserted into case or dock |
| Vaping device handling status: removed from case or dock |
| Vaping device handling status: firmware version |
| Vaping device handling status: firmware updated |
| Vaping device operations status: puff started |
| Vaping device operations status: puff ended |
| Vaping device operations status: session started |
| Vaping device operations status: session ended |
| Vaping device operations status: refilled |
| Vaping device operations status: refill level reading |
| Heating status: atomiser temperature |
| Heating status: discrete mode enabled |
| Heating status: discrete mode disabled |
| Heating status: ambient temperature |
| Case or dock status: active |
| Case or dock status: standby |
| Case or dock status: set time/date |
| Case or dock status: state of charge |
| Case or dock status: charging |
| Case or dock status: error condition |
| Case or dock status: firmware version |
| Case or dock status: firmware updated |
| PV status: inserted |
| PV status: removed |
| PV status: refill started |
| PV status: refill stopped |
| PV status: fluid level |
| Bottle status: batch number |
| Bottle status: liquid or flavour type |
| Bottle status: nicotine strength |
| Bottle status: unique ID |
| Bottle status: non-tamperable count-down counter value |
| Bottle status: excise payment unique ID or code |

Because AYR is a data-centric, fully connected system, that enables valuable feedback and rich insights to be generated. These can be in real-time or near real-time where the vaping device is itself connected to a remote server (e.g. the vaping device can deliver real-time data since it either includes an integral wireless module, or can send data in real-time over Bluetooth to a smartphone, which can then send that data in real-time to the remote server). Alternatively, data may be downloaded from the vaping device to a portable or desktop docking station, for example in the evening when the vaping device is returned to the docking station for an overnight power re-charge, and data is then sent by the docking station; this may be just once or twice a day. Data of this accuracy and comprehensiveness is especially important to public health bodies and scientists looking to better understand how vaping devices are being used.

We summarise these in the table below:

| Data Captured by AYR | Insight |
|---|---|
| Flavour and strength of liquid being vaped. | Feedback to bottle filling factories and logistics to ensure that the most popular flavours are instore and on-line when needed. |
| Flavour and strength of new liquids being vaped in test launches. | Feedback to liquid and flavour development specialists—ensures fast, evidence-based creation and roll out of new flavours. |
| Geolocation (e.g. via a smartphone app where the vaping device is tethered or connected via a short range signal like Bluetooth or UW/B) of the flavour and strength of liquid being vaped. | Feedback to bottle filling factories and logistics to ensure that the most popular flavours are instore or on-line in the cities or regions where they are most needed. |
| Bottle e-liquid level. | App or SMS text can prompt user when to buy more—e.g. through e-fulfilment, and to provide special offers/coupons for use in vape stores or online. |
| Flavour and strength of liquid being vaped. | Feedback to consumers suggesting other flavours they might like. |
| Self-reporting (via app) on continuing cigarette smoking. | Feedback on impact on cigarette consumption. |
| Patterns or usage over time. | Correlation with advertising or marketing to determine effectiveness. |
| Patterns or usage over time. | Insight into product's enduring appeal. |
| Time of usage; time of each vaping session (grazing? more cigarette-like?); quantity of e-liquid consumed. | Insight into how consumers really use these products. |
| Self-reporting (via app) of age, sex and other demographic data. | Demographic insight into who is using the device, how and when. |
| Excise duty payment data | Insight and validation to tax collection authorities. |

We will now drill down into capturing the specific features in AYR which are not present in conventional vaping systems.

Vaping Device that Works with Both Pre-Filled and Re-Fillable Tips or Pods

In the preceding section, we described how AYR is a hybrid vaping device: it can use conventional pre-filled, closed pods 2 (sometimes called cartomisers); these slide, snap or fit onto the body 10 of the AYR vaping device 1; a magnetic latch may be used. But it can also use re-fillable pods 11, which again slide, snap or fit onto the body 10 of the AYR vaping device 1 in the conventional manner. The vaping device 10 can be inserted into a re-filling dock (such as a desktop docking station 6 for AYRBase or a portable case 7 for AYRCase) and a re-fill bottle 5 connected to a pump in the dock 6, 7 then automatically replenishes the liquid in the vaping device pod 11. Or the vaping device can itself include the pump and re-fill container 5, as in AYR-Mod. This platform approach increases component re-use across multiple devices, each serving different market sectors, reduces engineering development time because of the commonality of core aspects across all devices, and reduces regulatory costs and effort because the components relevant to regulatory approval are essentially shared.

We can summarise and generalise this feature as follows:
A handheld vaping device configured to work with;
(a) a non-user refillable combined atomizer and liquid reservoir (or 'pod') that is (i) attachable to, and removable from, a main body of the device and that is (ii) supplied to an end-user pre-filled with liquid; and to also work with:
(b) a user refillable combined atomizer and liquid reservoir (or 'pod') that is (i) attachable to, and removable from, the main body of the device and that is (ii) configured to be automatically fillable with liquid multiple times using a fluid transfer system.

Some optional features:
The size and shape of the pre-filled pod and the re-fillable pod match one another in order to enable the same vaping device main body to work with both the pre-filled pod and the re-fillable pod.
The main body of the vaping device is configured to slide, dock or otherwise engage with a desktop docking station that is itself configured to re-fill and re-charge a re-fillable pod fitted to the device.
The main body of the device is configured to slide, dock or otherwise engage with a portable docking station that is itself configured to re-fill and re-charge a re-fillable pod fitted to the device.
The portable docking station is a case that securely stores the device and automatically re-fills and re-charges it.
The vaping device body includes a fluid path that leads from a fluid inlet to a stem or nozzle or aperture that is configured to engage with a reciprocal aperture, stem or nozzle in the refillable pod.
The vaping device body includes a slot or other aperture that reveals a portion of a pod inserted or otherwise engaged with the body to enable a user to tell the flavor of the liquid in that pod.
The re-fillable pod includes a liquid level sensing sub-system.
The vaping device body includes a sub-system that measures or uses signals from the liquid level sensing sub-system in the re-fillable pod.
The vaping device body includes a sub-system that sends signals from the liquid level sensing sub-system in the re-fillable pod to a microcontroller that controls a fluid transfer system.
The microcontroller is in the vaping device itself, or in a desktop dock, or in a portable case dock.
The fluid transfer system is in the vaping device itself, or a desktop or portable case dock, and is configured to re-fill a re-fillable pod fitted to the device.
The fluid transfer system automatically stops pumping when the liquid in the liquid reservoir in the re-fillable pod reaches a preset level or quantity.
the handheld vaping device includes a rechargeable battery, the fluid transfer system, a liquid level sensing sub-system and a liquid refill container.
the handheld vaping device includes a rechargeable battery, and is configured to engage with an external fluid transfer system, and an external liquid level sensing sub-system.
the refillable pod is also provided pre-filled with liquid at a point of sale.
the refillable reservoir that is configured to be refillable using the pump is provided empty of liquid at a point of sale.

The pre-filled pod includes an authentication chip or module.
The re-fillable pod includes an authentication chip or module.
The vaping device body includes an authentication sub-system that reads the authentication chip or module and only operates if an authentication routine is passed.
The pre-filled or re-fillable pod uses an atomiser which is one of the following: a cotton wick and wire coil; a ceramic wick and wire coil; a ceramic wick and planar coil; a ceramic wick and non-planar coil; a wick-less and coil-less atomiser; a metal blade type atomiser.

In this document, we will follow this approach of stating a generalisation of a feature, together with some optional features that may be implemented with that feature. Any such generalised feature may be combined with any one or more compatible other generalised features, and any optional feature may be combined with any one or more generalised feature and any one or more other optional features.

Pre-Filled and Re-Fillable Tips or Pods that Work with Different Vaping Device Types In the preceding section, we also looked at things from the perspective of the features of a handheld vaping device 10, 8 that can work with different types of pods, both pre-filled, closed pods 2 and also automatically refillable pods 11. In AYR, pre-filled and re-fillable pods work with a portable vaping device that is refillable from a desktop dock 6 (AYRDock), or a portable dock 7, such as a re-fill and re-charge case (AYRCase) as well as when the vaping device is a stand-alone device 8 into which the refill bottle 5 or container can be directly attached (AYRMod 8). So we can also look at things from the perspective of a re-fillable pod that can work with different types of vaping device (e.g. a stand-alone vaping device with an integral pump and re-fill bottle; a vaping device in combination with a re-fill docking station for that device; a vaping device in combination with a re-fill docking case for that device.

We can generalise as follows:
A vaping system that includes (i) a re-fillable tip or pod and (ii) a pre-filled, non-re-fillable tip or pod, that are each configured to fit in, or attach to, two or more of the following vaping devices:
(a) a portable vaping device body with no integral liquid transfer pump;
(b) a portable vaping device body configured to engage with a liquid refilling dock including a liquid pump;
(c) a portable vaping device body configured to engage with a portable case including a liquid pump; and
(d) a portable vaping device body with an integral liquid pump.

Some optional features:
The size and shape of the pre-filled pod and the re-fillable pod match one another in order to enable the same vaping device main body to work with both the pre-filled pod and the re-fillable pod.
The portable vaping device body includes a fluid path that leads from a fluid inlet to a stem or nozzle or aperture that is configured to engage with a reciprocal aperture, stem or nozzle in the refillable pod.
The portable vaping device body includes a slot or other aperture that reveals a portion of a pod inserted or otherwise engaged with the device to enable a user to tell the flavor of the liquid in that pod.
The re-fillable pod includes a liquid level sensing sub-system.

The portable vaping device body includes a sub-system that measures or uses signals from the liquid level sensing sub-system in the re-fillable pod.

The portable vaping device body includes a sub-system that sends signals from the liquid level sensing sub-system in the re-fillable pod to a microcontroller that controls a fluid transfer system.

The microcontroller is in the vaping device body itself, or in a desktop dock, or in a portable case dock.

The fluid transfer system is in in the vaping device body itself, or a desktop or portable case dock, and is configured to re-fill a re-fillable pod fitted to the device.

The fluid transfer system automatically stops pumping when the liquid in the liquid reservoir in the re-fillable pod reaches a preset level or quantity.

the handheld vaping device body includes a rechargeable battery, the fluid transfer system, a liquid level sensing sub-system and a liquid refill container.

the vaping device body includes a rechargeable battery, and is configured to engage with an external fluid transfer system, and an external liquid level sensing sub-system.

the refillable pod is also provided pre-filled with liquid at a point of sale.

the refillable reservoir that is configured to be refillable using the pump is provided empty of liquid at a point of sale.

The pre-filled pod includes an authentication chip or module.

The re-fillable pod includes an authentication chip or module.

The vaping device body includes an authentication sub-system that reads the authentication chip or module and only operates if an authentication routine is passed.

The AYRCase System

We will now describe the AYR system in more depth. We will describe the complete AYRCase system.

Figure 2:
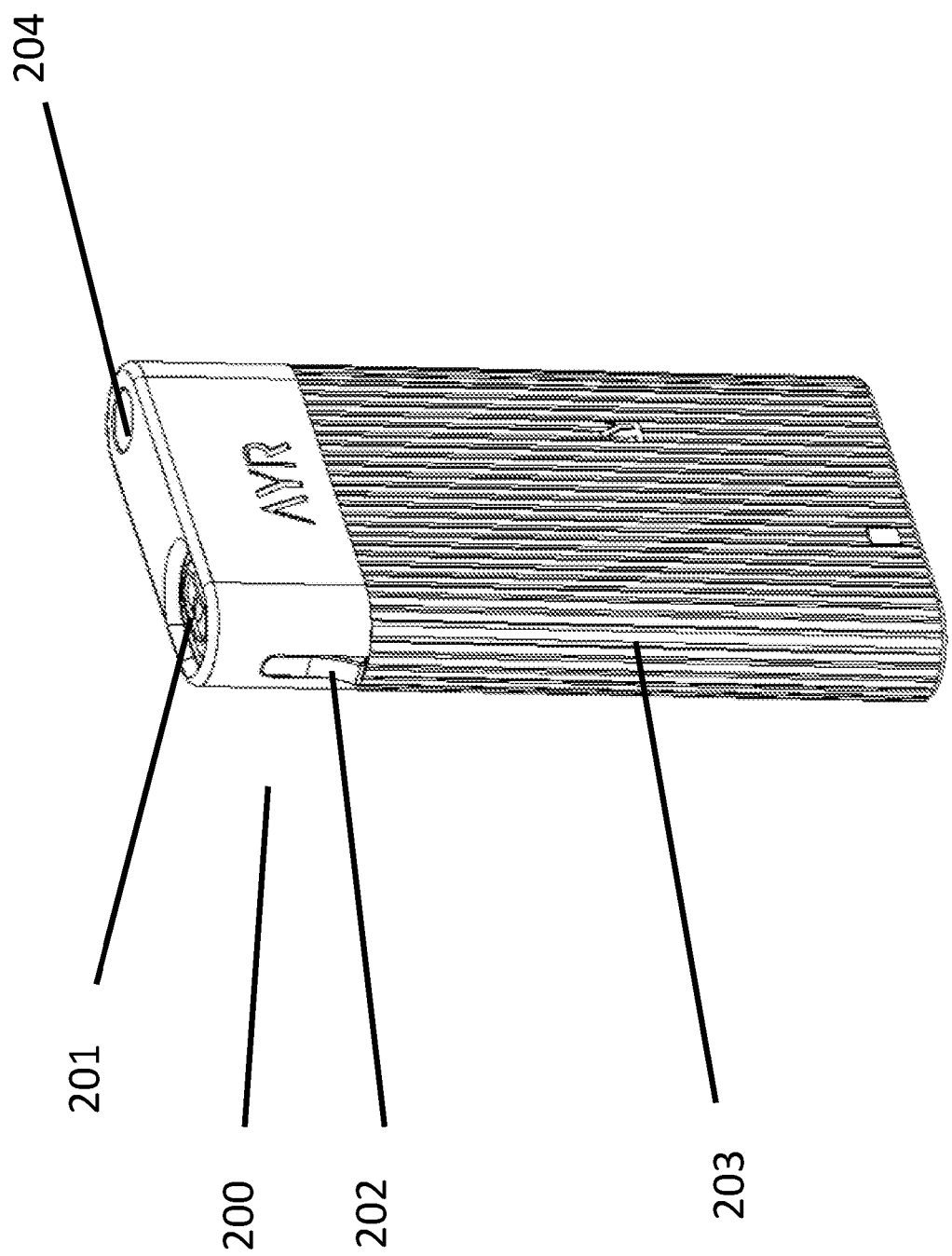
FIG. 2 is a perspective view of a re-fill and re-charge case for a vaping device.
Figure 3:
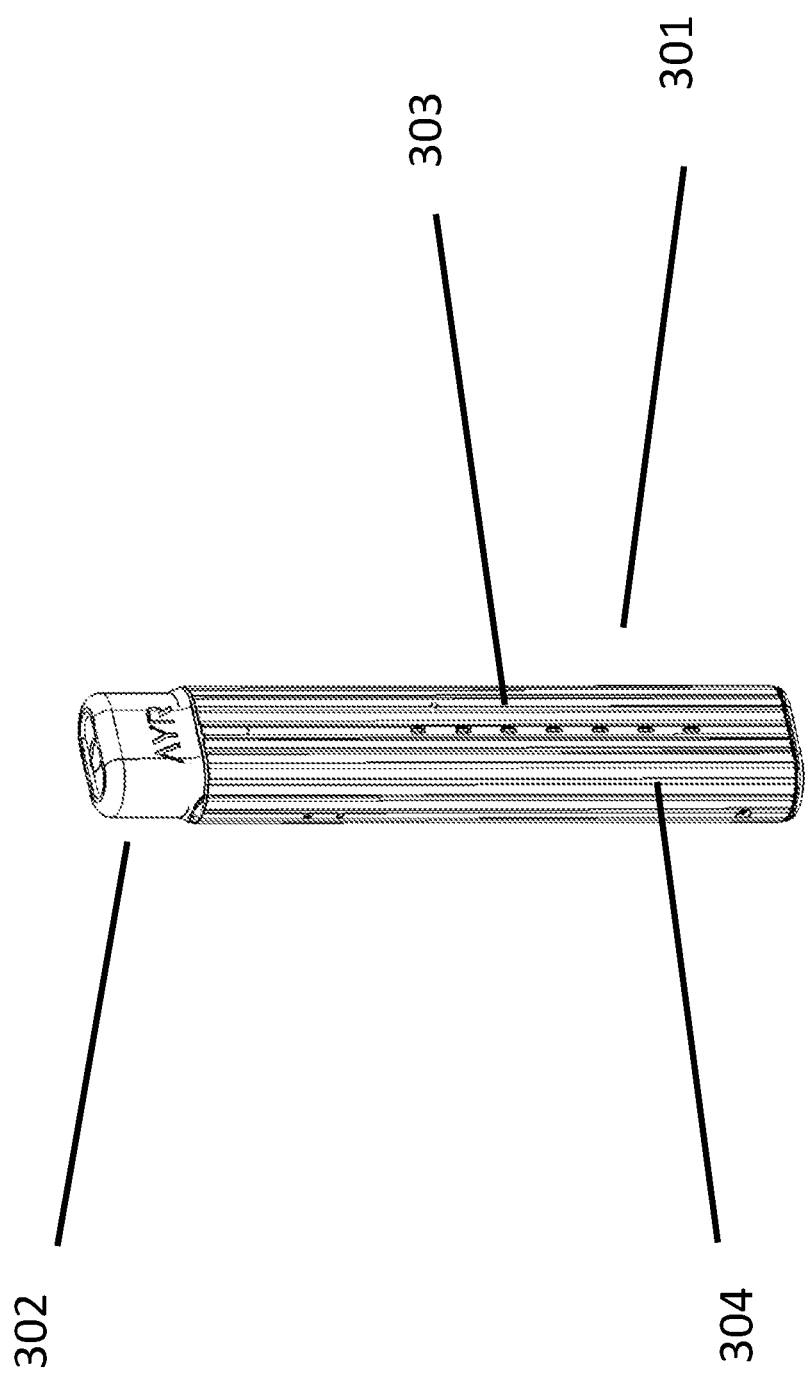
FIG. 3 is a perspective view of the vaping device.

FIG. 2 shows the AYRCase re-fill and re-charge case, indicated generally at 200; it stores a personal vaping device, (PV) vaping device, the top of which is visible at 201, shown in FIG. 3. The case 200 includes a PV ejector switch 202 which when pushed releases a catch that otherwise retains a spring that the PV has compressed when it is fully inserted into the case; this enables the PV 201 to rise up several mm so a user can readily grasp it (for example, when holding the case with one hand, the user can trigger the catch and then grip the PV with his or her lips to fully extract it from the case). The case includes a display (not shown) on its top surface which shows various operational parameters (e.g. whether the case is pumping liquid; the liquid level in the re-fill bottle; the battery level in the case; connectivity status). A ribbed, metal extrusion 203 provides the external shell; this is low cost, and different materials, colours and finishes are readily possible. The extrusion 203 is a one-piece sleeve that slides over an internal chassis, making assembly, as well as dis-assembly for repairs or re-cycling, fast and efficient. The case is activated by pressing or touching on/off button 204.

In FIG. 3, the PV or vaping device is shown: it includes a vaping device body 301 and a tip or pod 302 that slides into the vaping device body 301 and secures with a magnetic or friction latch. As noted above, this tip of pod can be either a pre-filled, single use, non-recyclable tip that includes a small liquid reservoir and integral heating atomiser. Alternatively, it can be re-fillable tip. The external dimensions of the lower portion of both types of pods are identical so they can both fit into the vaping device body 303. Careful positioning of the various interfaces (electrical power, data and liquid) is needed to ensure compatibility of pre-filled and re-fillable pods with the device body 301. In addition to the vaping device body 301 which permits re-fillability, the AYR system also includes a standard vaping device body (not shown) which is only compatible with pre-filled pods; this is a very low cost to manufacture version for users who want only to use pre-filled pods.

As with the case, a ribbed, metal extrusion 304 provides the external shell; this is again low cost, and different materials, colours and finishes are readily possible. The extrusion 304 is a one-piece sleeve that slides over an internal chassis, making assembly, as well as dis-assembly for repairs or re-cycling, fast and efficient. A series of 8 LED lights 303 runs down one side of the device body 303; when the vaping device is withdrawn from the case ready for a vaping session, then all 8 LEDs are lit; a timer or other measuring system, sequences progressively extinguishing each light; for example, after 10 seconds of inhalation, or 5 inhalations (or some other number) then the first or top light is extinguished; after a further 10 seconds of inhalation or 5 inhalations, the first and the second light is extinguished. And so on, until when all lights are extinguished, then nicotine approximately equivalent to that consumed when smoking a single cigarette has been delivered or inhaled. The final light can be programmed to last slightly longer than other lights, corresponding to the smokers' typical ritual of trying to get the most out of their final cigarette puff. The AYR system mimics where possible those rituals of smoking: doing so maximises the likelihood that smokers will switch away from smoking cigarettes to vaping.

Figure 4:
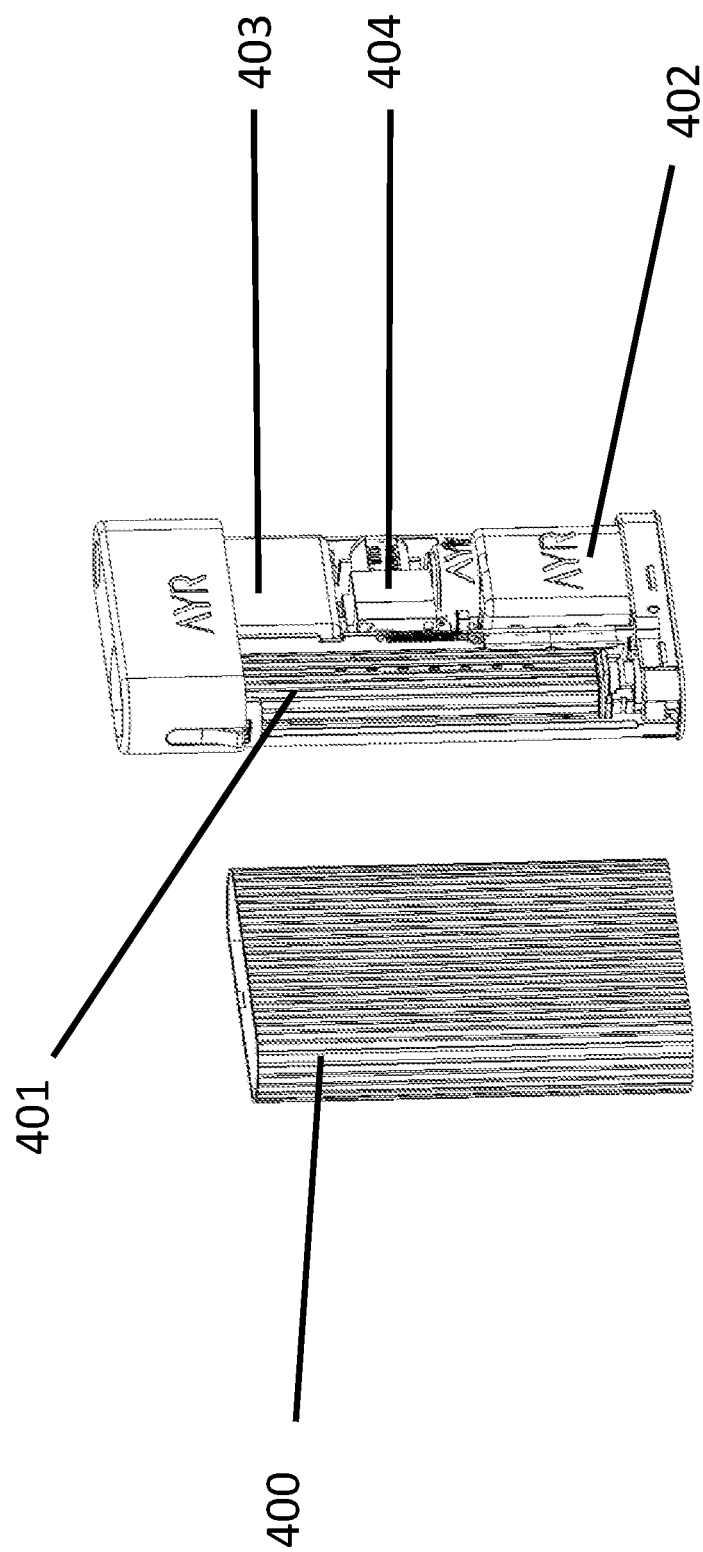
FIG. 4 is a perspective view of the re-fill and re-charge case with its extruded outer shell removed, showing key internal components.
Figure 5:
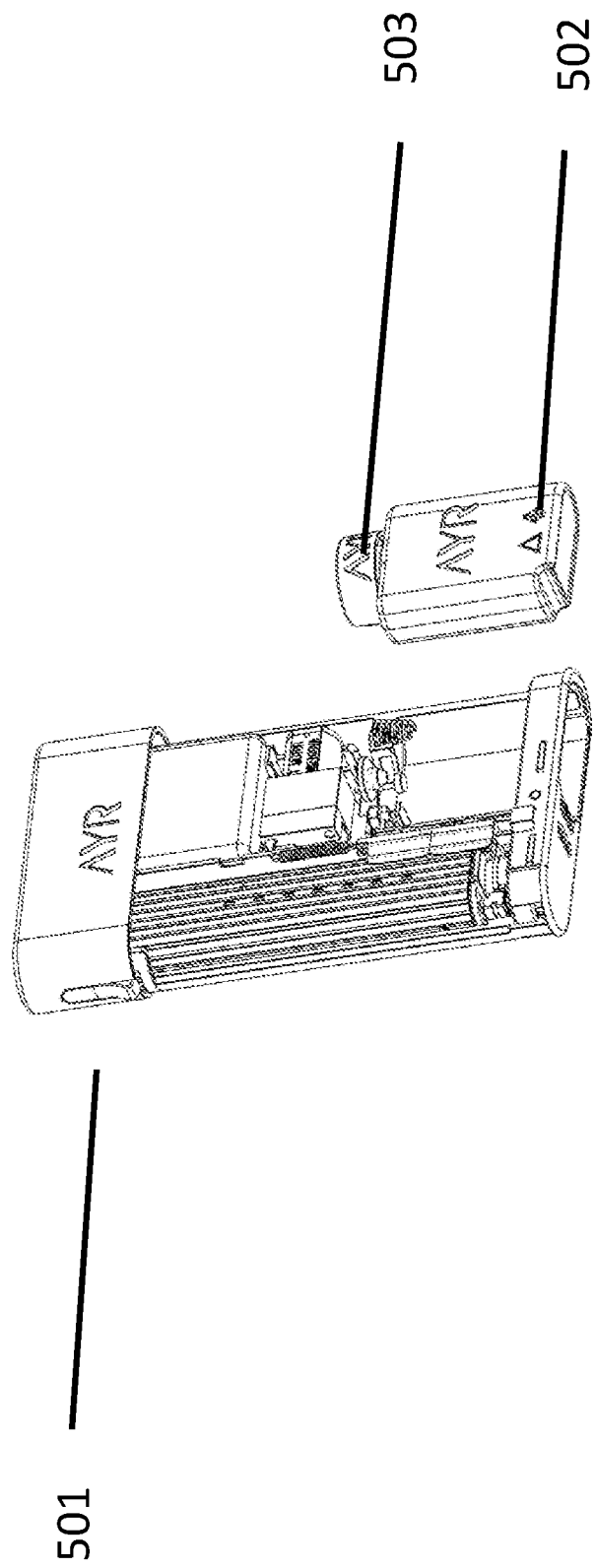
FIG. 5 is a perspective view of the re-fill and re-charge case with its extruded outer shell removed, and the re-fill bottle shown outside of the case.

Returning to the case, we can remove the metal sleeve extrusion 400, as shown in FIG. 4. We can see the PV 401 in its storage position, together with the 10 mL atomisable liquid refill bottle 402, main battery 403 and electric peristaltic pump 404. FIG. 5 shows the case 501 with the refill bottle 502 outside of the case 501; the bottle 502 includes a child-proof cap 503; this cap 503 is removed in normal use before the bottle 502 is inserted into the case 501.

Figure 6:
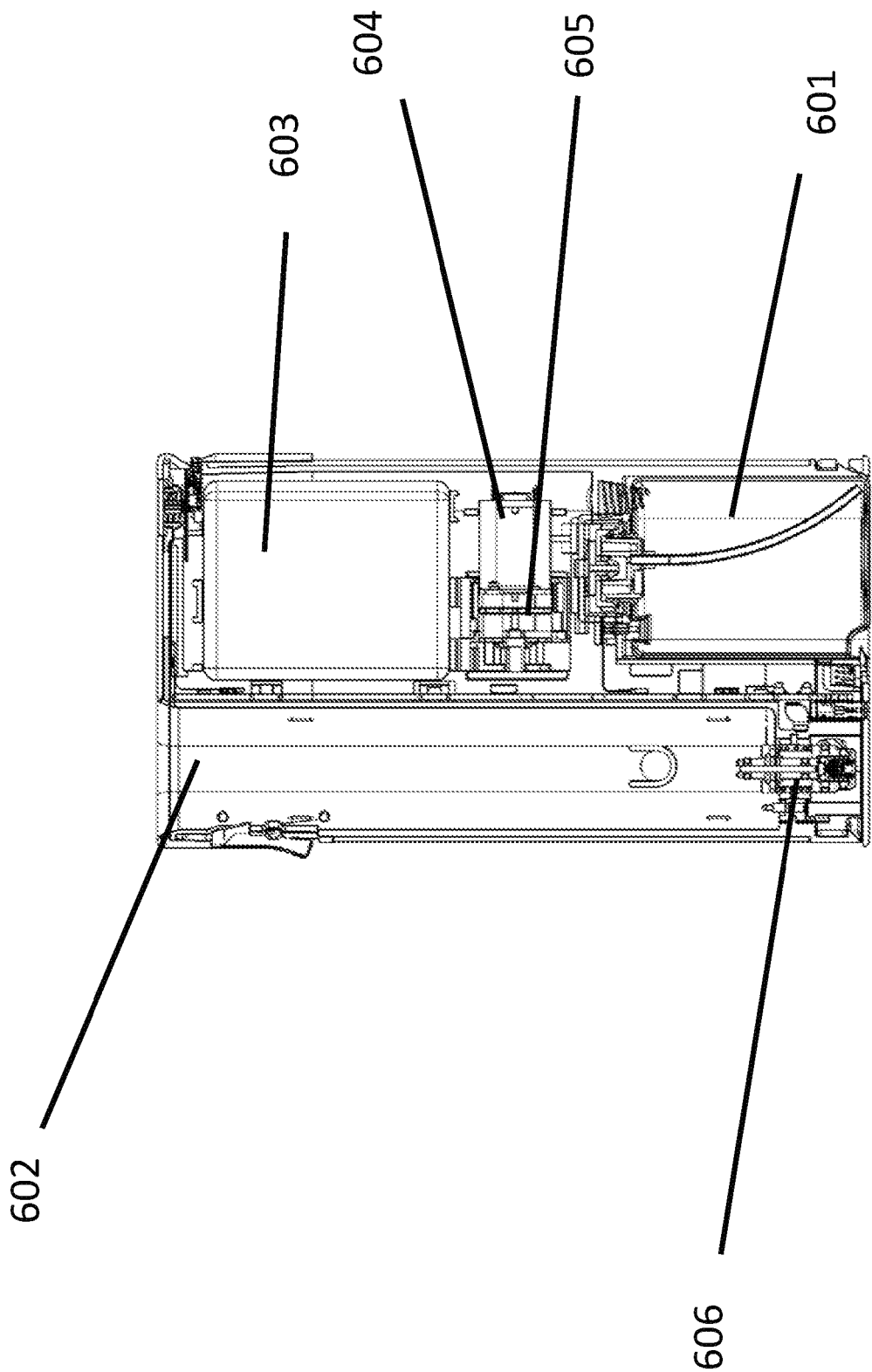
FIG. 6 is a cross-sectional view of the re-fill and re-charge case.

FIG. 6 is a cross sectional view through the case, with the liquid refill bottle 601 in position, but the PV removed, showing the channel 602 that receives the PV. Key elements in the case are a main battery 603, used to recharge the smaller battery in the PV; an electric motor 604 driving a peristaltic pump 605, which automatically withdraws liquid from the refill bottle 601 along a food-grade tubing (not shown) which is resistant to e-liquid leaching. The tubing continues to a liquid feed nozzle and valve 606 in the case; when the PV is pressed down against the nozzle, the valve opens, permitting liquid to be pumped into the PV device body and up into the tip.

Figure 7:
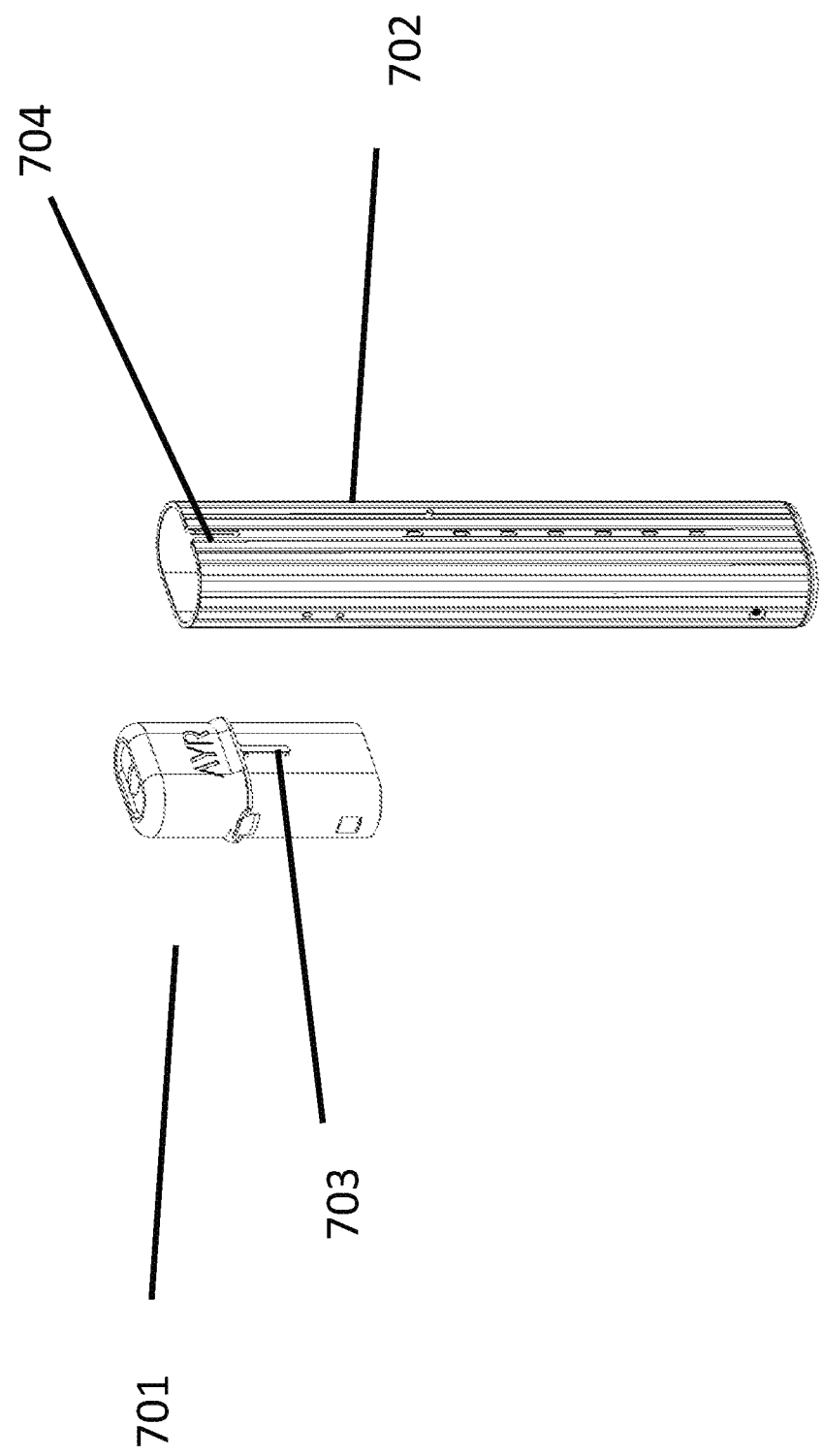
FIG. 7 is a perspective view of the vaping device body with the tip or pod removed.

FIG. 7 shows the PV; a tip or pod 701 is shown removed from the main body 702 of the PV; it is secured in position in the PV by a small magnet in the PV. The tip or pod 701 can be pre-filled with liquid at a liquid filling plant, and not be capable of being refilled at all. Alternatively, it may be re-fillable using the case or other form of dock. The external size and shape is the same for both variants, for full compatibility. The pre-filled pod includes a coloured rib 703; pods with different liquid flavours use different colours. The re-fillable pod has another colour or pattern. The rib 703 slides into slot 704 in the case; the rib has a dual function: first, to ensure the pod 701 is slid into the device body 702 in the correct orientation (the physical and electrical interfaces are not symmetrical) and secondly to give a visual indication of the type or flavour of pod that is being used.

Figure 8:
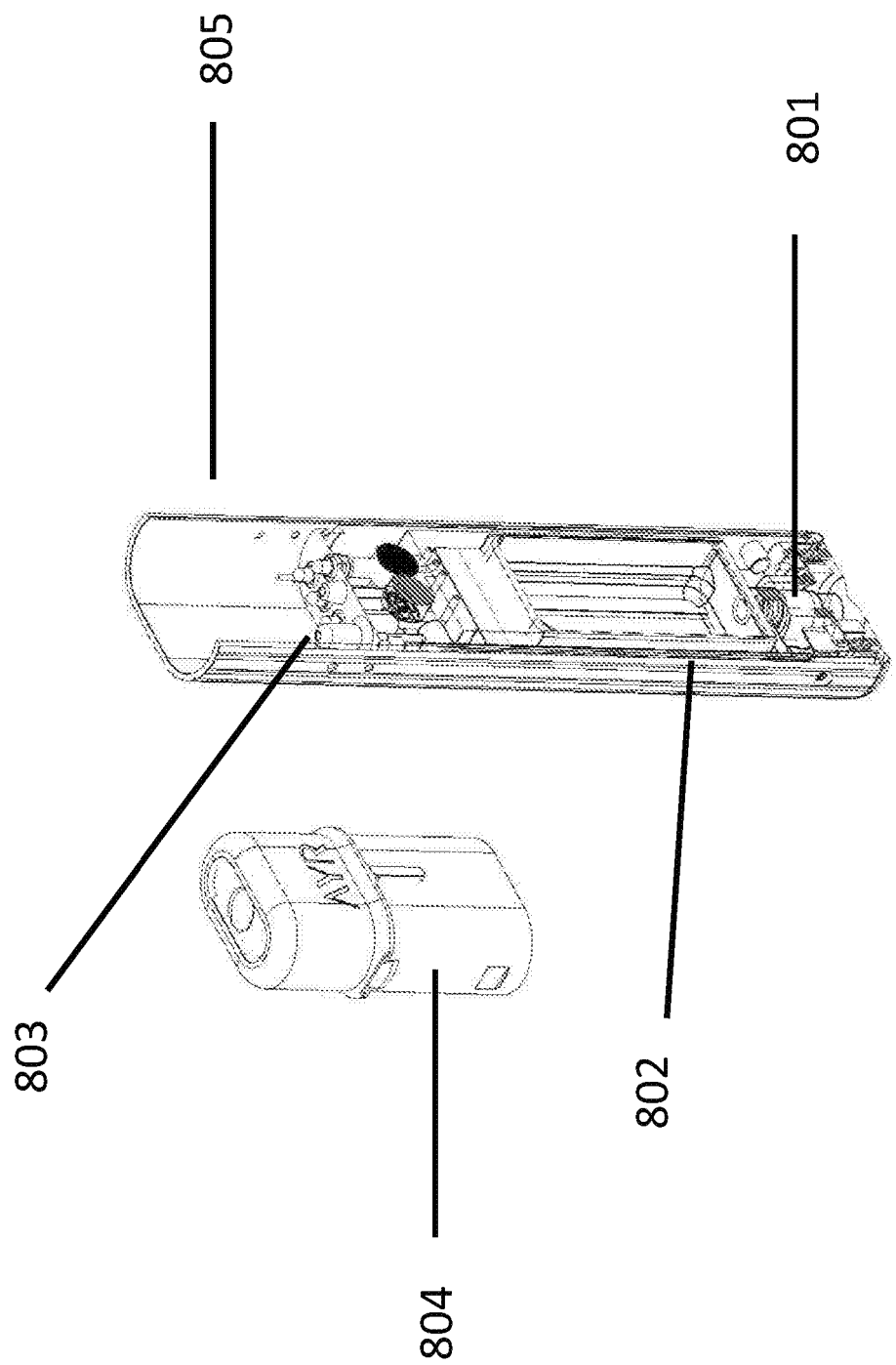
FIG. 8 is a cross-sectional view of the vaping device body.

FIG. 8 shows a cross section through the re-fillable variant of the PV. It includes a liquid filling aperture and valve 801, a liquid path 802 from the liquid filing aperture and valve 801 up to a liquid nozzle 803 that mates with an aperture in the base of a re-fillable tip 804. The liquid path 802 is formed from a moulded channel in the plastic chassis to which the major components in the PV are fixed (e.g. the small rechargeable battery, main circuit board) and over which a metal, extruded outer sleeve 805 can be slid to form the finished vaping device. The chassis moulding hence forms three sides of the liquid transfer channel 802; it is covered with an ultrasonically welded plastic or PET film; this is a cheap, easy to manufacture way of creating a liquid path in the PV and removes the need for a separate small bore liquid pipe.

Figure 9:
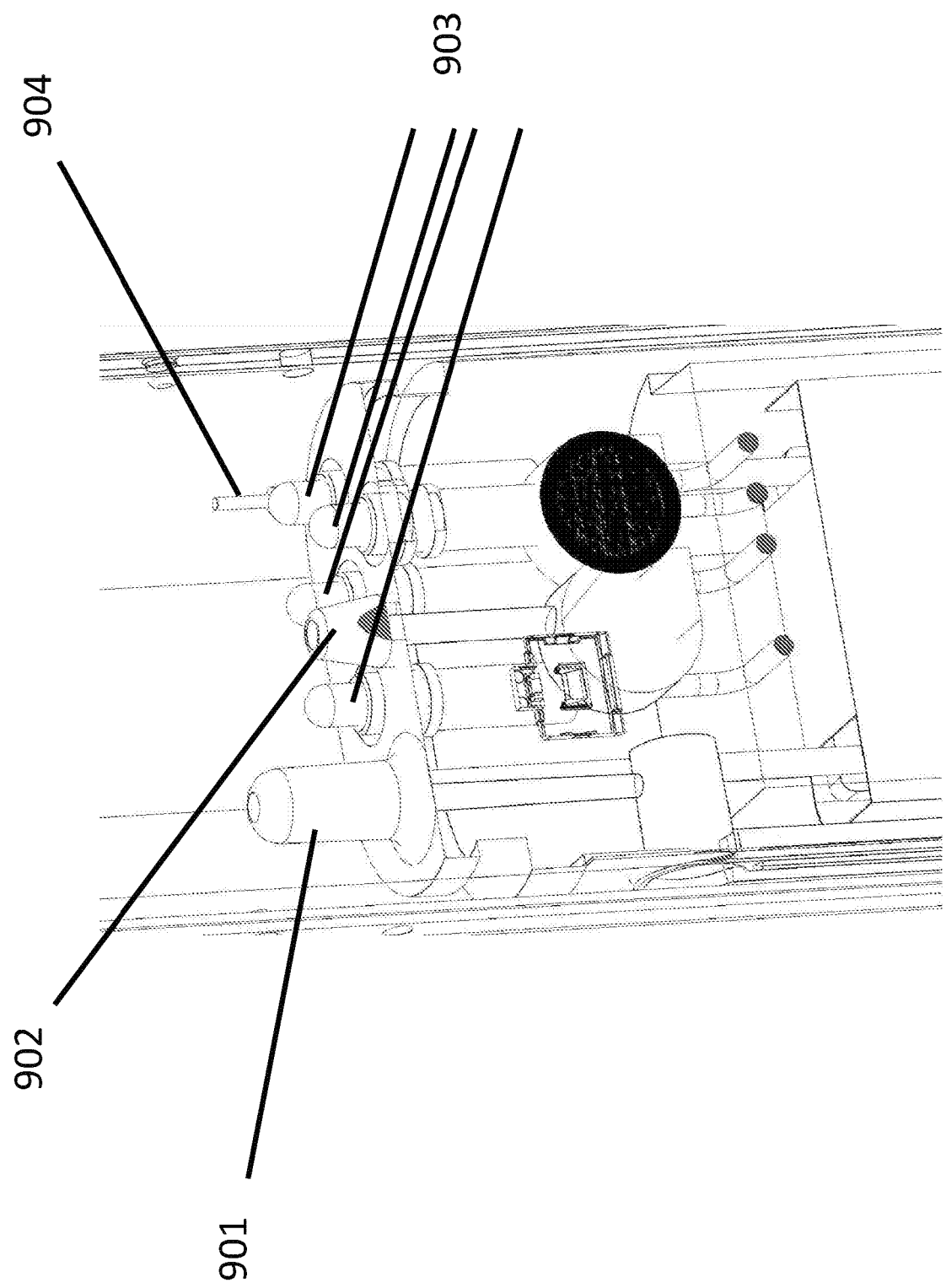
FIG. 9 is a cross-sectional view of the top-end of the vaping device body, showing the liquid, electrical and power interfaces.

As shown in FIG. 9, the PV has a liquid filling nozzle 901 that mates with a liquid filling aperture in the base of the re-fillable pod. The PV includes an air pressure drop signal nozzle 902 which is connected to an air pressure sensor in the PV; when the user inhales, negative air pressure is communicated to the air pressure sensor via the air pressure drop signal nozzle 902. This pressure drop pathway is entirely separate from any air flow pathways that might include droplets of e-liquid or condensation, to minimise the risk of damaging the air pressure sensor with nicotine liquid or other chemicals that could impair the correct operation of the air pressure sensor. This separation is especially important where a sensitive pressure measurement device, such as a solid-state MEMS type pressure sensor is used since these devices need to be protected from e-liquid contamination and benefit from having a dedicated and distinct air pressure path. These sorts of sensors are especially useful where the device needs to track accurately detailed metrics on inhalation—i.e. not just simply counting each inhalation, but also measuring and recording accurately the strength, depth, volume, duration and air velocity profiles over time for each inhalation (and also exhalation where its useful to be able to track exhalation data, as a form of spirometer—this data could be especially valuable where there device is used in clinical trial for smokers where it is valuable to track lung performance improvements, e.g. as the trial participants reduce or cease smoking).

Power to the heating coil is via electrical power contacts, one of which is shown at 904.

The PV also includes 4 pogo pin connectors 903 that provide electrical and signal contacts to a capacitive sensor circuit. This sensor circuit is located in the external dock for the AYRDock and AYRCase variants; it is in the vaping device itself for the AYRMod variant. The re-fillable pod includes a pair of capacitive plates in the liquid reservoir in the pod and the 4 pogo pins provide the signals between the capacitive plates and a capacitive sensing circuit, which is either a dedicated chip or an ASIC that incorporates the required circuitry.

Figure 10:
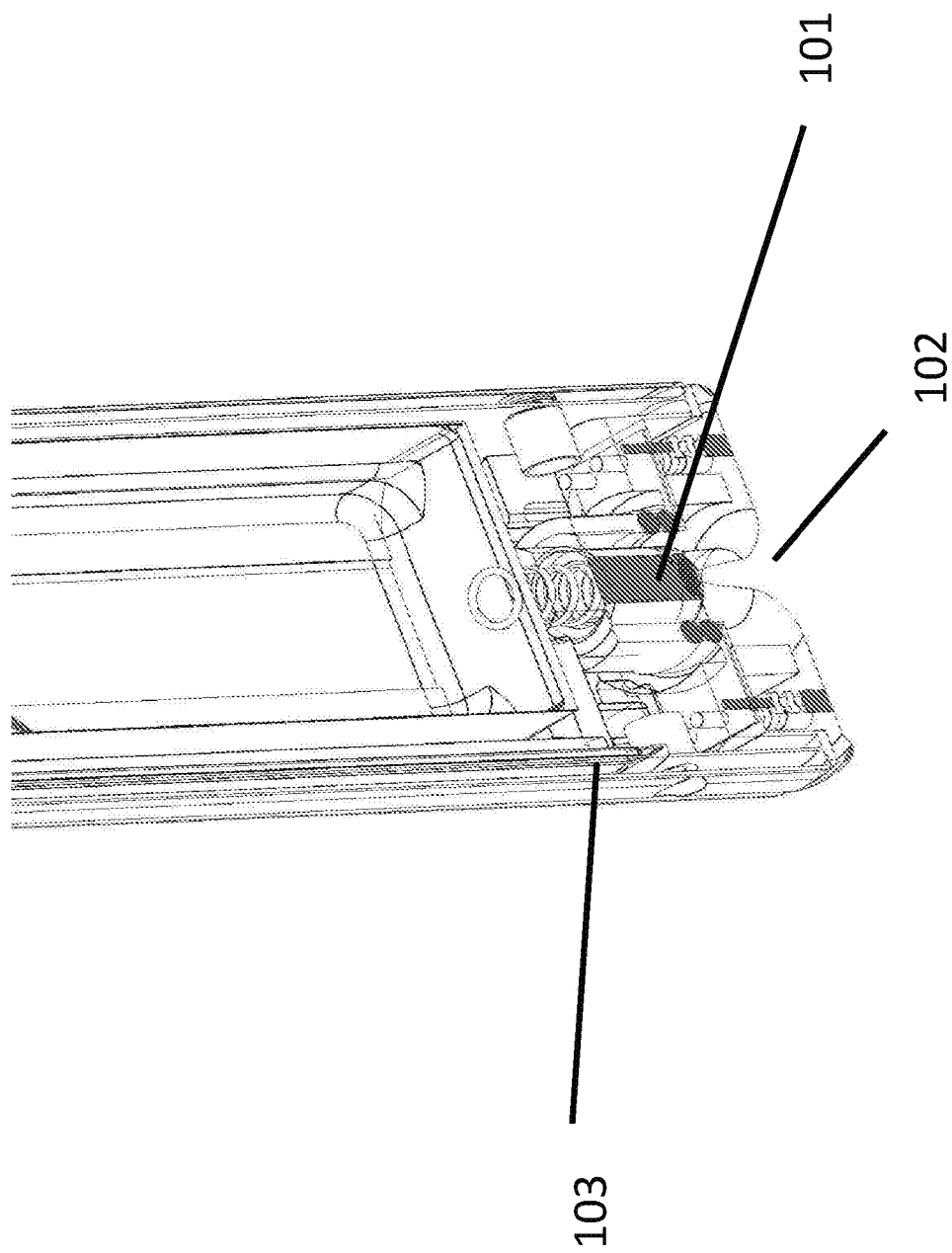
FIG. 10 is a cross-sectional view of the bottom-end of the vaping device body, showing the liquid filling aperture and valve.

FIG. 10 shows the base of the PV; a spring-mounted filing valve 101 is unseated when the PV is pushed down against the filling nozzle in the case and provides an unobstructed liquid path from the filling aperture 102 in the base of the PV up through the liquid channel 103, which leads to the tip filling nozzle.

Figure 11:
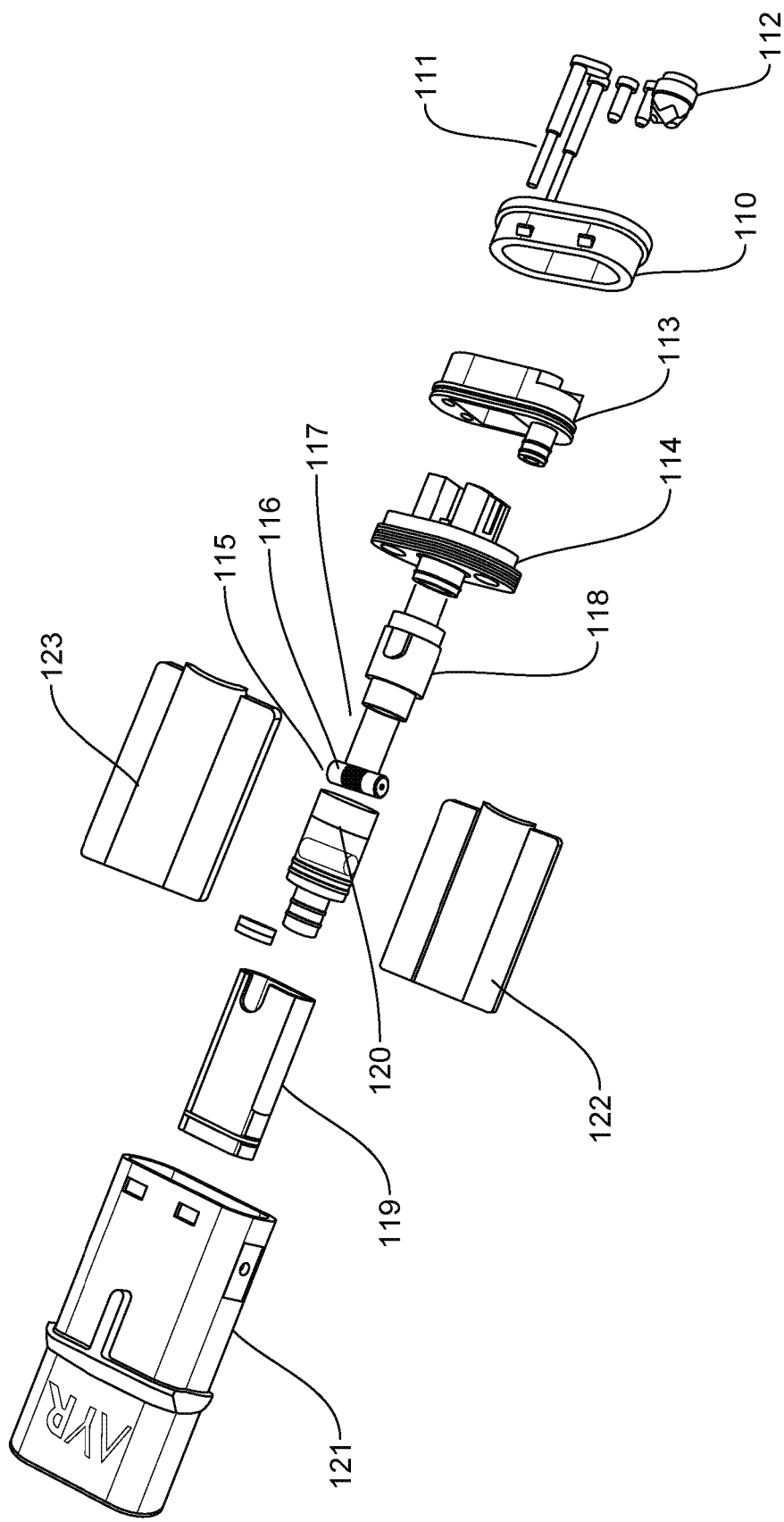
FIG. 11 is a perspective, exploded view of the tip or pod.

FIG. 11 is an exploded view of the tip. Key elements are a base cap 110, four pogo pin contacts 111, liquid filling aperture with one-way valve 112 that opens only when the pump is actively pumping liquid into the tip liquid reservoir under pressure, liquid stem 113 that sits over valve 112, and a silicone atomiser base 114 that the atomising unit sits on. The atomising unit contains a ceramic wick 115 around which a stainless steel heating coil wire 116 is wound, although any other atomising system is possible. Power wires 117 feed the heating coil wire 116.

A silicone inner cylinder that sits inside generally cylindrical silicone outer sheath 119 is formed from a lower section, called the chimney 118, and an upper section 120, which supports the ceramic wick 115. The silicone chimney 118 sits on the atomiser base 114. Air flows up through the central aperture of the chimney 118 and over the wick 115 and coil 116, forming an aerosol including droplets of the liquid. A liquid reservoir is formed by the inner surface of mouthpiece 121 and the outer surface of the silicone outer sheath 119. A pair of channels is formed in-between the silicone outer sheath 119 and the silicone inner parts 118, 120 that fit inside the outer sheath 119; these are liquid channels that feed liquid in from the liquid reservoir and up into the wick 115. A pair of stainless steel capacitive sensing plates 122 and 123 sit inside the liquid reservoir. Subsequent figures will expand on this description.

Figure 12:
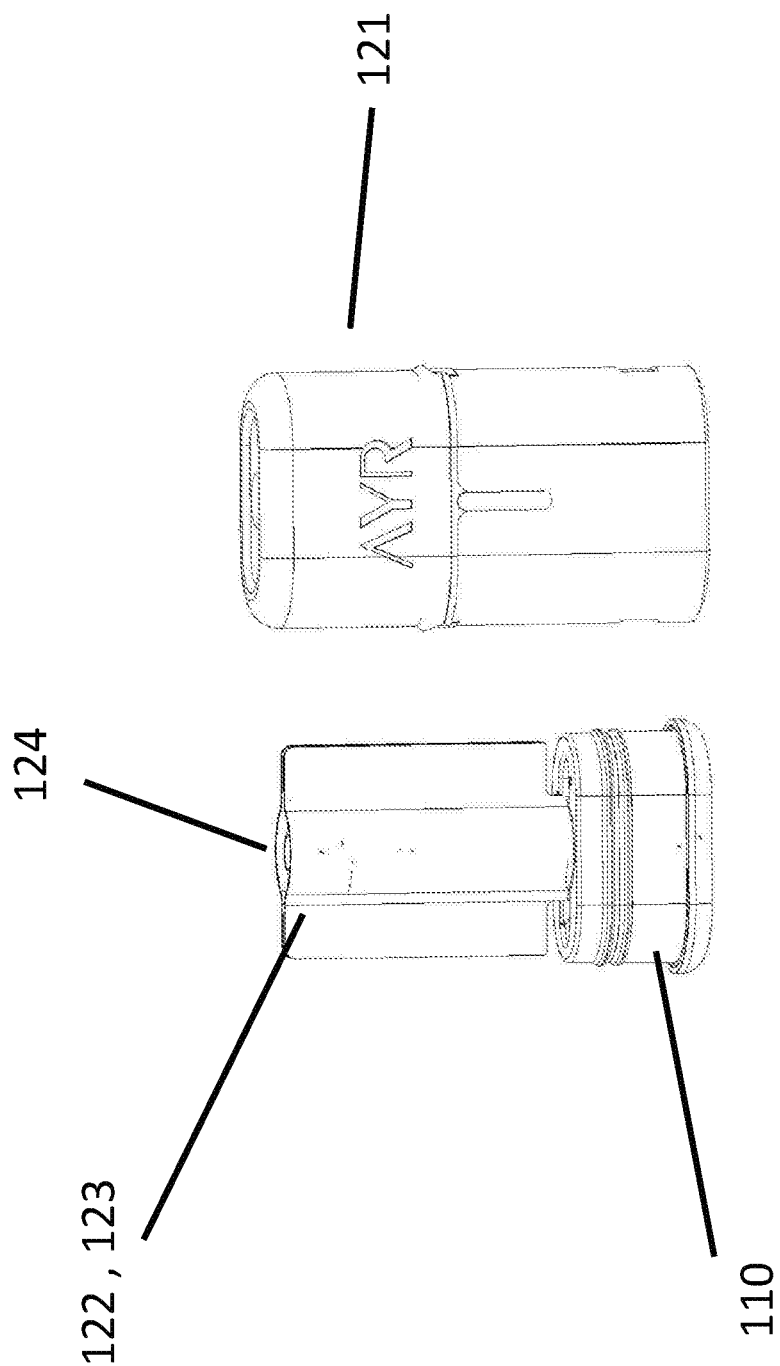
FIG. 12 is a view of the pod with the outer mouthpiece removed, showing the internal capacitive sensor plates.

FIG. 12 shows the tip fully re-assembled, but with just the mouthpiece 121 lifted off. The pair of stainless steel capacitive sensing plates 122 and 123 is shown; these fully enclose the silicone outer sheath 119 shown in preceding FIG. 11, which in turn fully encloses the upper and lower sections of the inner silicone cylinder 118, 120. The capacitive plates 122 and 123 have flat sides and a curved, part-cylindrical central section 124; this part-cylindrical central section 124 sits over the cylindrical silicone outer sheath 119. The region outside of the stainless steel capacitive sensing plates 122 and 123 and the plastic mouthpiece 121, when the mouthpiece 121 is fitted onto the atomiser base 114, is the liquid reservoir and is hence normally filled with liquid; the cover 121 is slid over this unit and liquid leakage prevented by double O rings.

During use, a typical scenario is for the liquid level sensing system to determine if the liquid level in this reservoir is above or below a threshold, typically ½ full or ⅔rds full; this measurement routine takes place when the PV is placed in the case and the case is oriented vertically (as measured by an accelerometer chip in the case)—by restricting filling to when the device is vertical, that greatly reduces the challenge of accurately sensing the amount of liquid in the liquid reservoir. If the level is below the threshold, then the pump is activated and continues to pump liquid into the tip reservoir until the threshold is reached. More details of the liquid level sensing system is given in Section D.

Figure 13:
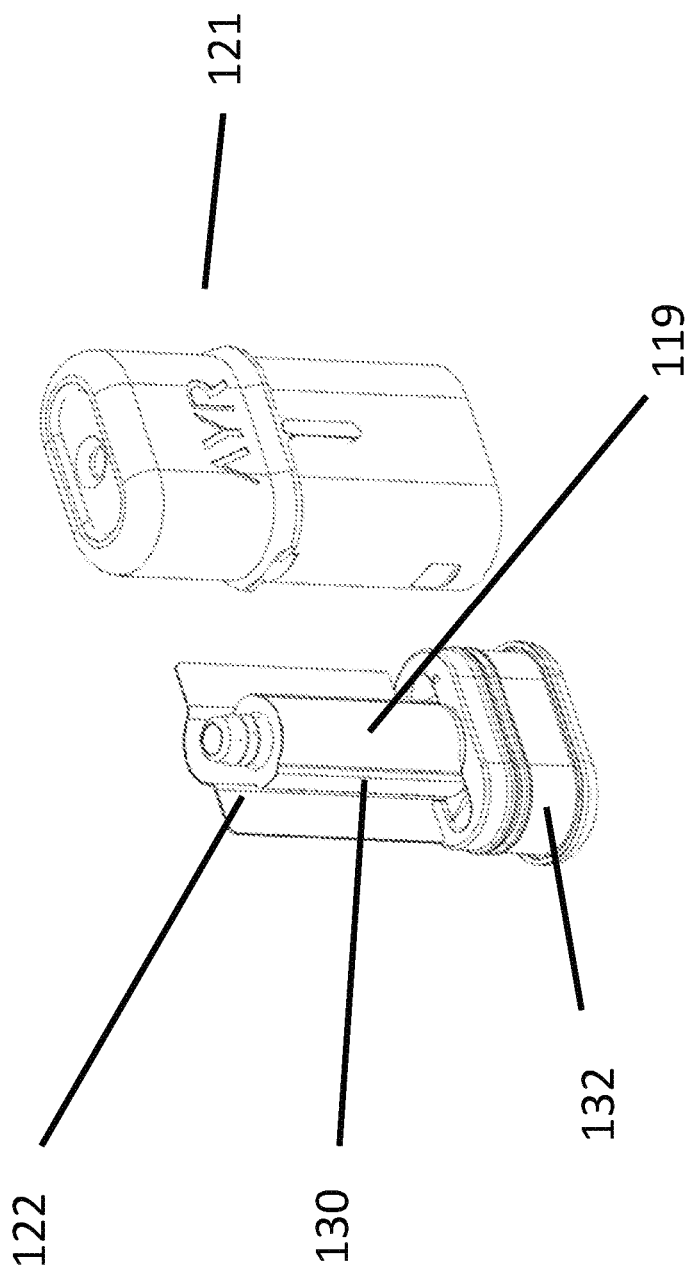
FIG. 13 is a view of the pod with the outer mouthpiece removed, showing one of the internal capacitive sensor plates and the silicone sheath that surrounds and supports an atomising element inside the silicone sheath.

FIG. 13 shows this arrangement with one of the stainless steel capacitive sensing plates removed, leaving just the rear sensor plate 122; it shows the generally cylindrical silicone outer sheath 119 that forms an inner surface of the liquid reservoir. The silicone outer sheath 119 shows two ridges 130 extending up each side; inside the sheath 119 is the lower and an upper generally cylindrical silicone inner parts 118, 120; these parts 118, 120 fit tightly within the silicone outer sheath 119, apart from a channel behind each ridge: each channel is a liquid path 131 from the reservoir and into the wick; the channel is formed from the gap in between the inner surface of the silicone outer sheath 119 and the outer surface of the silicone parts 118, 120 defined by the ridges 130. The gap between the opposing capacitive sensing plates 122 and 123 (not shown) is clearly apparent; the gap is needed for capacitive measurement. Accurate and consistent separation of the capacitive plates is needed for accurate and consistent capacitive measurement; the outer silicone sheath 119 and small ribs or features on the atomiser base 132 enable this.

Figure 14:
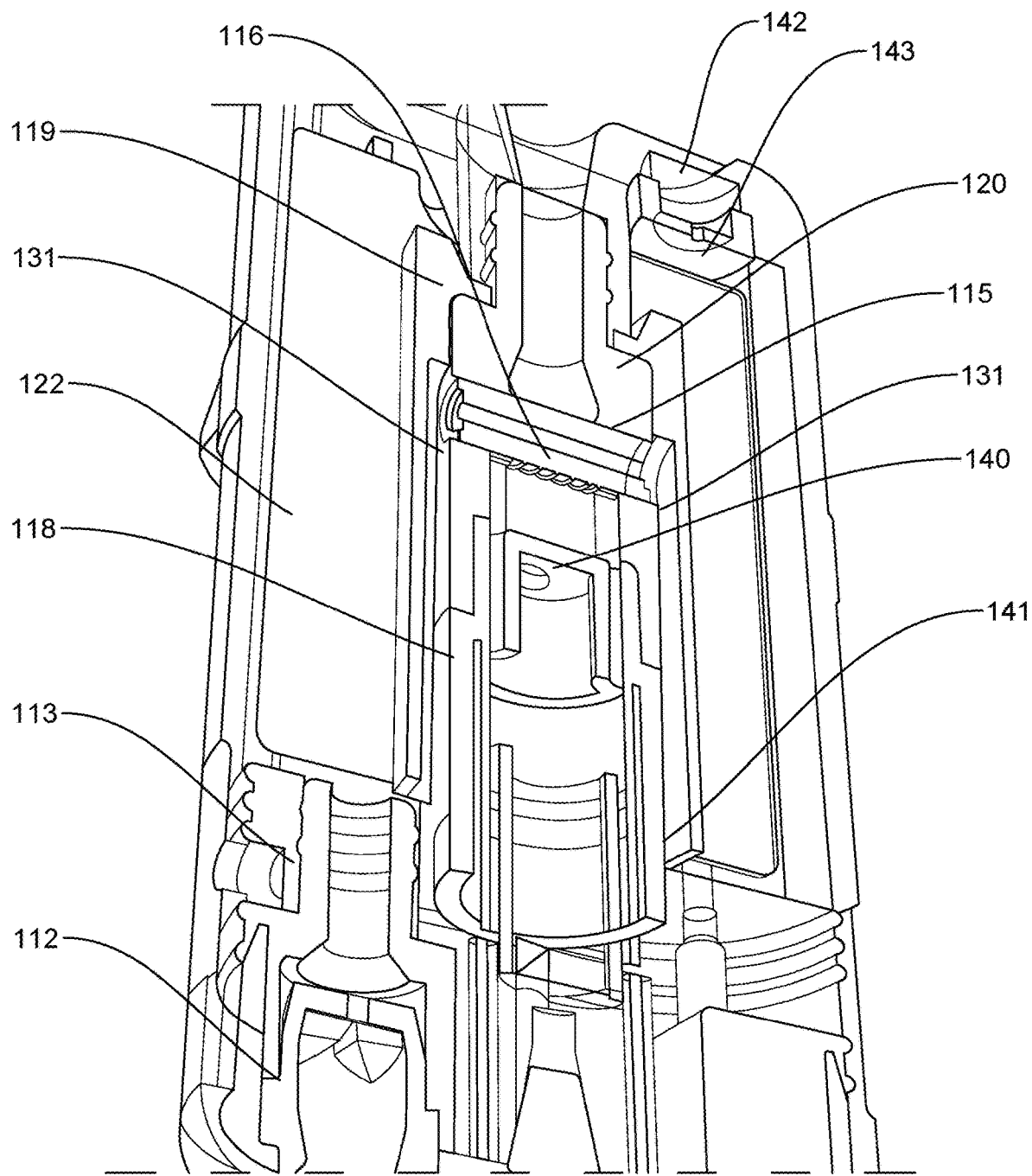
FIG. 14 is a cross-sectional view of a portion of the pod, showing how all the elements shown in the exploded view of FIG. 11 fit together.

FIG. 14 shows this internal structure more clearly in a perspective cross-sectional view of the fully assembled pod; the silicone outer sheath 119 includes ridges that define an internal pair of channels 131 through which liquid can pass; the cross section is a slice that passes through these channels 131. The silicone inner part that sits inside silicone outer sheath 119 is formed from a lower section, called the chimney 118, and an upper part 120, which supports the ceramic wick 115. Air passes up through this chimney 118 and through a pair of oppositely-angled apertures 140 into the atomising chamber around the ceramic wick 115 and heating coil 116.

Figure 15:
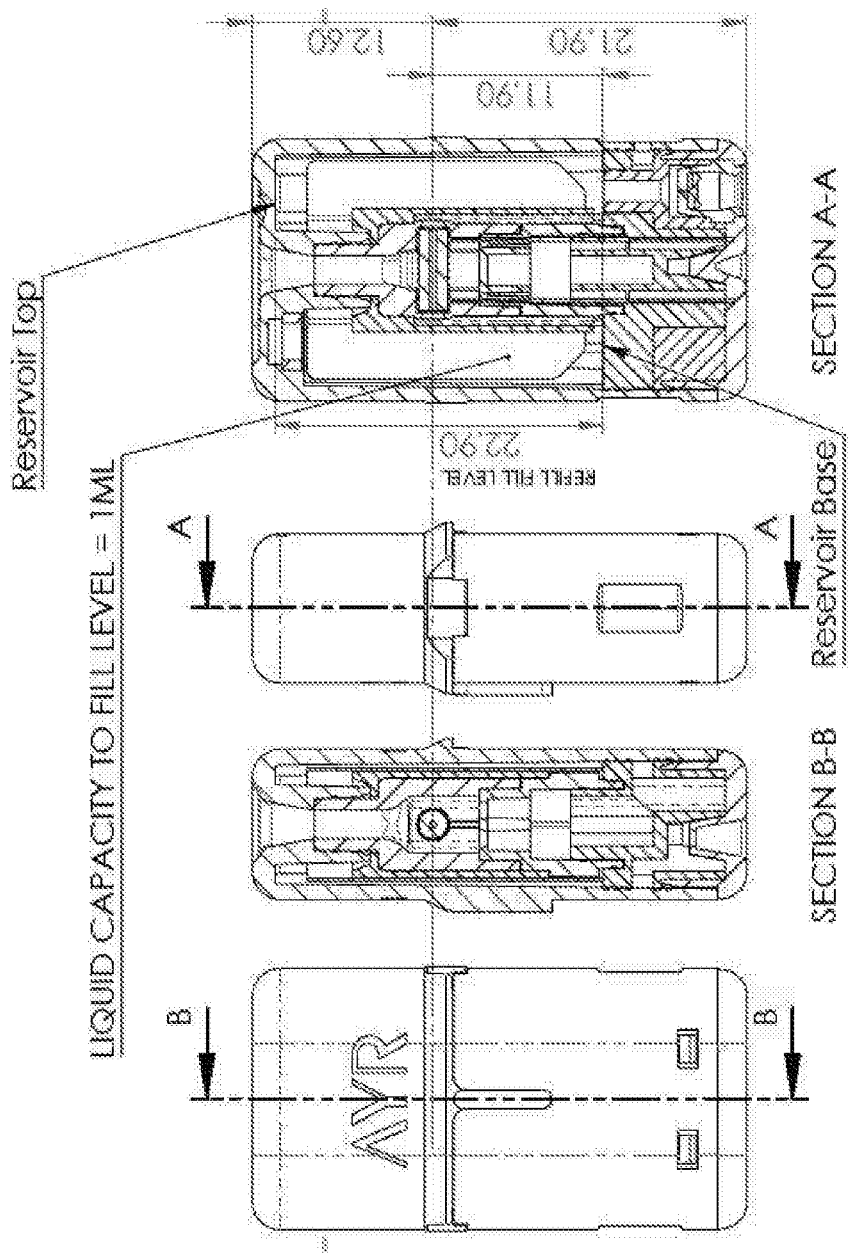
FIG. 15 are dimensioned, engineering drawings of the pod.

As noted above, the ceramic wick 115 is mounted in the upper silicone inner cylinder 120. The liquid channels 131 feed the ceramic wick with liquid. In a conventional pod, the atomising coil is placed at the base of the pod; this is undesirable with a refillable system because a refillable system needs a way to vent air from the reservoir as that reservoir is filled by a pump; that means some form of air valve or channel that fluidly connects to the external atmosphere for pressure equalisation. In FIG. 14, this is the air vent 142, sealed by an air-permeable but liquid impermeable barrier 143. But the presence of that air vent 142 or channel means that, if the wick is placed at the base, then normal static atmospheric pressure will tend to cause liquid to leak out from the reservoir, via the wick, and down through the base of the pod. In a conventional pod, this happens far less readily because there is no direct air vent to the liquid reservoir; as liquid is used up then a partial vacuum forms, tending to restrict liquid leakage. In the AYR system, we place the atomising element (e.g. wick 118 and coil 116, or any other atomising device is possible) at least mid-way vertically in the liquid reservoir. It is much closer to the mouthpiece opening or exit, which in turn gives warmer vapour. It is generally 10-15 mm from the end of the mouthpiece. It is approximately 20-25 mm up from the base of the pod and 10-15 mm up from the base of the liquid reservoir. FIG. 15 is an engineering drawing of one implementation, giving precise figures.

The liquid channels 131 at their base 141 are open to the bottom of the liquid reservoir and hence liquid readily enters the channels 131; when a user inhales, then the air pressure reduction in the channels 131 causes the liquid in the channels 131 to rise up and feed the ceramic wick 115, just as liquid can be drawn up a straw when sucked on. Once the user ceases to inhale, the pressure drops and the liquid drops back down the channels 131; this prevents continuous liquid contact with the wick 115, which can otherwise lead to liquid leakage through the wick 115 and out of the pod. Liquid is pumped into the reservoir through valve 112 and liquid stem 113 that leads directly to the base of the liquid reservoir.

Figure 16:
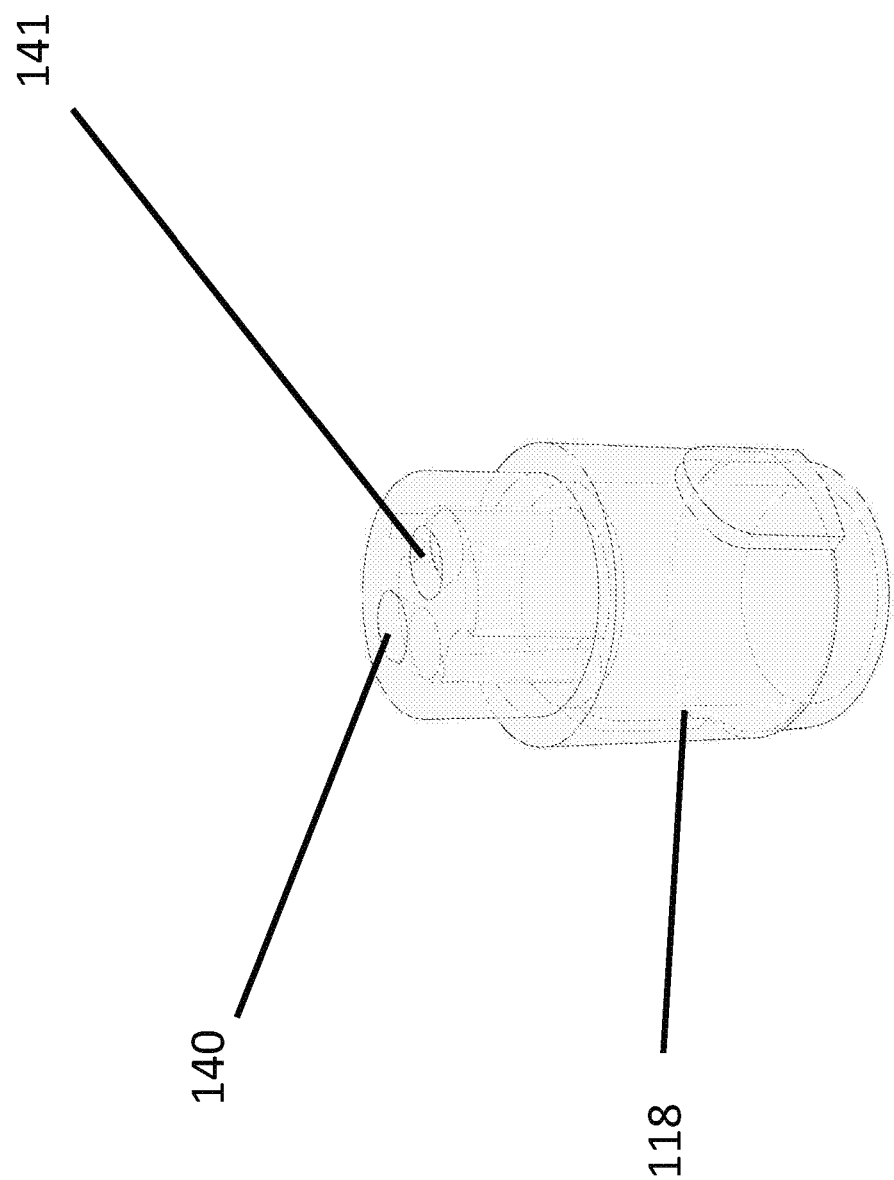
FIG. 16 is a perspective view of the internal part of the pod called the chimney, which directs a vortex of air towards the atomising unit.
Figure 17:
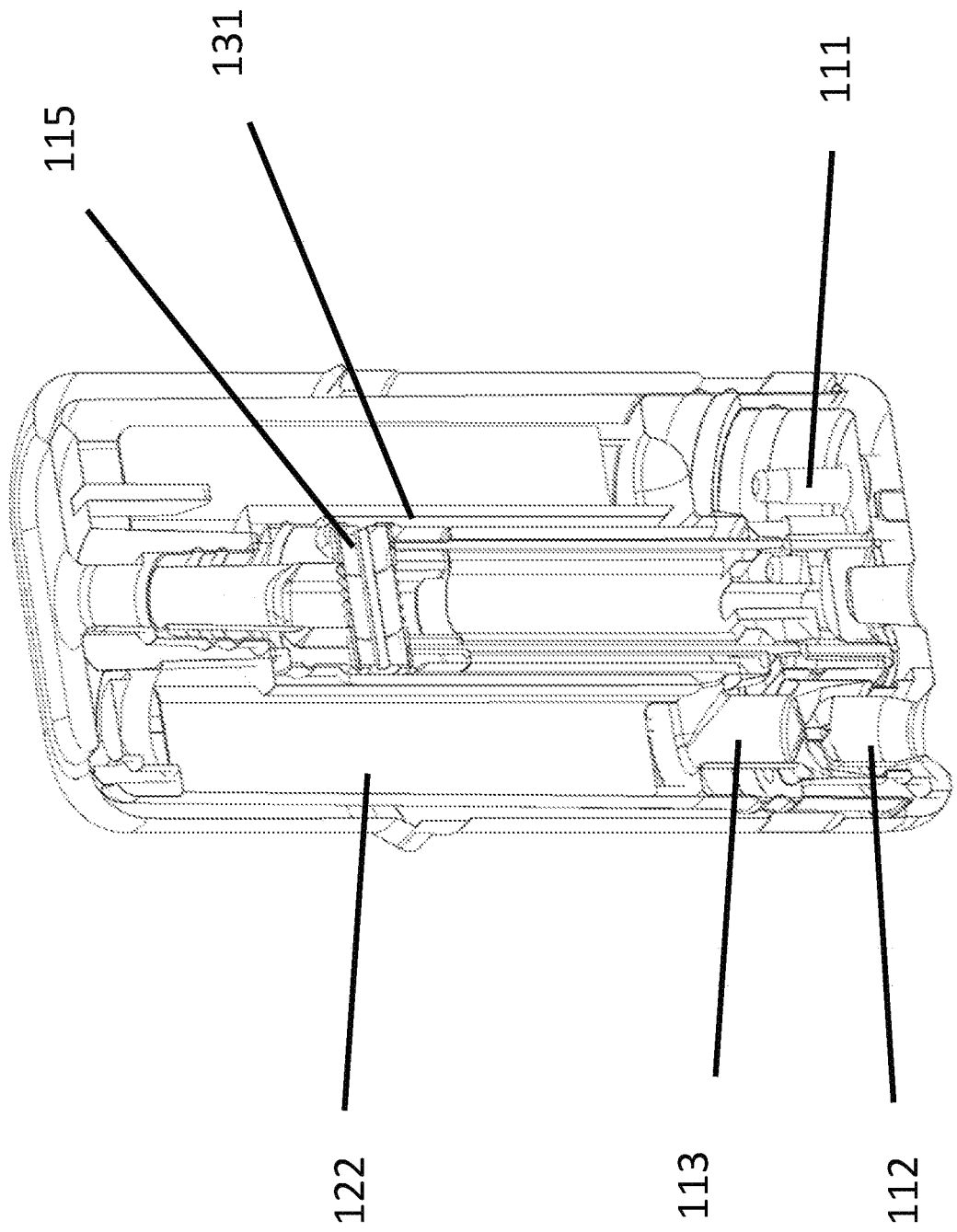
FIG. 17 is a cross-sectional view of the entire pod, showing how all the elements shown in the exploded view of FIG. 11 fit together.
Figure 18:
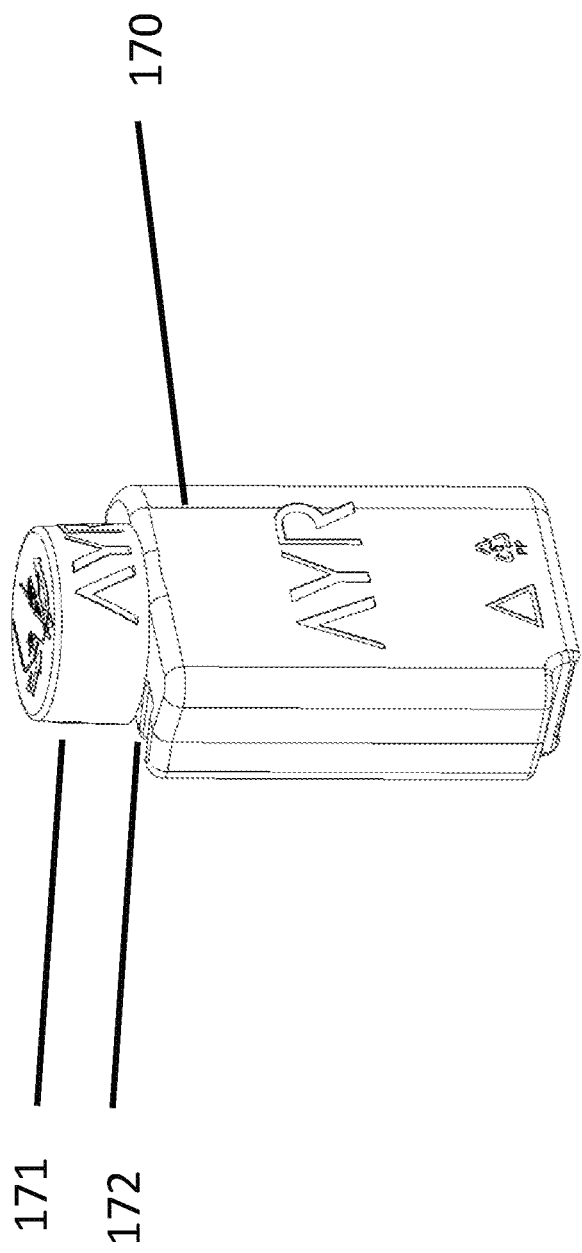
FIG. 18 is a perspective view of the refill liquid bottle that is inserted into the re-fill and re-charge case.
Figure 19:
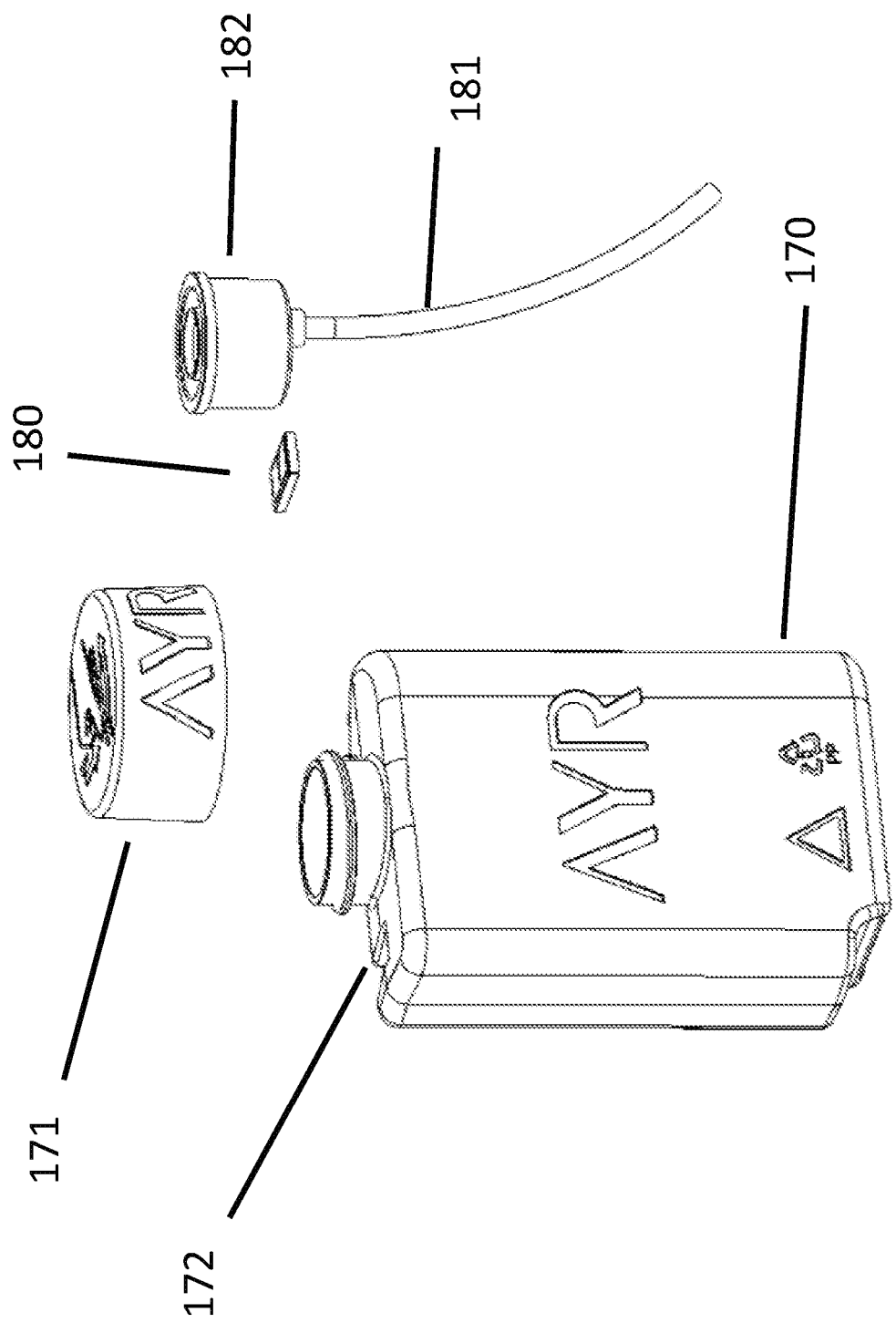
FIG. 19 is a perspective view of the refill liquid bottle, exploded to show the authentication chip, cap, bung and dip tube separate from the body of the bottle.

FIG. 16 shows the chimney 118 in more detail, including apertures 140 and 141. One aperture 140 directs air at approximately 45 degrees anti-clockwise to the vertical, seen from one position; the other aperture 141 directs air at 45 degrees clockwise to the vertical, seen from the same position. This cause the air to form a twisting vortex or other turbulent flow around the atomising coil, which leads to better vapour production (e.g. higher and more consistent aerosol production) and more even temperature distribution along the heating element, which minimises the risk of hot spots, and hence gives more predictable aerosol constituents and a much lower risk of contaminants that could otherwise be caused by localised hot spots on the heating element.

FIG. 16 shows another cross-section through the entire assembled re-fillable tip.

We will move on now to the re-fill bottle, shown in FIG. 18. This is typically 10 mL in liquid capacity, but that capacity is chosen to conform to EU regulations; in other markets, significantly larger refill bottles are possible, potentially delivering even greater value to consumers. The bottle has a body 170 that is an ultra-low cost blown plastic bottle. A child-proof screw cap 171 threads onto a short neck. On the bottle shoulder there is a moulded feature 172 that is designed for a small memory or chip to be snap-fitted into position or slid into position.

FIG. 19 is an exploded view; the bottle 170 includes a child-proof cap 171 which screws onto a very short threaded neck; unlike a conventional e-liquid filling bottle, there is no pouring spout or tapering projection from which a user can pour liquid; in the AYR system, liquid is only ever withdrawn automatically by a pump and the user does not ever manually pour liquid from the bottle. The bottle includes a crypto-chip or security authentication chip that is press fitted or slid into a small recess 172 in the top shoulder of the cap; the recess can have a dovetail shape so that the chip can be readily inserted and also extracted for when the bottle is being cleaned for re-use or re-cycled. Read and write to and from the chip can be implemented using a 1-Wire protocol with physical contacts in the device (e.g. the case or desktop dock or mod-type vaping device) the bottle 170 is inserted into.

Alternatively, wireless read and write to the chip may be implemented (e.g. using RFID). Wireless reading of data from the chip is especially useful for rapid reading of bottles in their packaging—for example, by regulators or agencies looking to check the provenance of the bottle and its contents; in a factory, distributor, retail outlet or with an end-user, an agent could using a wireless reding device scan all the packaged bottles, download all their data (e.g. unique number, batch number, liquid type) and write that data into a central database so that there is record of exactly what bottles are where; counterfeits can readily be identified since they will either have no RFID data tag or else the data on that tag will be a duplicate of an existing tag. The tag could also have written onto it a tax or customs stamp or evidence of duty having been paid; an agent can then rapidly scan bottles to verify that the correct duty has been paid. The same authentication chip can be used for pods too.

More specifically, the authentication chip stores a complete record of bottle filing date, liquid batch number for full traceability, and excise duty or tax payment, record. The record of excise tax payment can be a unique sequence generated by an excise payment system, tied to the liquid batch number, and written into the authentication chip at the time the pod or bottle is filled with liquid at the filling factory. The unique sequences are purchased by the device vendor (or pod or capsule vendor) from the relevant governmental body responsible for collecting excise duty for the market where the pod or bottle will be sold. The excise duty number can be hashed (e.g. with the liquid batch number) or otherwise encrypted to make counterfeiting difficult. The vaping device or dock can be programmed to be inoperable if a valid, authentic decrypted excise duty record is not present in the pod or refill bottle—i.e. the vaping device or dock implements a check-routine to decrypt and authenticate the excise duty record; it can also store a record of earlier excise duty records and work only if the excise duty record is unique and not present in that record. The authentication can be entirely local to the vaping device or dock—i.e. no communication to an external server is required. Where the vaping device or dock is connected to the internet, then it also use a remote authentication server, and share the excise data it has downloaded from the pod or re-fill bottle, so there is a central record of the use of excise-duty paid consumables, available to government bodies to review and audit. The authentication chip can be used for capturing excise payment on other vaping consumables: for example, on packets of the small tobacco sticks used in heat-not-burn devices, so that there is a single, uniform, global system for capturing excise duty on products designed to replace cigarettes. Providing a cost effective way of imposing or collecting tax duty on bottles of liquid and testing bottles for customs or tax compliance will become increasingly important as government tax revenues on cigarettes decline and it becomes fiscally necessary to start collecting taxes on vaping device and their related consumables, such as the liquid bottles or cartomisers.

The bottle includes a dip tube connected to an element we refer to as a 'bung' or other form of seal or stopper 182; the bung 182 sits inside the sole opening in the bottle 170, which is closed by the child-proof screw cap 171.

Figure 20:
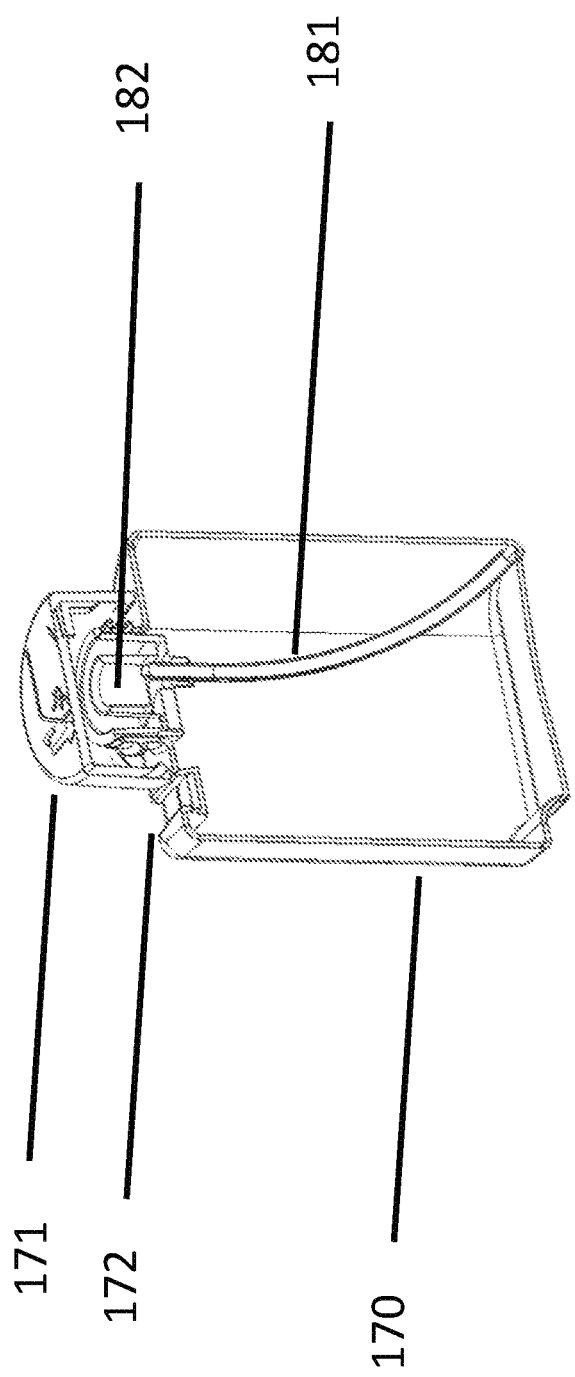
Figure 21:
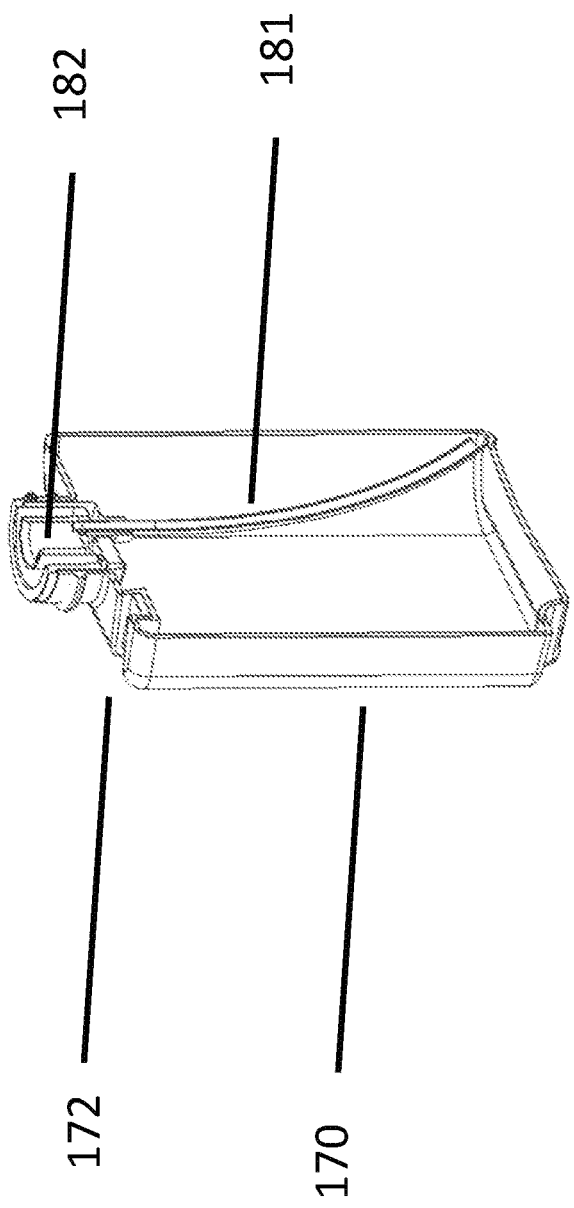
FIG. 21 is a cross-sectional view of the refill liquid bottle with the child-proof cap off.
Figure 22:
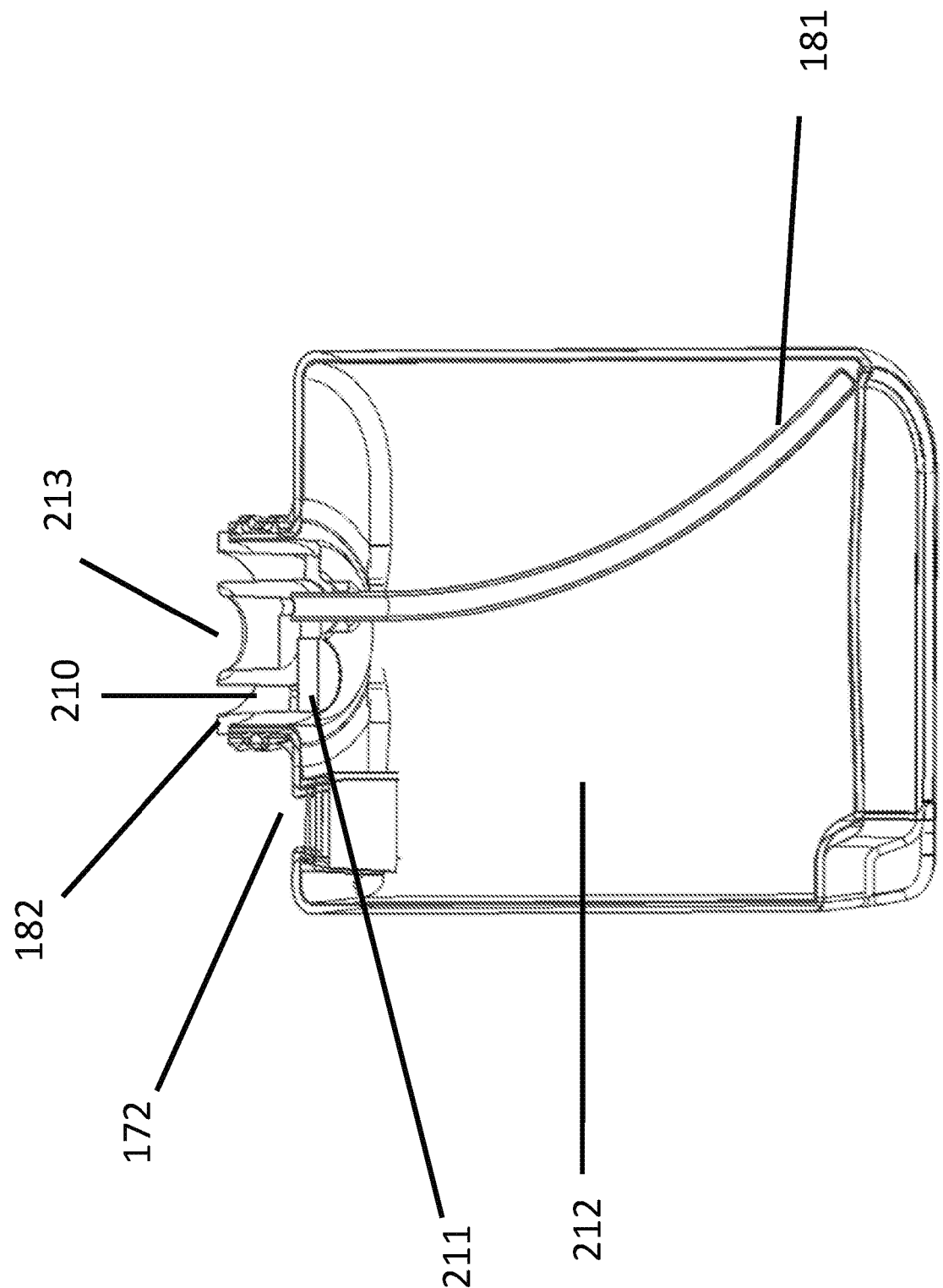
FIG. 22 is a further cross-sectional view of the refill liquid bottle with the child-proof cap off.

FIG. 20 is a sectional view through the bottle with the lid or cap screwed on. FIGS. 21 and 22 is a sectional view of the bottle with the lid or cap removed, as it would be when the bottle is positioned in the AYRCase, AYRDock or AYRMod device. The dovetail shape of the crypto-chip recess 172 is clearly visible, as is the structure of the bung.

The bung 182 is cylindrical and sits within the short neck of the bottle; it includes an outer annulus section 210 through which air can pass into and out from the interior 212 of the bottle for pressure equalisation; the lower face of the annulus 210 is sealed with a membrane 211 made of a material like PTFE that is air-porous but is impermeable to the liquid. Air needs to pass into the bottle interior 212 as liquid is withdrawn from it via the dip tube 181 by the pump during normal operation, since otherwise a partial vacuum will form, making it impossible to pump liquid from the bottle.

During filling of the bottle with liquid at manufacture time, a conventional liquid filling rig, e.g. as typically used for high speed filling of e-liquid bottles, can be used to pour liquid through the neck of the bottle; without the bung 182 in position. After filling, the bung 182 is then pushed into the bottle and the child-proof cap 171 screwed on. This enables fast and efficient bottle filling with minimal modifications to existing e-liquid filling manufacturing lines.

When the bottle is in position in the case, dock or vaping device, a nozzle in the case or dock fits snugly into the central bore 213 of the bung 182 and over the entrance to the dip tube 181; the nozzle is connected to the pump in the case, dock or device, so that when the pump is activated, liquid is withdrawn up the dip tube 181, through the central bore and then into the nozzle of the device.

Figure 23:
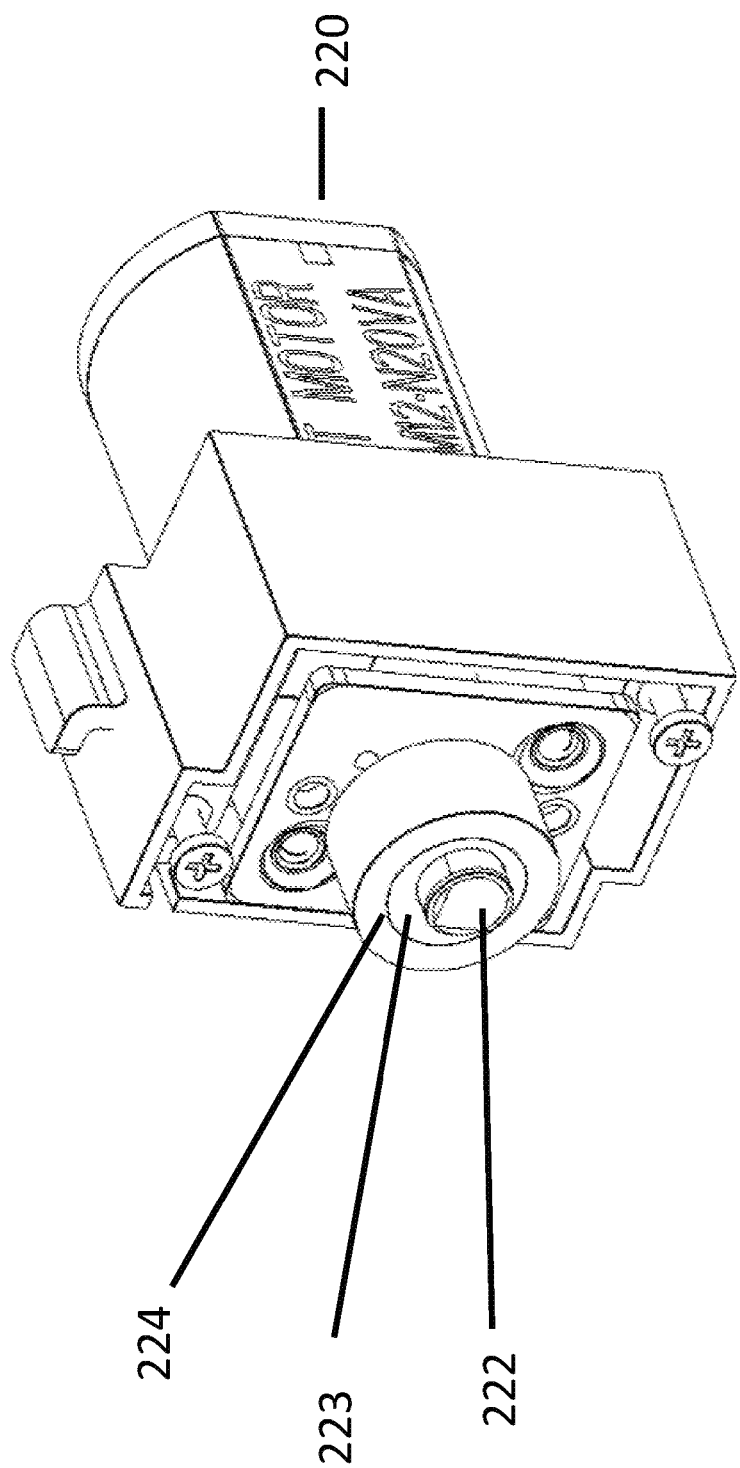
FIG. 23 is a perspective view of the motor and peristaltic pump.
Figure 24:
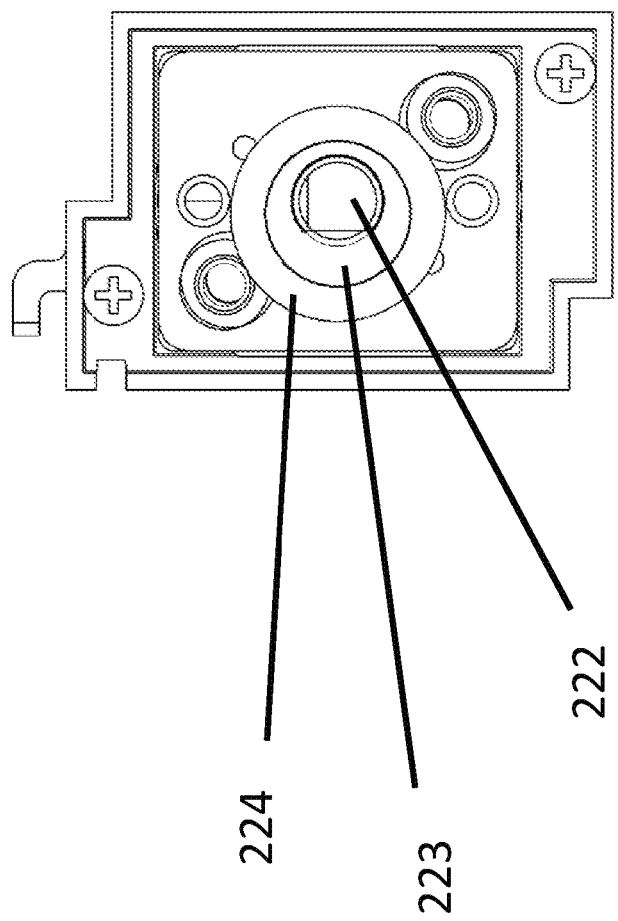
FIG. 24 is a frontal view of the motor and peristaltic pump.
Figure 25:
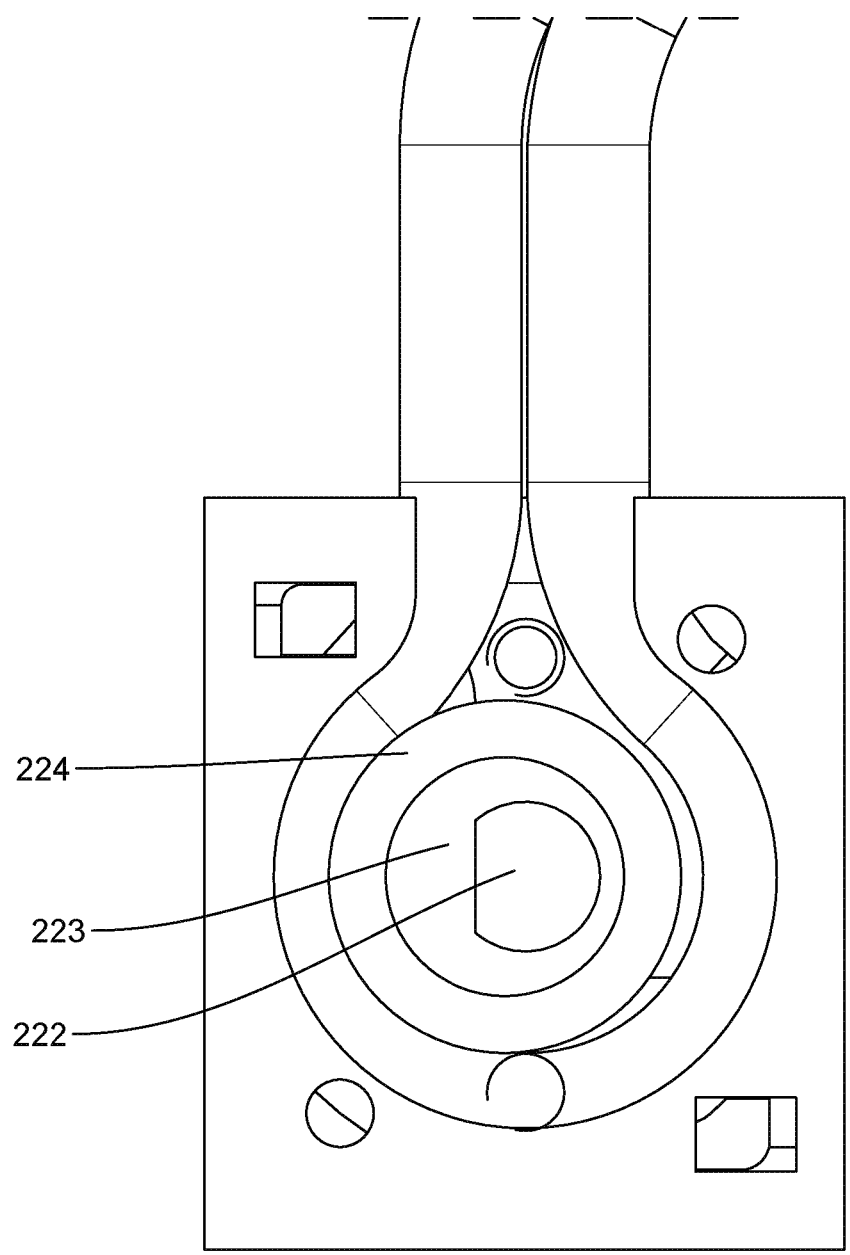
FIG. 25 is a frontal view of the motor and peristaltic pump including the liquid tubing.

FIG. 23 shows a perspective view of the motor 220 used to drive the peristaltic rotor; the liquid tubing (not shown) that connects to the nozzle that in turn engages with the liquid refill bottle, is passed over a portion of the rotor; as the rotor rotates, it moves liquid through the tube using peristaltic movement, from the bottle and into the liquid reservoir of the vaping device re-fillable pod or tip. The rotating shaft 222 of the motor has mounted on it an annulus 223 with an eccentric shape; the outer surface of the eccentric annulus 223 is a low friction surface, contacting a low friction surface of an outer circular annulus 224. FIG. 24 is a front-on view of this system; FIG. 25 includes the peristaltic tubing. As the motor shaft 222 and eccentric annulus 223 rotate, the outer circular annulus 224 moves laterally but does not rotate; a food-grade peristaltic tube (that has been tested to ensure that it is minimally impacted by nicotine or e-liquid) runs around a section of the outer circular annulus 224 and the lateral movement presses in the tubing; as the most eccentric portion of the inner annulus rotates, then the surface of the circular annulus that sits over that most eccentric portion is pushed radially outwards; this portion rotates and as it does so, it causes peristaltic compression of the tubing, forcing liquid to move along the tubing. The movement is fully reversible to extract liquid from the vaping device and the re-fillable pod and pump it back into the refill bottle; this is useful when changing flavours since it minimises flavour mixing.

We can summarise some of the key features as follows:
High Coil

For a refillable, user-replaceable tip or pod or cartomiser, we have found that the conventional placement of the atomising unit at or close to the base of the tip is problematic because the tip has to vent to the atmosphere for pressure equalisation during filling with liquid, and consumption of liquid from normal vaping; because the atomising unit typically includes a wick that is gravity or capillary fed liquid from a liquid reservoir in the tip, atmospheric pressure on the surface of the liquid in the liquid reservoir and the and hydrostatic pressure of that liquid is sufficient to overcome any surface tension effects that would otherwise limit the flow of liquid through the wick and into the atomising chamber, and from there into the base of tip or the inhalation chamber, from which it can readily leak out. We have found that the solution is to move the coil up from the base to a sufficient vertical height in the tip so that leakage through the wick caused by atmospheric pressure on the liquid and hydrostatic pressure of that liquid in the liquid reservoir does not arise. For example, if the liquid reservoir is typically filled to a height of x cm above the base of the tip, then we position the wick that feeds the atomising unit to minimise the vertical distance between this wick position and the normal maximum fill level of the reservoir; for example, we can position the wick itself at about x cm from the base too. Different wicking behaviour, wick geometries, and atomiser geometries (whether including a wick or wickless) will determine the optimal positioning.

We can generalise as follows:

A vaping device including an automatically re-fillable liquid reservoir that includes an air pressure equalisation pathway to the external atmosphere, and an atomising unit configured to draw liquid from the reservoir;
  in which the atomising unit is positioned in relation to the surface of the liquid in the reservoir when the reservoir, oriented vertically, contains a maximum of liquid, such that pressure exerted on and/or by the liquid is not sufficient to cause liquid to flow through the atomising unit and cause liquid leakage.

Some optional features:
pressure exerted on and by the liquid is due to atmospheric pressure acting on the surface of the liquid and hydrostatic pressure of the weight of the liquid.
the atomising unit is placed, at least in part, at or above the surface of the liquid in the reservoir when the reservoir contains a maximum of liquid, when the device is oriented vertically.
the atomising unit includes a liquid path that enables liquid from the liquid reservoir to leak out to the surface of a pod containing the atomizing unit and liquid reservoir, and the atomising unit is placed at a vertical position in relation to the liquid reservoir such that pressure exerted on and/or by the liquid at any point of the liquid path is not sufficient to cause liquid to flow through the liquid path and cause liquid leakage.

the liquid path in or through the atomizing unit is arranged substantially at or above the surface of the liquid in the reservoir when the reservoir contains a maximum of liquid, when the device is oriented vertically, such that pressure exerted on and/or by the liquid at any point of the liquid path is not sufficient to cause liquid to flow through the liquid path and cause liquid leakage.

the liquid path in or through the atomizing unit is arranged sufficiently near to the surface of the liquid in the reservoir when the reservoir contains a maximum of liquid, when the device is oriented vertically, such that pressure exerted on and/or by the liquid is not sufficient to cause liquid to flow through the liquid path and cause liquid leakage.

the atomising unit is placed at least in part below the surface of the liquid in the reservoir when the reservoir contains a maximum of liquid, but still at least 90% of the vertical height of the liquid in the reservoir when the reservoir contains a maximum of liquid, when the device is oriented vertically.

the atomising unit is placed at least in part below the surface of the liquid in the reservoir when the reservoir contains a maximum of liquid, but still at least 75% of the vertical height of the liquid in the reservoir when the reservoir contains a maximum of liquid, when the device is oriented vertically.

the atomizing unit includes a wick and the wick is placed, at least in part, at or above the surface of the liquid in the reservoir when the reservoir contains a maximum of liquid, when the device is oriented vertically.

the atomising unit includes a wick and the lowest portion of the wick is placed at or above the surface of the liquid in the reservoir when the reservoir contains a maximum of liquid, when the device is oriented vertically.

The liquid reservoir and atomizing unit are formed in a tip or pod that is user-replaceable and slides in or other engages with a vaping device body.

We can also look at this in structural, as opposed to functional, terms, using the base of the liquid reservoir as the baseline:

A vaporising device including an automatically re-fillable liquid reservoir of maximum vertical liquid height H, measured from the base of the liquid reservoir, and an atomising unit configured to draw liquid from the reservoir; in which the atomising unit is placed substantially higher or above the base of the reservoir, when the device is positioned vertically, at a position of at least ¼H up from the base of the reservoir.

Some optional features:

The atomising unit is placed at a position of at least ⅓H up from the base.

The atomising unit is placed at a position of at least ½H up from the base.

The liquid reservoir and atomizing unit are formed in a tip or pod that is user-replaceable and slides in or other engages with a vaping device body.

Atomiser that is Positioned Close to the Mouthpiece

One consequence of moving the atomising unit up from its traditional position at the base of a pod or tip is that it is now much closer to the mouthpiece. This in turn can lead to warmer vapour, which is generally more satisfying to a smoker looking to use a vaping device to quit smoking.

We can generalise as follows:

A vaporising device including an automatically re-fillable liquid reservoir and an atomising unit configured to draw liquid from the reservoir and to provide an aerosol to a mouthpiece; and in which the atomising unit mid-point or centre is positioned less than 20 mm from the end of the mouthpiece, and preferably between 10 mm and 15 mm from the end of the mouthpiece.

Siphon Tubes

One challenge the AYR engineers faced when moving the atomising unit up from the base of the tip was how to feed liquid into the atomising unit; atmospheric pressure on the liquid surface or hydrostatic pressure/gravity combined with capillary action of a wick is normally sufficient for a conventional tip design, since the wick and atomising unit is normally at the base of the pod or cartomiser. In AYR, the liquid feed path would have to prevent excessive liquid moving into the atomising unit, which would lead to leakage, and yet also prevent inadequate quantities of liquid moving into the atomising unit, since that would give a poor vaping experience.

The solution reached was to use one or more narrow liquid feed channels that lead from the base of the liquid reservoir up to the wick; these are sufficiently restricted in cross-sectional area such that the ordinary act of inhaling on the device mouthpiece, which causes negative pressure (negative relative to atmospheric) in the atomising chamber, and hence negative pressure in the wick that leads to the atomising chamber, is enough to cause the liquid in the feed channels to rise up and contact and enter the wick, and hence enter the atomising chamber, even when the liquid level in the liquid reservoir is low or the reservoir is held horizontally. We may call this a siphon, in the broad sense of a siphon meaning any system where liquid flows through tunes. (In the narrow sense, a siphon can be thought of as a combination of atmospheric pressure pushing liquid up a tube, and we have that in the AYR system, and then gravity pulling it down to a level below the level in the source, which we do not have). The operation is in fact more similar to sucking liquid up through a straw.

We can generalise as follows:

A vaporising device including an automatically re-fillable liquid reservoir and an atomising unit configured to draw liquid from the liquid reservoir and to provide an aerosol to a mouthpiece, and in which the liquid reservoir connects to the bottom of one or more liquid channels and the atomising unit connects to the top of the or each channel, each channels being configured such that when a user inhales on the mouthpiece, air pressure reduction causes liquid to flow up the or each channel and into the atomising unit.

Some optional features:

When the user stops inhaling, then the liquid ceases to flow up the or each channel.

Each channel connects to the liquid reservoir at the base of the liquid reservoir.

The length or cross-sectional area of each channel is selected to provide adequate liquid transport into the atomising unit whilst minimizing liquid leakage from the mouthpiece.

The liquid reservoir includes an air permeable, liquid impermeable membrane that vents to the external atmosphere.

The liquid reservoir, atomizing unit, mouthpiece and channels are formed in a tip or pod that is user-replaceable and slides in or other engages with a vaping device body.

The atomising unit includes a ceramic wicking element that is horizontally arranged when the tip is upright.

each channel is formed as a groove in one generally cylindrical member that press or friction fits inside a larger, generally cylindrical member.

the atomising unit is placed at a vertical position in relation to the surface of the liquid in the reservoir when the reservoir, oriented vertically, contains a maximum of liquid, such that atmospheric pressure acting on the surface of the liquid is not sufficient to cause liquid to flow through the atomising unit and cause liquid leakage.

the atomising unit is placed substantially higher or above the base of the reservoir, when the device is positioned vertically, at a position of at least ¼H up from the base of the reservoir.

The liquid reservoir, atomizing unit, mouthpiece and channels are formed in a re-fillable tip or pod that is user-replaceable and slides in or other engages with a vaping device body.

Turbulent Flow

Another challenge the AYR engineers faced when moving the atomising unit up from the base of the tip was that the air moving up to the atomising unit would be flowing up a path that is significantly longer than in a conventional cartomiser pod; in a conventional pod, the atomising unit is usually placed at the base of the pod and hence very close to the start of the air inlet path. The problem with extending the length of the air flow path is that it increases the likelihood and extent of laminar air flow; laminar air flow over an atomising unit is undesirable because it leads to areas on the heating surface with limited contact with moving air; moving air is not evenly distributed over the heating surface. This can lead to hot spots on the heating surface that are higher than desirable; excessive temperatures even in highly localised areas can lead to undesirable by-products or contaminants forming in the vapour. In the AYR atomising unit, we use a specific mechanism to introduce turbulent flow; the air flowing up a 'chimney' to the atomising unit hits one or more nozzles or apertures at the top of the chimney that are configured to direct the laminar air into a turbulent pattern, or a vortex.

We can generalise as follows:

A vaporiser including an atomiser and an air supply nozzle system configured to direct air, sucked through the vaporiser, onto the atomiser, in which the air supply nozzle system includes one or more nozzles or apertures configured to direct air not substantially vertically up towards the atomizer, when the vaporizer is in an upright position, but instead at an angle or direction that is angled to the vertical in order to create a substantially non-laminar, turbulent, twisting or vortex flow of air over the atomiser.

Some optional features:

Each nozzles or aperture is configured so that air leaves the nozzle or aperture. angled at least 5 degrees to the vertical axis through the atomiser.

Each nozzles or aperture is configured so that air leaves the nozzle or aperture angled at least 10 degrees to the vertical through the atomiser.

Each nozzles or aperture is configured so that air leaves the nozzle or aperture angled at least 20 degrees to the vertical through the atomiser.

Each nozzles or aperture is configured so that air leaves the nozzle or aperture angled at least 30 degrees to the vertical through the atomiser.

Each nozzles or aperture is configured so that air leaves the nozzle or aperture angled at least 40 degrees to the vertical through the atomiser.

Each nozzles or aperture is configured so that air leaves the nozzle or aperture angled at least 50 degrees to the vertical through the atomiser.

There are at least one pair of nozzles or apertures, each nozzle being laterally displaced from a line defining the middle of the atomizer and configured to direct air in a direction opposite to the other nozzle, so that air forms a vortex flowing around the atomizer.

The air supply nozzle system sits over an air chimney or stack which supplies air flowing in a non-turbulent, or substantially laminar manner to the air supply nozzle system.

The atomiser is placed in an air chimney that supplies air with significant laminar flow properties.

The atomiser and nozzles or apertures are formed in a re-fillable or pre-filled tip or pod that is user-replaceable and slides in or other engages with a vaping device body.

PET Covered Channel

A complex vaping device like AYR is potentially quite costly and difficult to manufacture; cost reduction is an ever-present requirement. The normal way one would transfer liquid up through a vaping device, from an inlet aperture that connects to a pump (which is external to the vaping device in the AYRBase and AYRCase variants, and internal to it in the AYRMod variant) is through a dedicated pipe. But the space available for a pipe is very limited and so the pipe has to be very narrow and made to high tolerances; and bends in the pipe are difficult to manufacture, so that imposes design constraints. In the AYR vaping device body, we use the plastic moulding that forms the internal chassis to which the battery, circuit board and other major components are fixed; we form a narrow channel in that moulding. That channel forms three sides of the liquid channel path up through the vaping device. A clear plastic film is ultrasonically welded to form the cover to the channel, in a manner used in a different, non-analogous situation, namely transporting liquid ink in an inkjet printer cartridge a short distance from an ink reservoir to the inkjet printing head. The channel need not be straight but can twist; this is readily done in a plastic moulded part. This gives us a fluid transfer path that is very cheap to make, leading to reduced cost of goods, and is reliable.

We can generalise as follows:

A vaporising device that includes (i) a liquid reservoir supplying liquid to an atomizer; (ii) a port, aperture or nozzle configured to enable the device to be filled with atomisable liquid from a liquid source and (iii) a liquid path connecting the liquid reservoir to the port, aperture or nozzle; and in which the liquid path includes a channel covered with a plastics film.

Some optional features:

Channel side(s) are formed from the chassis or other components that are integral to the vaping device body.

Channel side(s) are formed from the plastic moulded chassis of the vaporizing device.

Film is PET.

Film is ultrasonically welded to the channel sides.

Channel includes one or more changes of direction.

Capsule or Bottle Features

Fast Fillable Bottle

In the preceding section, we described how the AYR design reduces the cost of goods for the vapourising device. The same imperative exists for reducing the cost of goods of the re-fill liquid bottle; the imperative is even greater for the bottle since it is the primary consumable in the AYR system and a typical consumer will purchase twenty or more re-fill bottles for every vaping device.

One critical element for the re-fill bottle is ensuring that it enables fast and efficient filling with liquid at the liquid filling factory; and does so with a cheap and easy to manufacture structure that is readily recycled. With AYR, the refill bottle, typically 10 mL in capacity, is a very low cost blow-moulded bottle with a short threaded neck; the mouth permits permit a nozzle connected to an automatic liquid filling system to be inserted or used to pour liquid into the bottle; no costly modifications to industry standard liquid filling factories are needed. Once filled, a structure we refer to as a 'bung' is inserted into the neck; this is specially configured to engage with the liquid re-filling system in the vaping device or dock or case. More specifically, the bung is a single moulding that enables two distinct functions; it has a central aperture that receives an e-liquid nozzle connected to the liquid pump; that central aperture is connected to a dip tube that passes down to the base of the bottle and ensures that all liquid in the bottle can be pumped out. Surrounding the central aperture in the bung is an annular aperture through which air can pass in and out of the bottle, enabling rapid pressure equalisation to atmospheric pressure; a liquid impermeable but air permeable barrier closes off one face of the annular air channel.

We can generalise as follows:

A liquid re-filling bottle with a mouth being configured to (i) permit a nozzle connected to an automatic liquid filling system to be inserted, or otherwise used, to pour liquid into the bottle through the mouth when the bottle is being filled at a filling factory and (ii) receive a bung or seal that is configured to both engage with a fluid transfer system and also permit air pressure equalisation within the bottle.

Some optional features:

Bung is made from a single moulding.

the bung includes a first aperture configured to receive a liquid filling nozzle from a re-filling system to withdraw liquid from the bottle, and a second aperture that is configured to enables air to pass in and out of the bottle during filling or emptying of the bottle for air pressure equalisation within the bottle.

The first aperture is an inner channel or opening.

The nozzle friction fits into the first aperture.

The second aperture is an outer channel.

The outer channel is concentrically arranged around the inner channel.

The second aperture includes an air vent that is permeable to air but impermeable to e-liquid.

The first aperture is connected to a dip tube.

the bung includes a first nozzle configured to engage with a liquid filling aperture that is part of a re-filling system, to withdraw liquid from the bottle, and a second nozzle or aperture that is configured to enables air to pass in and out of the bottle during filling or emptying of the bottle for air pressure equalisation within the bottle.

The first nozzle is an inner nozzle.

The first nozzle friction fits to engage with a liquid filling aperture that is part of a re-filling system.

The second nozzle or aperture is arranged to surround the inner nozzle.

The second nozzle or aperture is concentrically arranged around the inner nozzle The second nozzle or aperture includes an air vent that is permeable to air but impermeable to e-liquid.

During filling with e-liquid at manufacture time, liquid is poured or pumped into the bottle through the bottle mouth and the bung is then fitted to the bottle, and then a child-proof lid is then fitted to the bottle.

Bottle is a blown plastic bottle.

Bottle is not user-refillable.

Bottle is substantially rigid.

The bottle includes a neck that defines the mouth, and the neck is a threaded neck configured for a screw-on child-proof cap.

Dual Use Liquid Filling Bottle

The AYR bottle is a rigid blow moulded bottle. It is designed exclusively to work with an AYR automated liquid refilling system. However, so-called open tank systems remain very popular; these require a liquid refill bottle that a user can position over an open atomiser, or engage with a filling nozzle in the vaping device, and simply squeeze to manually drip or pump liquid into the device. The AYR bottle can be modified so that it can also be used to fill an open tank system; it then needs to have flexible walls as opposed to rigid walls.

We can generalise as follows:

A flexible-walled liquid filling bottle that is configured to be both (a) manually squeezable to enable a consumer to manually deliver liquid to a reservoir in a vaping device and (b) received in a vaping system and connected to a pump in that vaping system that automatically pumps liquid from the bottle into a liquid reservoir that fees liquid to an atomising unit.

Bottle with Dovetail Recess for a Security or Data Chip

One major advantage of the AYR system is that the main consumable, the re-fill bottle, is recyclable. Since potentially tens of millions of these bottles may be made, recyclability is critical. One feature that could make recycling difficult is the presence of a small authentication chip or memory, which may be cryptographically secure; this memory device which stores various items of data (e.g. match number, date of manufacture, type of liquid, a counter that counts down each time a defined quantity of liquid is pumped out of the bottle). This would normally be bonded into position, but that presents problems when it comes to recycling, including cleaning the bottle for re-use. In the AYR re-fill bottle, a specially shaped channel receives the memory device and secures it mechanically within the channel; it can then be pressed out from the bottle to enable recycling. The channel could be a simple dove-tail shaped recess into which a standard memory chip can be readily slid or pressed; when the bottle is returned for recycling, the memory device can then be readily slid or pushed out of the recess and itself separately recycled.

We can generalise as follows:

A liquid re-filling bottle configured to engage with a fluid transfer system in a vaping system, the bottle including a section or recess into which an authentication chip or other authentication memory component can be physically inserted and then retained by the shape of the section or recess until physically removed to enable the bottle to be re-cycled.

Some optional features:

Section is a dovetail section and the component is slid into the section.

The component is secured in position in the section or recess without any glue or other chemical bonding.

The chip or component stores data defining the liquid contents of the bottle.

The chip or component stores data that defines temperature dependent characteristics of the substance.

The chip or component stores data relating to the number of times liquid has been withdrawn from the bottle, or the amount of liquid that has been withdrawn from the bottle, to prevent the bottle from being useable if filled by an end-user.

Chip uses an EEPROM emulation mode that irreversibly decrements a counter.

Spout Pouch

Figure 35:
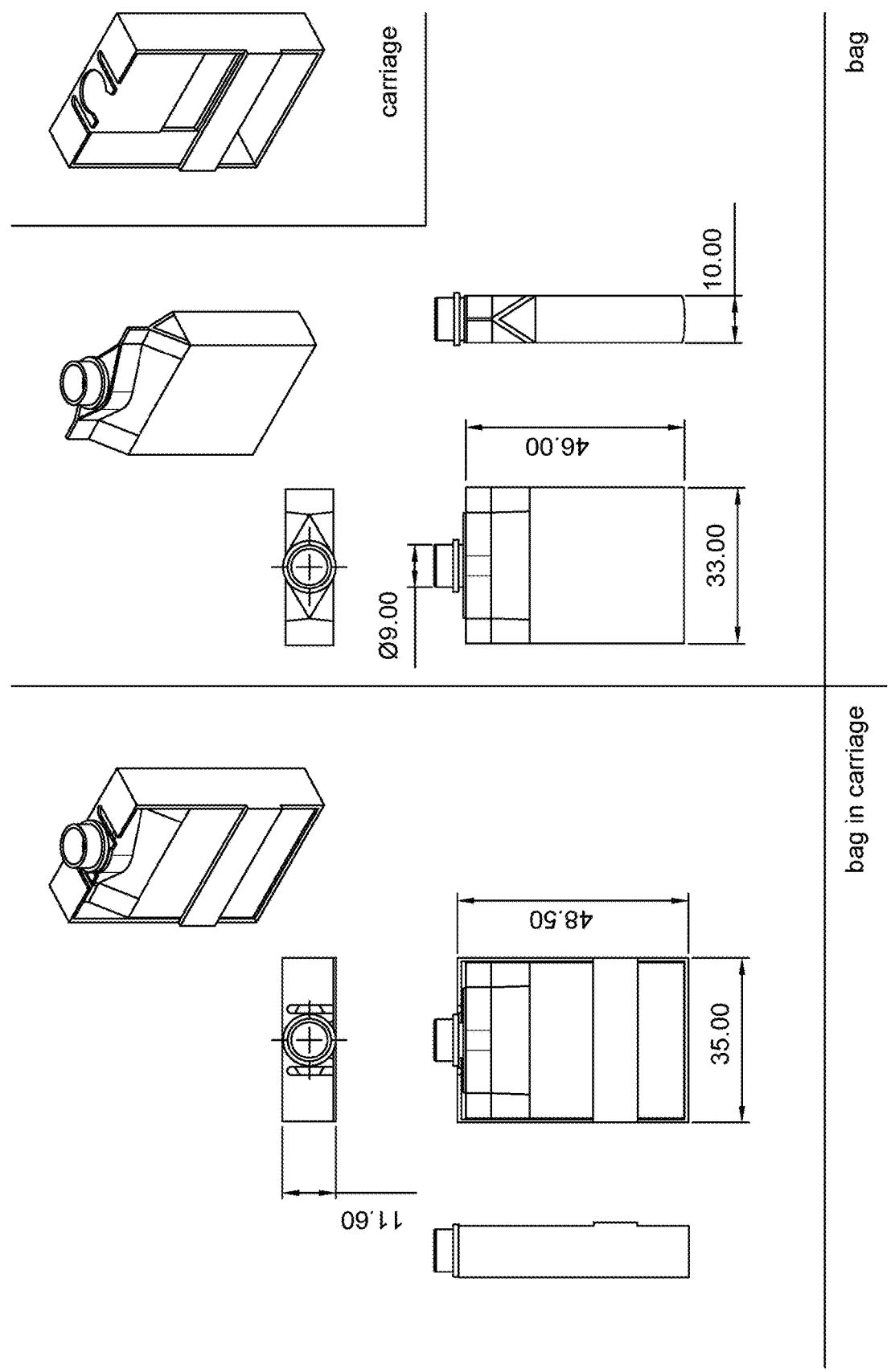
FIG. 35 shows various views of a soft pouch design of liquid refill bottle.

The bottle described above is hard plastic bottle. Another approach is to use a spout pouch configured to store nicotine e-liquid or CBD or THC liquid. Soft pouches are used for other foods and liquids, but their use for nicotine e-liquid or CBD or THC liquid is not established. FIG. 35 shows the soft pouch with short pouch; the soft pouch can be mounted in a plastic carriage; the filling dock or case includes the carriage, which a user slides out of the dock or case and then slides the soft pouch into the carriage, locking a recess or channel running around the spout or neck of the soft pouch with a feature or ridge in the carriage; this ensures accurate alignment of the spout, when the carriage is slid back into the dock or case, with the nozzle in the dock or case that is connected with the fluid transfer system.

We can generalise as follows:

A pouch made of a flexible barrier film or films and including a spout configured to engage with a fluid transfer system in a vaping system.

Some optional features:
- The pouch is completely filled at the point of filling with liquid leaving substantially no air within the spout pouch.
- The pouch is a stand-up spout pouch.
- The pouch is configured to engage with a carriage that is part of an atomising system, where the carriage receives the pouch.
- The pouch connects directly to a fluid transfer system configured to automatically extract liquid from the pouch and transfer that liquid to a reservoir for an atomizing system.
  - fluid transfer system is configured to automatically extract both fluid and also any air from the pouch.
  - fluid transfer system pumps air out of an air-permeable membrane or device that forms part of or is in air-communication with, the atomizing system.
- the pouch stores data (e.g. in a chip or barcode or QR code etc.) that define temperature dependent characteristics of the substance (e.g. e-liquid, CBD) in the pouch.
- The pouch includes a silicone bung inserted after filling and that permits liquid to flow out from the pouch and prevents air from passing back into the pouch.
- The pouch or spout-pouch stores e-liquid or CBD and is vacuum sealed.
- The pouch or spout-pouch stores e-liquid or CBD and includes a chip using an EEPROM emulation mode that irreversibly decrements a counter.
- The fluid transfer system includes a valve that stops or limits air passing back into the pouch or spout-pouch.
- The valve is part of a pump that operates to pump liquid from the pouch or spout-pouch, such as a roller or rotor for a peristaltic pump.

B. Software/Electronics

Figure 26:
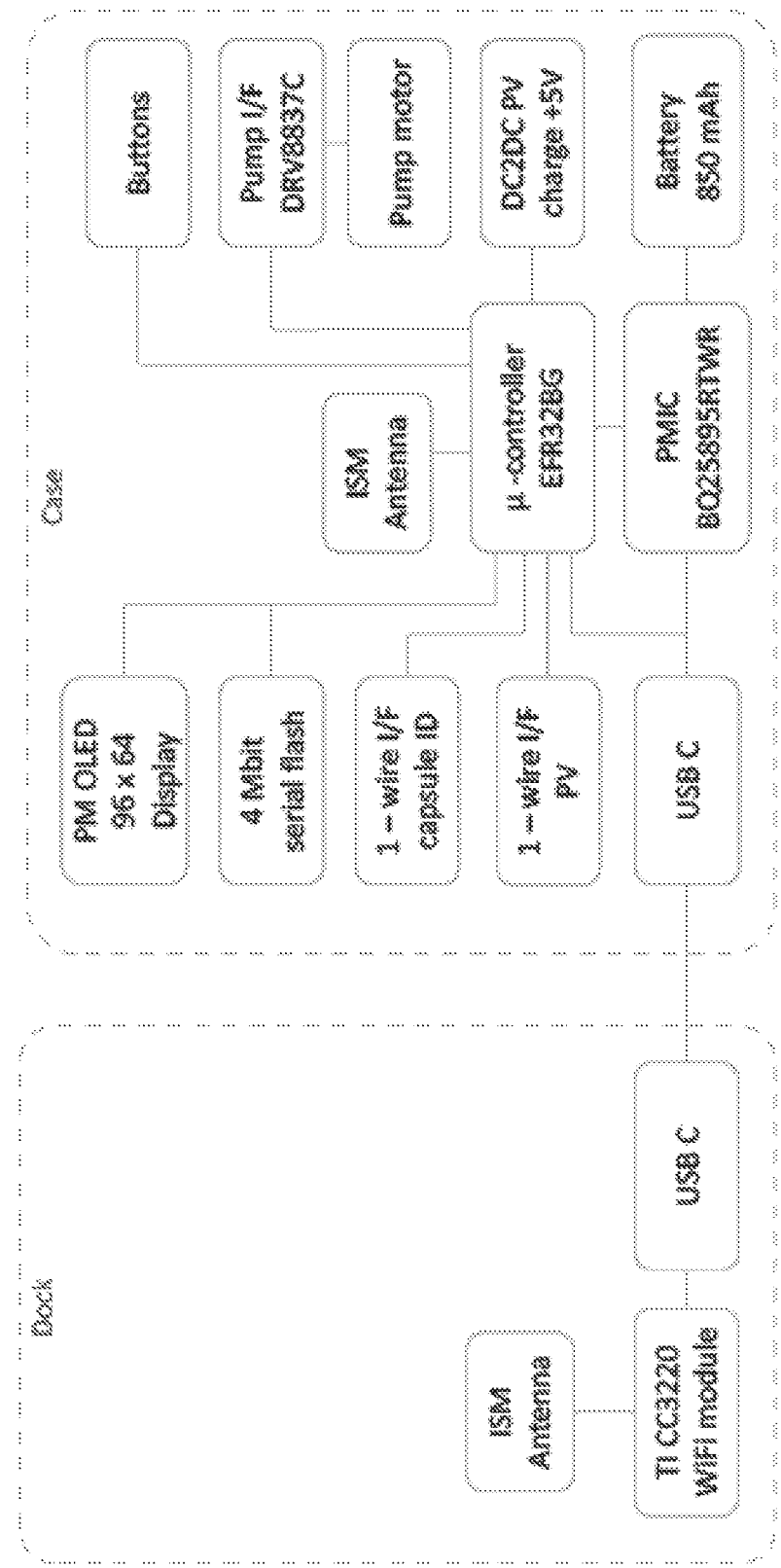
FIG. 26 is a schematic of the electrical and electronic components in the re-fill, re-charge case and the Wi-Fi dock it slots into.
Figure 30:
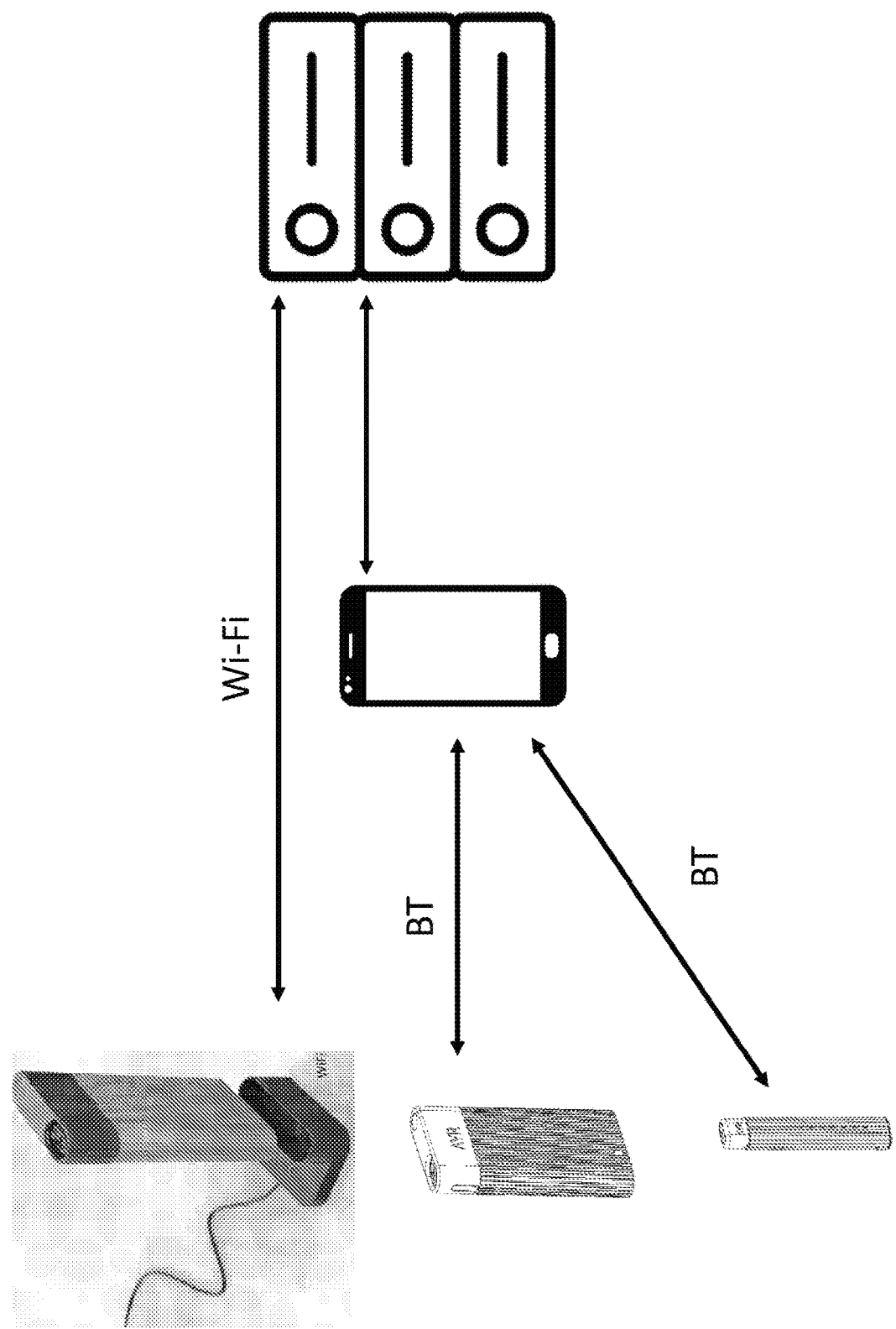
FIG. 30 is a perspective view of the re-fill and re-charge case over the Wi-Fi dock it slots into and the general data connectivity schemes available.

FIG. 26 is a schematic block diagram of the key electronic components in the re-fill and re-charge case (AYRCase) and a Wi-Fi dock that the case sits on. FIG. 30 shows the external appearance of the case and the Wi-Fi dock and the data connectivity scheme. The Wi-Fi dock reads data from the vaping device and refill bottle and sends that over a local Wi-Fi link and then over the internet to a remote server; the remote server implements various functions, such as age verification and data analytics. A user's smartphone can display data, such as nicotine useage data, especially useful if working towards nicotine cessation, on a web site hosted by the remote server. There is no direct connection between the smartphone and the vaping device and the Wi-Fi dock. Wi-Fi connectivity can be implemented not just in a separate dock, but also directly into the case and also the vaping device itself. Direct connectivity between the dock or vaping device, typically over BT (Bluetooth) is also possible. Then, it is the smartphone that sends data (over wireless or Wi-Fi) to the remote server.

Returning to FIG. 26, the case includes an electric pump and pump controller, rechargeable battery and related electronics, including a PMIC (power management IC), a micro-controller, and 1-wire protocol interfaces to the PV and also the liquid refill bottle or capsule. A USB-C charge and data port is included. Data (e.g. usage data and device performance data) is stored on memory (4 Mbit serial flash) in the case; when the case docks with the Wi-Fi dock, then that data is sent over the 1-wire interface to the dock, which then sends it over a local Wi-Fi connection to a remote web-based server.

Figure 27:
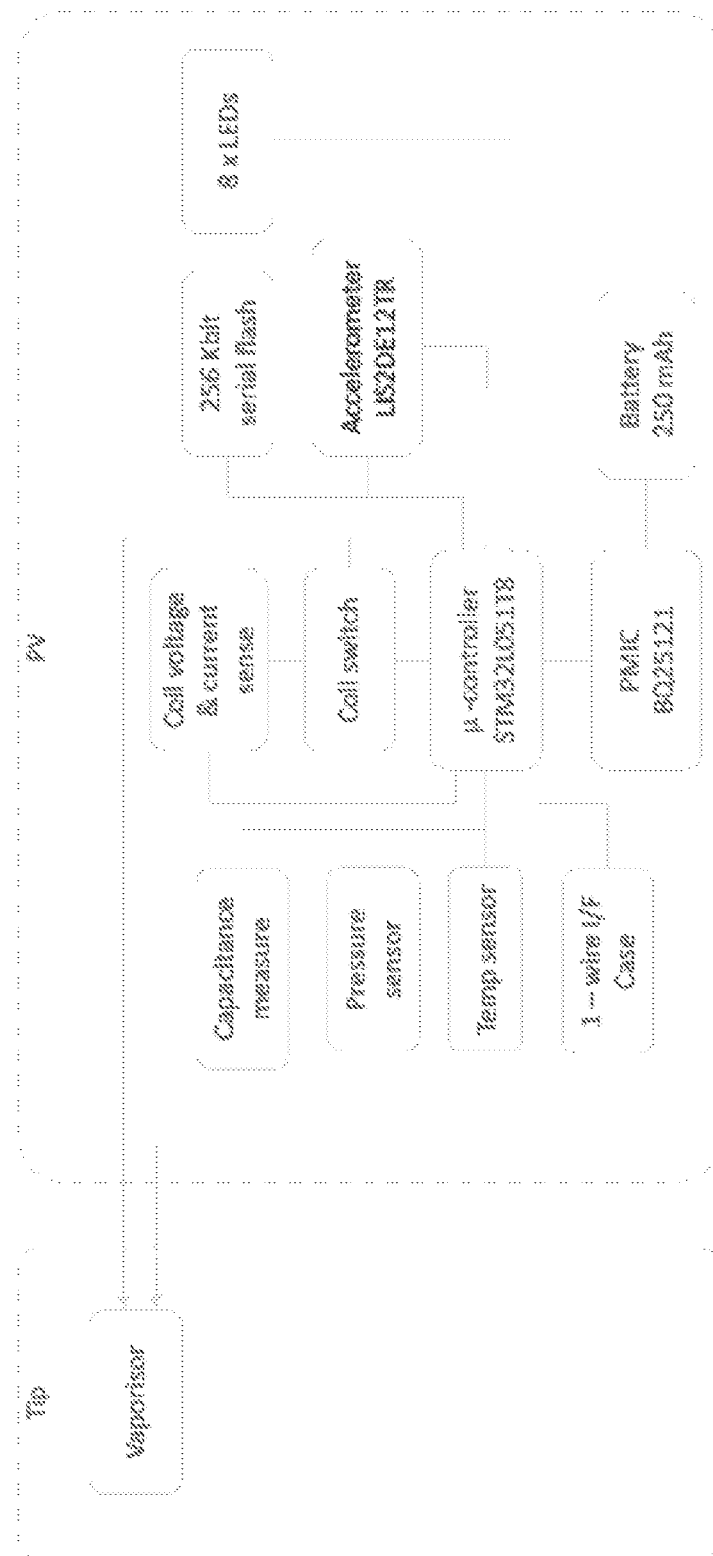
FIG. 27 is a schematic of the electrical and electronic components in the vaping device body (PV) and the tip or pod.

FIG. 27 is a schematic block diagram of the key electronic components in the vaping device body and the refillable tip. The vaping device body (labelled 'PV') includes a capacitive measurement chip or circuit which will be described in more detail in a later section. It also includes an accelerometer (i.e. any form of orientation sensor) that is used to determine when the vaporiser is substantially upright or vertical; the device is configured to be re-fillable only when the personal vaporiser is substantially upright or vertical, as determined by the accelerometer. Enabling liquid re-filling only when the device is substantially vertical or upright greatly simplifies measuring the liquid level in the reservoir in the vaporising device and ensuring that it is not over-filled or under-filled.

Figure 28:
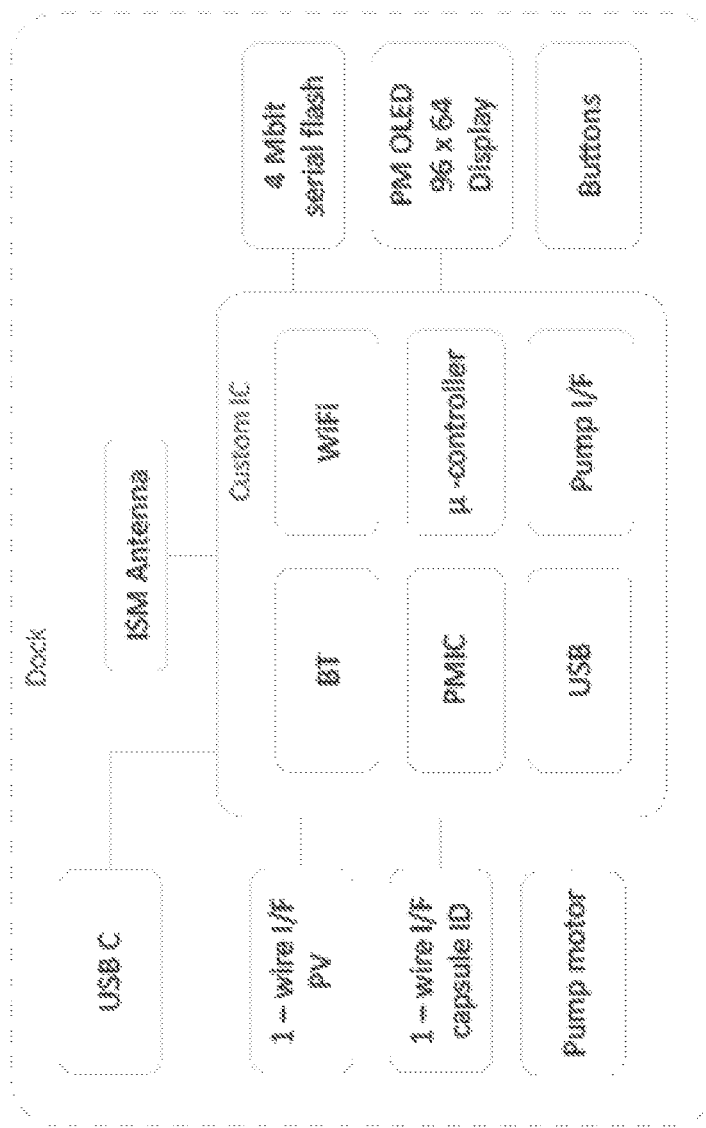
FIG. 28 is a schematic of the electrical and electronic components in a Wi-Fi dock with an integral pump and a custom ASIC.
Figure 29:
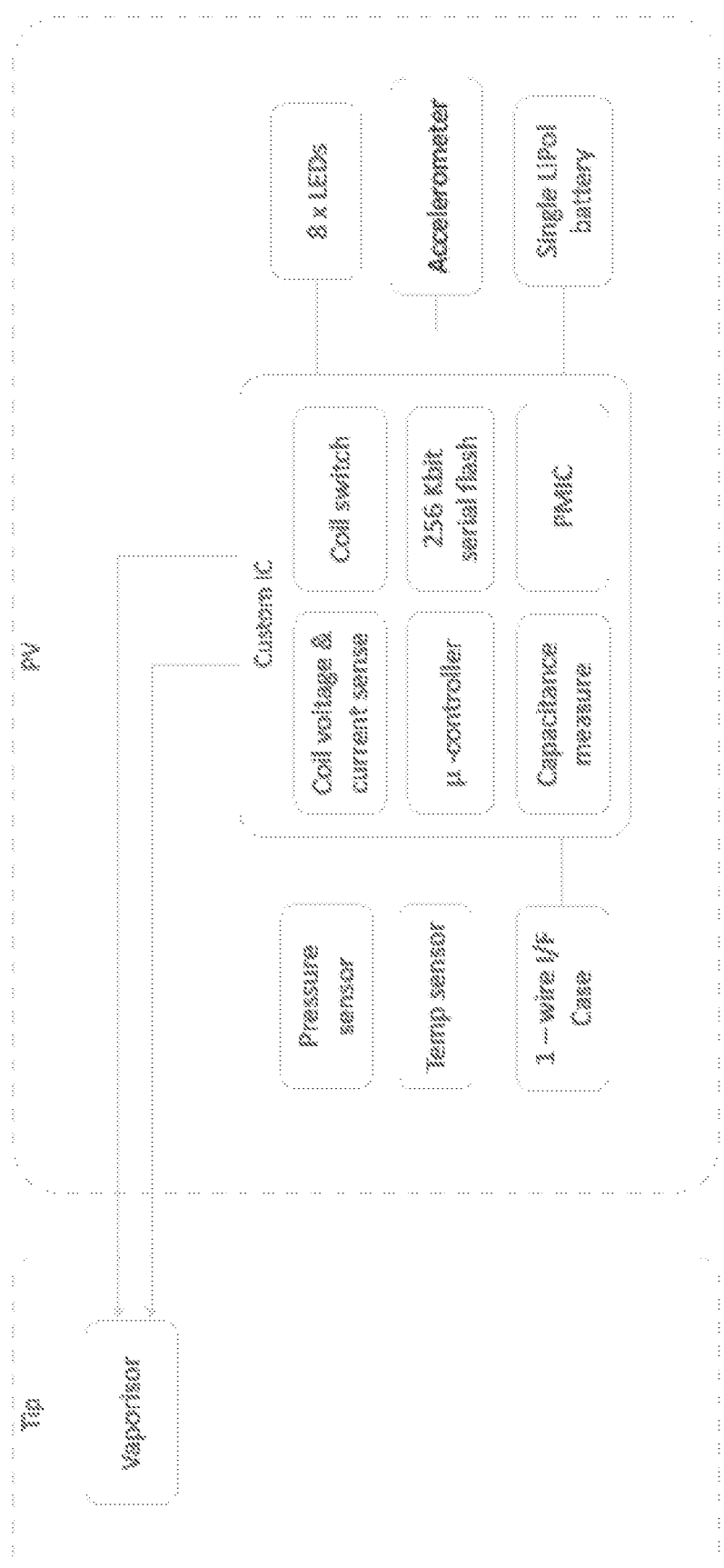
FIG. 29 is a schematic of the electrical and electronic components in a vaping device body (PV) and tip that re-fills and re-charges using the dock shown in FIG. 28, also including an ASIC.

Because of the number of discrete electronic components, there is considerable scope for consolidating many of these into a custom ASIC; this leads to faster manufacture, greater reliability and lower cost. FIG. 28 shows how a custom ASIC can be used in a Wi-Fi dock that also re-fills and re-charges the vaping device (i.e. the AYRBase implementation): the ASIC would typically include not only Wi-Fi, but also Bluetooth capability, a PMIC (power management IC), a micro-controller, USB handling and the pump interface. FIG. 29 shows how a custom ASIC can be used in the vaping device as well: the ASIC could include the coil voltage and current sensing circuit used for temperature regulation of the heating element, a micro-controller, the capacitance measuring circuit, the coil on/off switch, serial flash memory and a PMIC. The custom ASICs could also include UWB functionality.

We can summarise and generalise the key features as follows:

Age Verified, Counterfeit-Protected Vaping

A major issue in the vaping industry is the prevalence of both counterfeit pods, the ease with which authorised pods can be refilled by users with illicit liquids or liquids that contain contaminants. Another major issue is the easy availability and attractiveness of these devices to young people, despite responsible manufacturers specifically targeting these devices to adult smokers. These two issues are inter-linked because counterfeit pods or contaminated liquids are especially dangerous to under-age users (who are intrinsically more vulnerable to contamination) and yet under-age users are more likely to purchase counterfeits or contaminated liquids because they are typically cheaper and available through non-regulated channels that otherwise sell only to adults.

One feature of AYR is that it provides a unified solution to these related issues. In the AYR system, the re-fill bottle includes an authentication chip. But the pod is itself also counterfeit protected (e.g. it includes a secure authentication chip that includes a unique ID available only to authorised pods) and the vaporising device can verify that a satisfactory ID is present on any pod that is attached to the vaporising device. The device includes connectivity (typically via a connected smartphone) to a remote server that enables the device to tell the server the unique ID of the pod and get permission back to use that pod; the server can hence prevent use of any duplicate pods with duplicate IDs.

The connectivity is also used to enable the user, again typically using a connected smartphone, to interact with a web server based age verification system: For example, when a new vaporising device is first used by a specific user, then that user has to pair that device with their smartphone and start the web server based age verification system; this can use a variety of age verification approaches to ensure that the user is an adult (e.g. checking against electoral roles, or credit card availability, or passport or driving licence records etc); only once that user has been verified as an adult is the paired vaping device unlocked. This overall approach minimises the risks associated with under-age use and also use of counterfeit pods or pods that have been re-filled with contaminated liquids.

We can generalise as follows:

A vaping system including an atomiser pod pre-filled with an atomisable liquid, and a vaping device main body, in which the pod includes an authentication chip or memory and the vaping device body includes a pod authentication sub-system that enables a pod to be used with that body only if certain pod criteria are met;

and the vaping device body further includes a wireless connectivity sub-system that (i) exchanges data with an application or browser running on a user's smartphone, the application or browser connecting to a web server based age verification and pod usage system and (ii) is configured to unlock the body to enable normal vaping use only if that user passes the age requirements of the age verification system and the pod is authorised for use.

Some optional features:

The authentication chip or memory is a memory, secure chip or a crypto-chip storing an identifier that enables the source of the pod and/or the liquid in it to be authenticated, verified or determined.

the pod authentication sub-system (a) determines locally or using a remote server if values held on the authentication chip or memory meet the pod criteria and (b) permits use of that pod only if those pod criteria and the age requirements are met.

a counter on the authentication chip or memory decrements each time the pod is used, such as each time an inhalation is taken, and is initially set at a number corresponding to the expected total number of inhalations from a single pre-filled pod, and the pod authentication sub-system is configured to prevent further use of a specific pod once the counter falls below a set figure.

memory uses an EEPROM emulation mode that irreversibly decrements a counter.

the pod authentication sub-system sends a signal to the authentication chip or memory on the pod each time an inhalation occurs.

the pod authentication sub-system causes the counter on the authentication chip or memory on the pod on the pod to decrement each time an inhalation occurs.

the pod authentication sub-system reads from the authentication chip or memory on the pod an identifier that enables the source of the pod to be verified or determined and the wireless connectivity sub-system is configured to (i) send that identifier to a remote server for processing that identifier and (ii) receive a permission or denial signal from the remote server.

A browser autoruns or executes a URL for the web server-based age verification system and the wireless connectivity sub-system connects over Wi-Fi to the web server.

The browser is opened or initiated to run the URL when the user touches an icon designed to appear to be an application icon on their smartphone device.

The vaping device main body includes a Wi-Fi connectivity module or is configured to dock with a docking station or case that includes a Wi-Fi connectivity module.

The vaping device body includes a location module, such as a GPS or UWB module, and the module sends location data to a geo-fencing system that determines if the vaping device body is in an area where vaping is either permitted or not-permitted, and sends a signal to the vaping device body locking it from use if it is in an area where vaping is not permitted.

The vaping device body includes a receiver that listens for location specific signals, such as signals from a UWB beacon, and the vaping device body locks from use if it picks up such a signal.

The web server based age verification system verifies a user's age using one or more of the following: age self-verification by the user; age verification using a linked credit card or other age-verified payment card or system for the user; age verification using information from the user's passport; age verification using information from the user's social security or national insurance or similar records; age verification using information from the user's driving licence; age verification using information from one or more of the user's social media accounts; age verification using information derived from behavioural analytics systems.

Bottle that Cannot be User Re-Filled

With conventional pods or tips, a determined user can buy a legitimate pod, use it, and then re-fill it with new liquid, which may include illicit ingredients or contaminants, which may lead to injury or illness. The pod can then be placed back onto a vaping device. To prevent this sort of user re-filling with liquid, the AYR re-fill bottle includes a secure memory chip with a counter that is set to some suitable number, such as 256. Each time liquid is automatically withdrawn from the re-fill bottle by the fluid transfer system, the system checks the number on the counter and decreases the counter by 1. Once the counter reaches zero, the fluid transfer system will no longer withdraw liquid from that bottle; it is in effect locked from further use, even if a user were to re-fill it with liquid. The same system can be used in a pre-filled pod.

We can generalise as follows:

A vaping system including a liquid re-fill bottle or container and a liquid transfer system configured to automatically transfer liquid from the bottle or container to a liquid reservoir in a vaping device; in which the bottle or container includes a counter in a memory chip that is configured to change its value when a defined type of event affects the bottle or container, so that when the counter reaches a limit (e.g. zero) or other value, the bottle or container is locked from further use.

A liquid re-fill container storing liquid for a vaping device, in which the capsule includes a counter in a memory chip that is configured to change its value when a defined type of event affects the capsule, so that when the counter reaches a limit (e.g. zero) or other value, the container is locked from further use.

As noted above, the approach of using a secure counter applies not just to re-fill bottles, but also to pre-filled cartomiser pods.

We can generalise as follows:

A vaping system including a pre-filled liquid pod configured for a vaping device, the pod including a counter in a memory chip that is configured to change its value when a defined type of event affects the pod, so that when the counter reaches a limit (e.g. zero) or other value, the pod is locked from further use.

A pre-filled liquid pod configured for a vaping device, the pod including a counter in a memory chip that is configured to change its value when a defined type of event affects the pod, so that when the counter reaches a limit (e.g. zero) or other value, the pod is locked from further use.

Some optional features:
The defined type of event is use of the pod, such as withdrawal of liquid from the pod.
The pod includes a memory chip with an EEPROM emulation mode that enables writing to the counter in the chip every time the defined type of event affects the capsule.
The counter starts at a set number, such as 256, and is decremented by 1 whenever the defined type of event affects the capsule.
Controller has to read a value in excess of 1 from the counter in order to permit liquid to be withdrawn from that container.
The pod is configured to slid into or otherwise engage with a vaping device body.

PIN Lock

Another feature in AYR devices is that they can be locked and unlocked by the user; the case includes a locking system into which a user has to enter a correct sequence of numbers or other identifier in order to activate or unlock the system. A simple and low-cost system combines a screen, such as a low cost OLED matrix display (e.g. 96×64) with a simple mechanical scrolling actuator that enables a user to input forward, back and select controls. This enables the user to rapidly enter for example a 4 digit security PIN to lock and unlock the device. The system can be adapted to enable the user to scroll through different numbers or other identifiers and select an appropriate number or other identifier. It can be implemented on a re-filling case or docking station for a vaping device or directly on the personal vaping device itself.

Constant Temperature Driver

The AYR system is able to regulate the temperature of the heating element to within 20 degrees or better. Accurate temperature regulation is very important since it means that the vapour constituents can be understood and tested for safety; most atomiser heating systems lack effective temperature regulation and hence there can be spikes in the coil temperature, which can lead to the production of undesirable chemicals in the inhaled vapour. Accurate temperature regulation is also important since it greatly increases the longevity of the atomising unit. The AYR system operates by measuring the current passing through the heating element for a known voltage; it calculates the resistance from this data and then looks up, from stored data for the temperature coefficient of resistance of the heating element, what the temperature is. This feeds into a closed loop temperature regulation system; the power duty ratio from a PWM current source that provides the current to the heating element is adjusted to ensure the temperature is at a required level or range. The closed loop is damped by the liquid that feeds the atomising system.

We can generalise as follows:

A liquid atomising system with a heating element configured to heat an atomisable liquid and to produce a vapour, atomisation or mist, and that is controlled with a constant temperature driver, the driver directly or indirectly measuring the current through a heating element using a power source with a known voltage and enabling a microcontroller or processor to (a) calculate or determine the resistance of the heating element and to (b) calculate, from stored data for the temperature coefficient of resistance of the material the heating element is made from, or (c) look up, the temperature of the heating element;

and in which the driver is configured to use a closed loop temperature control algorithm to regulate the power, current or voltage to stabilize the temperature of the heating element at a preset level or range by adjusting the power duty ratio.

Some optional features:
The driver operates a closed loop temperature control algorithm and regularly adjusts the power duty ratio after each instance of the current being measured.
The current is measured approximately 30 times a second.
Preset level is approximately 280 degrees centigrade when the liquid is a PV/VG e-liquid.
Preset level is varied depending on the type or chemical composition of the liquid.
a heating element made of a material with a temp coefficient of resistance that is substantially linear, such as stainless steel 316L.
the control loop is configured to be damped by the thermal mass of the atomisable liquid.

Graceful Data Termination

Because the vaping device sends data to a host (e.g. a docking station or case), it is important that the data is not corrupted. But the vaping device can be withdrawn rapidly from the dock and the case and doing so whilst data is being sent or received can lead to corruption. We solve this problem by providing a small switch (in the device, or case or dock) that is triggered as soon as the vaping device moves out of position, but before data contact is lost (data contact is provided via sprung mounted pogo pins, so these pins maintain contact momentarily as the vaping device is moved up and out of the dock or case). When the switch activates, a control routine over-rides the data transfer and brings it to a rapid but controlled termination.

We can generalise as follows:

A liquid re-filling device that stores a vaping device and enables the vaping device to be ejected or withdrawn, and the re-filling device and/or vaping device includes a switch that is (a) activated as the vaping device starts to be ejected or withdrawn from the re-filling device and that (b) sends a signal to ensure that any data communications between the vaping device and the re-filling device are terminated in a controlled manner before a data connection is lost.

Upright Re-Filling

Measuring the amount of liquid in a very small reservoir (capacity is approximately 2 mL) is challenging. The AYR system needs to do this cheaply and reliably in mass produced products. AYR uses a sophisticated liquid level sending system that determines whether the level of liquid in the re-fillable pod is below a threshold and hence requires re-filling. Whilst it would be possible to compensate for the tilt of a device using the in-built accelerometer, that is not wholly reliable. Instead, AYR measures the level of liquid in the re-fillable liquid reservoir specifically when the vaping device which the pod is attached to, is substantially upright or vertical. This is achieved using the accelerometer, which can be in the vaping device, or the dock, or both. Only when the device is substantially upright or vertical, and a liquid level measurement is completed which indicates that the level of liquid in the pod reservoir is below a threshold, is the fluid transfer system activated and liquid pumped into the liquid reservoir from the refill bottle.

We can generalise as follows:

A vaping system that is configured to automatically re-fill a vaping device only when the vaping device, or a liquid reservoir in the device, is substantially upright or vertical.

Some optional features:
The system includes an accelerometer that sends a signal when it is substantially upright or vertical.
Only when the device is substantially upright or vertical, and a liquid level measurement is completed which indicates that the level of liquid in the pod reservoir is below a threshold, is a fluid transfer system activated and liquid pumped into the liquid reservoir from the refill bottle.

Light Patterns

The AYR vaping device includes a series of lights on the vaping device; these progressively extinguish as the user vapes and all are fully extinguished after the user has vaped equivalent nicotine or for an equivalent time to smoking a single cigarette. These lights can be re-purposed for other effects, for example with light patterns made by the series of lights that are controlled by the accelerometer in the vaping device.

We can generalise as follows:

A vaping device that includes a series of lights that progressively extinguish as the user vapes, but can also be controlled to illuminate together or in a sequential sequence or otherwise to form a light pattern.

Some optional features:
There are a line of 5 or more lights on one face of the vaping device.
There are one or more circular light rings around the vaping device.
An accelerometer provides an input to a microcontroller which in turn controls the series of lights.
The light pattern is simultaneous pulsing of all lights.
The light pattern is sequential lighting of the lights to form a pattern that moves down, up or down and up the vaping device.
A specific light pattern indicates that the tip needs changing.
A specific light pattern indicates that the device needs re-filling with liquid.
A specific light pattern indicates that the device is locked from use.

C. Data and Connectivity

AYR Sessions

A significant challenge for smokers looking to quit smoking by transitioning to vaping is that most vaping devices make it difficult to establish some sort of relationship between the amount of nicotine they are inhaling whilst vaping and what they would otherwise be inhaling from cigarettes. Some conventional e-liquid pods contain the same amount of nicotine as 20 cigarettes, but there is no accurate way of knowing when you consume or vape nicotine equivalent to just one of your normal cigarettes.

AYR addresses this by enabling a user, when configuring their AYR device, to set it up so that it works for parameters, such as a time and/or number of inhalations, that will deliver approximately the same amount of nicotine, for a normal or average inhalation, as a single cigarette of the brand they actually smoke. As noted earlier, the AYR vaping device has a series of lights running along one face of the vaping device (typically 8) which progressively extinguish as a session continues; when all lights have gone out, the session is over. Once the sessions expires, the user will either have to wait a preset time, or return the device to its case (if it has one), or some other action or step that enables them to more readily interrupt and hence control the amount of vaping they are undertaking, all in a way that they can relate to their smoking habits.

By mimicking smoking habits in this way, and giving clear visual, audio and/or haptic feedback of the progress of a session, including its start and ending, the danger of a user increasing their nicotine consumption when moving from cigarettes to vaping is minimised. The user can set nicotine consumption reduction or cessation goals via an app, and these goals can be used to alter the parameters for successive sessions, or a program of sessions, so that these goals can be met.

We can generalise as follows:

A vaping system configured to enable a vaping device to be used for a single session, a session being a limited time or limited extent of vaping during which the vaping device is operable and for which the vaping device provides a start and end visual, haptic and/or sonic marker;
and in which the system is configured to receive from a user a selection or indication of the type or brand of cigarette they currently smoke, and the system then automatically adjusts the time or other parameters of the single session so that the amount of nicotine generated by the vaping device, or inhaled by a user, during that session is approximately equivalent to the amount of nicotine associated with smoking a single cigarette of that specific type or brand of cigarette.

Some optional features:
A session is a pre-set time during which the vaping device is operable before automatically and temporarily ceasing to operate.
A session is a pre-set extent of vaping, such as number of inhalations, or quantity of liquid atomized, during which the vaping device is operable before automatically and temporarily ceasing to operate.
The vaping device is programmed so that it automatically ceases to operate for a user defined pre-set time after a session expires.
The vaping device is programmed so that it automatically resumes normal operation if returned to its dock or case and is then withdrawn from that dock or case.
The system includes a smartphone or tablet app which is configured to enable the user to enter a specific type or brand of cigarette.
the system is configured to receive from a user a selection or indication of the nicotine consumption reduction or cessation goals they are planning to achieve, and the system then automatically adjusts the time or other parameters of a program of single sessions so that the amount of nicotine generated by the vaping device during that program of sessions meets the user's nicotine consumption reduction goals.

Wi-Fi Connected Vaping Device

AYR is a 'connected' vaping device; by 'connected', we mean that the device has some form of data connectivity or the ability to send data, or receive data, or send and receive data—e.g. to or a user's smartphone or smartwatch etc and/or to a remote server, either directly or indirectly. Connectivity also enables the user to control the vaping device from their smartphone etc, and for the vaping device to send useful data, such as consumption or usage data, or battery level data, or liquid level data etc to the remote server. It also enables the consumer to order consumables (e.g. new prefilled pods or heat sticks etc). Connectivity also enables rich behavioural insights to be harvested from the data.

Connected vaping devices have been discussed for many years; connectivity is enabled by including within the device itself some data connectivity system—e.g. a Bluetooth modem, together with a mobile app for the user's smartphone.

The approach of Bluetooth connectivity linking the vaping device to a user's smartphone, running a mobile app, is the overwhelmingly standard way of implementing connectivity: it represents a very strong technical bias that colours the thinking of the typical engineer. Faced with the challenge of making a non-connected vaping device into a connected vaping device that can be accessed from the user's smartphone, the inevitable response from the typical engineer is therefore to include Bluetooth connectivity directly into the vaping device and build a companion mobile app, which is then made available from the smartphone vendor's app store.

But including a Bluetooth modem within a portable vaping device is problematic because it adds significantly to the complexity of the device and adds new failure modes to the device—although it may appear relatively simple, it can be challenging to ensure that Bluetooth works reliably across the full range of possible smartphones and other devices.

Further, not all users will want or use connectivity. And a significant number of potential users will be alarmed that the device is connected, for personal privacy reasons; merely not activating connectivity is rarely enough for such potential users, because they fear that covert monitoring may nevertheless be taking place.

And a further layer of complexity arises because it requires a mobile app to be available for the user's smartphone operating system (e.g. from the Apple App Store, or Google Play Store). But that OS vendor may impose different rules on what apps are or are not available on its store. For example, Google Play Store is currently very permissive. But the Apple App Store does not permit companion apps for nicotine vaping devices.

But they do permit companion apps for devices that enable CBD or THC to be inhaled. And these rules may change at short notice; for example, the Google Play Store could choose to also ban apps relating to nicotine vaping devices.

This is a surprisingly complex set of technical challenges—namely to design a portable vaping device system that:
- is potentially connectable, yet has the lowest cost and complexity.
- is potentially connectable, yet cannot compromise personal privacy for those users who are sensitive to that issue.
- is potentially connectable, but is not affected by the inconsistent rules imposed by device vendors for companion apps available from their online app stores.

Whilst it would be possible to integrate full 3G or 4G wireless connectivity into a vaping device, that would significantly increase the price; instead, it is preferable to take advantage of existing connectivity infrastructure. The route we have chosen with the AYR Case is for the vaping device to collect data and for the case also to collect data; when the vaping device is inserted into the case, then the case collects the data from the PV. The case itself does not include a Wi-Fi module, although that is one possible variant.

In the current variant, the case is slotted into a slim dock (see FIG. 30) that does include a Wi-Fi module and Wi-Fi antenna. The dock also serves to provide power to the case over a USB-C port to charge the internal rechargeable battery in the case. The case transfers data to the Wi-Fi dock over USB-C, and that data is then sent over a local Wi-Fi network that the dock has been attached to in the normal manner by the user. Data is sent to a remote server for processing; related data is provided to the user when that user opens a web browser at a specific URL.

BLE is used as a transport protocol running over Wi-Fi so that the vaping device appears as an IoT endpoint and no smartphone app from an app store is needed. Instead, only a web browser is needed. A single connectivity API, namely the BLE API, is used; the case treats the wi-fi and charging dock as an additional BLE module with the same interaction protocol and communicates with it in terms of BLE characteristics (e.g. notify on Characteristic with given UUID has changed). An AYR specific protocol on top of BLE is implemented only once and used for both communicating with a connected smartphone and with a web-based user application; the web-based user application presents itself on the user's smartphone screen as an icon just like a conventional app icon from the App Store or Play Store, although it is in fact no such thing. The dock for the AYRCase is hence essentially a charging platform with a built-in Wi-Fi module.

A Wi-Fi module could also be included in a dock sized to receive just the vaping device on its own. The dock in the AYRDock variant, which both re-charges and also re-fills the vaping device with liquid, can also itself include the Wi-Fi module.

We can summarise and generalise as follows:

A vaping system comprising:
(i) a vaping device including a rechargeable battery and a data port; and
(ii) a first charging system for that vaping device and that is configured to provide power to the rechargeable battery; and
(iii) a separate, second charging system that is configured to receive the vaping device and to provide power to the rechargeable battery and to receive data from the vaping device via the data port; and
(iv) a mobile website configured to be hosted on a remote server and to be accessible from an end-user's smartphone, smartwatch or other personal device;
and in which the second charging system includes a Wi-Fi module, chip or unit configured to send the data received from the vaping device, to the mobile website hosted on the remote server over the internet.

The first charging system is typically just a conventional USB charging cable that plugs directly into the vaping device. The second charging system is typically one of the following:
(a) a charging dock that a vaping device directly docks into and that has in-built Wi-Fi based data connectivity;
(b) a re-fill and re-charge case that a vaping device slots into, plus a dock for that case with in-built Wi-Fi based data connectivity, as shown in FIG. 30;
(c) a re-fill and re-charge case that a vaping device slots into for storage, where the case itself has in-built Wi-Fi based data connectivity (d) a USB charging cable that includes a Wi-Fi module, the charging cable plugging directly into the vaping device;

(e) a USB charging cable terminating in a platform with a USB connector, where the platform includes a Wi-Fi module and the vaping device docks with the platform.

This architecture resolves the complex set of technical challenges outlined above. Data is, as noted above, sent to the remote server for processing and possible display by the mobile website. Because a mobile website is used, and there is no need for an app that must be downloaded from a device manufacturer's app store (e.g. Apple App Store or Google Play Store), the mobile website can provide full and consistent functionality across all devices, whether Apple iOS or Android, and irrespective of whether the inhaled substance is nicotine, or CBD or THC or indeed anything else. Full functionality, such as ordering fresh pre-filled capsules or other consumables is possible. Further, users who do not want any form of connectivity can merely use the first charging system that has no data connectivity (this could be as simple as a USB power cable). They will be fully confident that there is no possibility of compromising data privacy as they can simply choose not to use the second charging system, which would other provide connectivity. Other users who do want data connectivity and a fully functioning connected experience using their smartphone or other smart device have only to use the second charging system, e.g. charging dock that a vaping device docks into and that has in-built Wi-Fi based data connectivity; or a re-fill and re-charge case that a vaping device slots into, where the case itself is then placed into a dock with in-built Wi-Fi based data connectivity; or a re-fill and re-charge case that a vaping device slots into, where the case itself has in-built Wi-Fi-based data connectivity; or a USB charging cable that includes a Wi-Fi module.

Some optional features:
- The first charging system is a charging cable that plugs directly into the vaping device.
- The first charging system is a desktop docking station, but without any Wi-Fi module, chip or unit.
- The first charging system is a dock that connects to a USB or other port in a computer or other device to receive power from the computer or other device.
- The second charging system is a charging dock that the vaping device directly docks into and that has in-built Wi-Fi based data connectivity.
- The second charging system is a re-fill and re-charge case that a vaping device slots into, plus a dock for that case with in-built Wi-Fi based data connectivity.
- The second charging system is a re-fill and re-charge case that a vaping device slots into for storage, where the case itself has in-built Wi-Fi based data connectivity.
- The second charging system is a USB charging cable that includes a Wi-Fi module.
- The second charging system is a USB charging cable terminating in a platform with a USB connector, where the platform includes a Wi-Fi module.
- BLE is used as a transport protocol running over Wi-Fi so that the vaping device appears as an IoT endpoint.
- BLE is used as a transport protocol running over Wi-Fi so that the vaping device appears as an IoT endpoint so that no smartphone app from an app store is needed, but instead just a web browser.
- The system uses a single connectivity API, namely the BLE API.

Another approach is to integrate the Wi-Fi module directly into the vaping device itself and not have a separate dock; we can generalise as follows:

A portable vaping device system comprising:
(i) a portable vaping device including a rechargeable battery and a data port; and
(i1) a mobile website configured to be hosted on a remote server and to be accessible from an end-user's smartphone, smartwatch or other personal device; and in which the vaping device includes a Wi-Fi module, chip or unit configured to send data to the mobile website hosted on the remote server over the internet.

Server Analytics

As noted above, AYR is a Wi-Fi connected device, providing data (with user consent) to a server that analyses the data and generates consumer or behavioural data insights based on the usage data. This stands in contrast to the standard approach, which requires a Bluetooth connectivity module, and a smartphone app, which may itself not be available for significant operating systems, such as Apple iOS. Providing a Wi-Fi connected device is key to achieving representative, high quality data to be mined for consumer or behavioural insights; vaping systems that use only Bluetooth connectivity may be skewed to cover only users that can pair their vaping systems to Android smartphones, compromising the quality of the resulting data and hence the insights.

We can generalise as follows:

A vaping data analysis system including a vaping system and a remote server, in which the vaping system collects usage data relating to how the device is being used by a consumer and sends that usage data directly or indirectly to a remote server using Wi-Fi connectivity to the internet, the Wi-Fi connectivity being established by the vaping device; and the server analyses the data and generates consumer or behavioural data insights based on the usage data.

Some optional features:
- Wi-Fi connectivity is provided by a charging dock that a vaping device directly docks into and that has in-built Wi-Fi based data connectivity.
- Wi-Fi connectivity is provided by a re-fill and re-charge case that a vaping device slots into, plus a dock for that case with in-built Wi-Fi based data connectivity.
- Wi-Fi connectivity is provided by a re-fill and re-charge case that a vaping device slots into for storage, where the case itself has in-built Wi-Fi based data connectivity.
- Wi-Fi connectivity is provided by a USB charging cable that includes a Wi-Fi module, the charging cable plugging directly into the vaping device.
- Wi-Fi connectivity is provided by a USB charging cable terminating in a platform with a USB connector, where the platform includes a Wi-Fi module and the vaping device docks with the platform.
- The usage data relates to the flavour and strength of liquid being atomized; and the remote server generates data comprising feedback, such as real-time feedback, to liquid filling and logistics systems to ensure that the most popular flavours are in store and on-line when needed.
- The usage data relates to the flavour and strength of newly launched liquids being atomized; and the remote server generates data comprising feedback, such as real-time feedback, to liquid and flavour houses to ensures fast, evidence-based creation and roll out of new flavours, including flavours that appeal to smokers and not to under-age users.
- The usage data relates to the geolocation of flavours and strengths of liquid being atomised; and the remote server generates data comprising feedback, such as real-time feedback, to capsule filling and logistics systems to ensure that the most popular flavours are in-store or on-line in the cities or regions where they are most needed.

The usage data relates to the characteristics associated with under-age consumers of liquid and the remote server generates data comprising warning messages to those consumers or other persons.

The usage data relates to the characteristics associated with under-age consumers of liquid and the remote server generates data comprising an alert signal to an adult or an organization, such as a school or college.

The usage data relates to the characteristics associated with under-age consumers of liquid and a geolocation of the atomizing device and the remote server generates data comprising an alert signal to an adult or an organization, such as a school or college.

The usage data relates to the characteristics associated with under-age consumers of liquid and the remote server generates data comprising a signal that stops or locks the atomizing device.

The usage data relates to liquid level in the device and any associated capsules; and the remote server generates data including messages that prompt the user to buy more capsules or liquid—e.g. through e-fulfillment, and to provide special offers/coupons for use in stores or online.

The usage data relates to the flavour and/or strength of liquid being atomised; and the remote server generates real-time feedback to consumers suggesting other flavours they might like.

The usage data relates to the self-reporting on continuing cigarette smoking; and the remote server generates real-time feedback on the positive health impact of reduced cigarette consumption.

The usage data relates to patterns or usage over time; and the remote server generates data that relates to any correlation with advertising or marketing to determine the effectiveness of that advertising or marketing.

The usage data relates to patterns or usage over time; and the remote server generates data that provides insight into product usage for regulators or health service providers.

The usage data relates to times of usage, or duration of each session, or quantity of liquid consumed; and the remote server generates data that provides real time insight into usage.

The usage data relates to the age, sex and other demographic data of users; and the remote server generates real-time demographic insight into who is using the device.

UWB Connected Vaping Device

The UWB (Ultra Wideband) standard enables very low cost and low power consumption chips to be added to electronic devices and to make those devices location aware to an accuracy of a few cm and be capable of exchanging data (such as location data) with other devices (including UWB equipped smartphones, such as the Apple iPhone 11). A vaping device equipped with a UWB capability could hence establish its location with great accuracy and share that location with other devices; this would enable vaping devices to be automatically disabled in areas where vaping was not permitted (such as aircraft, or within school buildings or wider school premises); for example, a UWB beacon (fixed or mobile) in a vaping restricted area could be continuously broadcasting a message or flag that any UWB-equipped vaping device would pick up when sufficiently close or within a defined no-vaping area; receipt of that message or flag would automatically be processed by the vaping device and lead to it disabling itself; it would display a warning light or message that would alert the user to this cause of disablement. The UWB beacon could be an authorised user's smartphone or tablet: a school teacher could hence activate the flag or message at any time or location and hence disable vaping devices that pick up that flag or message.

We can generalise as follows:

A portable vaping device including a UWB chip or ASIC integrating UWB functionality.

Some optional features:

The UWB chip or ASIC integrating UWB functionality provides geo-location and/or geo-fencing capability to prevent the operation of the portable vaping devices in defined areas.

The vaping device listens for a specific message or flag broadcast from a UWB device that causes the device to automatically disable itself The vaping device tracks its location using UWB and establishes if it is at a location where vaping is or is not permitted and, if it is in a location where vaping is not permitted, then it disables itself.

The vaping device tracks its location using UWB and shares that location with another UWB enabled device.

The UWB enabled device that the location data is shared with determines if vaping is permitted in the location of the vaping device and sends a flag or message to that vaping device if vaping is not permitted.

The UWB enabled device that the location data is shared with is a smartphone.

The UWB enabled device that the location data is shared with is a dock that re-fills the vaping device with liquid and re-charges a battery in the vaping device.

The UWB enabled device that the location data is shared with is a portable re-fill and re-charge case that re-fills the vaping device with liquid and re-charges a battery in the vaping device.

D. Liquid Handling and Re-Filling

As described earlier in this document, AYR uses an active fluid management system to automatically re-fill a small liquid reservoir or chamber (typically with between 1 mL-2 mL liquid capacity) in the vaping device to a pre-determined fixed threshold; this small liquid reservoir feeds liquid into the atomising unit which generates an aerosol from that liquid. This active fluid management system is used to automatically and without user initiation re-fill a vaporiser device with liquid from a larger reservoir—typically a user-replaceable but not user-refillable bottle, such as a 10 mL refill bottle. The active fluid management system is very compact and cost effective and relies on measuring the electrical capacitance of the small chamber; this capacitance changes with the volume of liquid in this chamber. Whilst this section will describe the capacitive system in detail, there are other liquid level sensing technologies which the AYR system could use, such as simple optical systems where a beam of light is sent through a transparent walled liquid reservoir at a point half-way up that reservoir; if the beam is interrupted in a way that is characteristic of absorption by the type of liquid in the reservoir, then the system assumes that the reservoir is at least half-full with liquid, and pumping is not activated. But if the beam is not interrupted in that way, the system assumes that the reservoir needs filling, and pumping is activated. The light beam and sensor are positioned in the dock or case. We have found however that the capacitance measuring system is reliable and cost-effective.

Basic Operation

Figure 31:
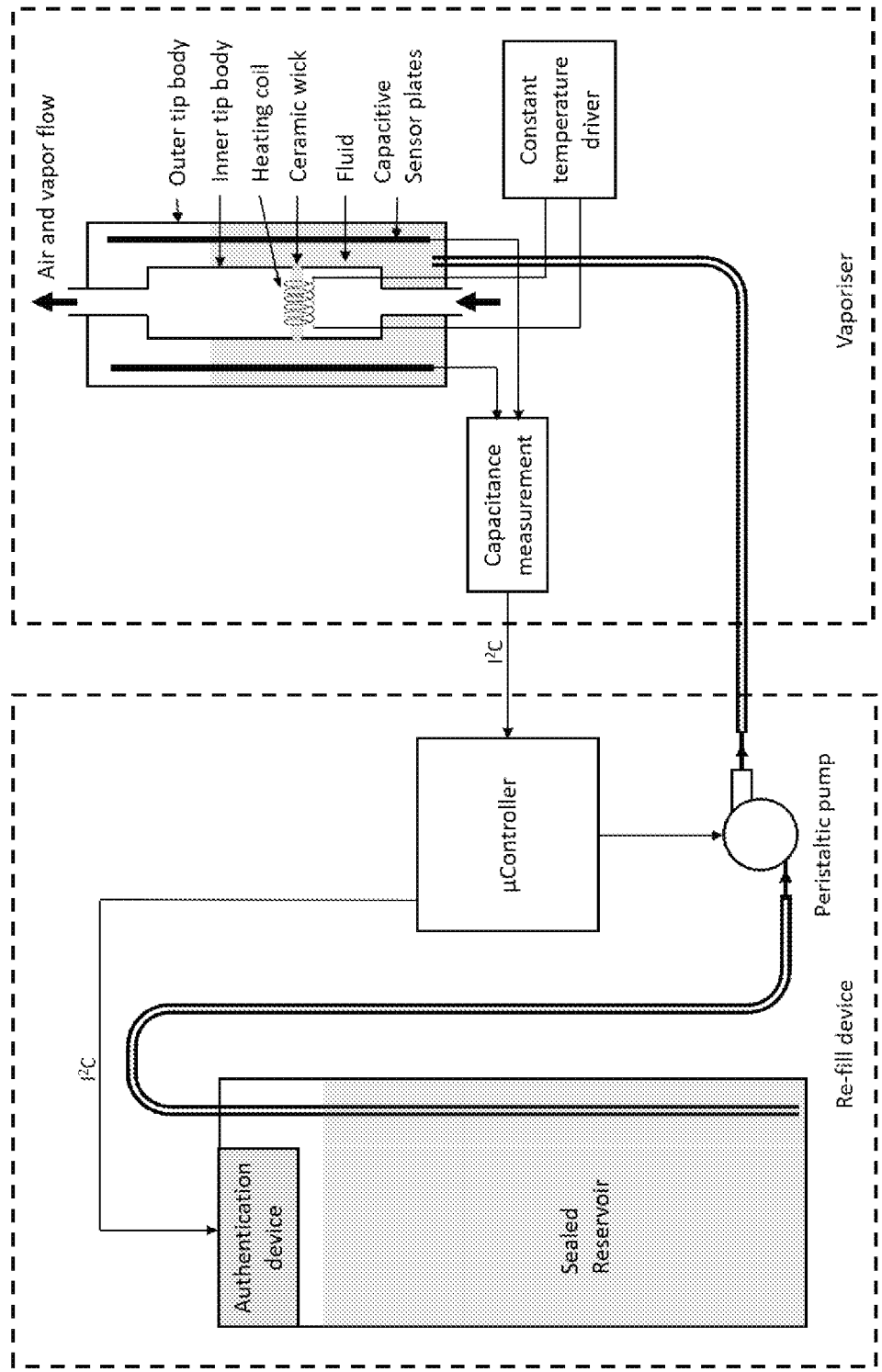
FIG. 31 is a schematic of the liquid level sensing system that measures the liquid level in the tip and control the fluid re-filling pump.

FIG. 31 shows a simplified block diagram of the core elements of the entire vaping system. The fluid reservoir 301 in the vaping device contains a heating coil 302 supported in a silicone jacket. The amount of fluid in the small chamber is sensed by reading the electrical capacitance between the two capacitor sensor plates 303 in the chamber. This capacitance is approximately proportional to the amount of e-liquid in the chamber. The microcontroller 304 in the re-fill device controls the peristaltic pump 305 by comparing the capacitance of the small liquid reservoir in the vaping device to a pre-set threshold. If the capacitance is below this threshold it will activate the pump and withdraw liquid from the sealed reservoir (e.g. 10 mL liquid refill bottle) and pump it into the liquid reservoir 301 until the level reaches this threshold.

Closed Loop Control

The re-fill function is only activated after the vaporiser device has finished a vaping session and the vaping device has been returned to the re-filling device (e.g. the desktop dock for AYRBase, or the re-fill and re-charge case for AYRCase) and the vaping device is positioned vertically. Where the vaping device has an integral, internal liquid pump (AYRMod), then the re-fill function is again activated after the vaporiser device has finished a vaping session and is positioned vertically.

Once activated the microcontroller implements a closed loop control of the pump, pumping liquid until the pre-defined threshold is reached. This maintains the level of liquid in the vaporiser at approximately the same level. In the AYR devices, the level is approximately 50%-60% of the maximum liquid capacity of 2 mL—i.e. approximately 1 mL.

Capacitance Measurement

The capacitance of the sensor in the vaping device is measured using a parallel resonance method. An inductor and capacitor tank oscillator circuit is used; the exact resonance frequency is sensed; the value of the external sense capacitor is calculated from this resonance frequency. To ensure high accuracy and repeatability, each measurement circuit is individually calibrated on the production line to compensate for all the stray capacitances in the circuit board and interconnects between the vaporiser and measurement circuit.

Figure 32:
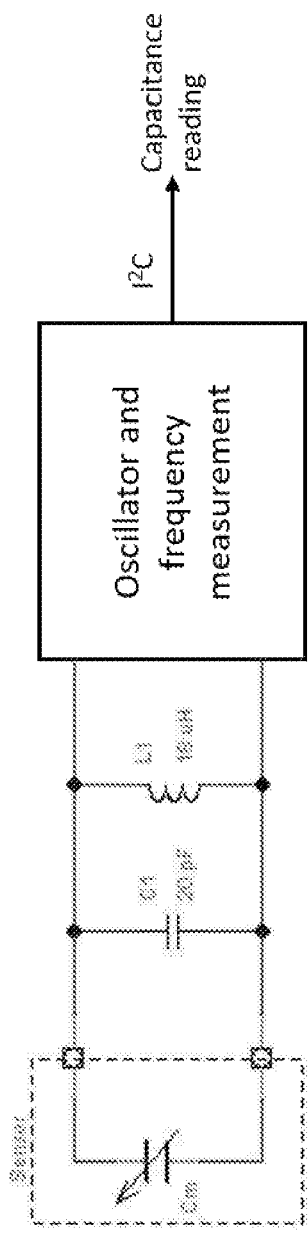
FIG. 32 is a schematic of the capacitance measuring circuit used in the liquid level sensing system.

FIG. 32 shows a simplified schematic. This circuit is designed to measure capacitance in the range of 0-20 pF. The calibration constants obtained from the production line calibration process are stored in non-volatile memory (in the vaping device) and are used by the system software to remove static stray capacitance. The current implementation uses a dedicated integrated circuit to form the oscillator and frequency measurement functions. In time this could be evolved into a discrete, more cost effective design; integrating as many functions into a custom ASIC is a key approach to reducing the cost-of-goods or COGs of the device.

Liquid Characterisation and Authentication

The capacitance change of the sensor is proportional to the amount of liquid in the chamber, but it is also dependent on the chemical makeup of the liquid (e.g. nicotine strength, whether it is a nicotine salt or not, the flavourings used, the amount of water present, the amounts of PV and VG) and the temperature of the liquid. This means that each liquid formulation needs to be characterised in terms of weight of liquid vs capacitance reading and these constants need to be stored with the liquid on the large reservoir, e.g. the 10 mL refill bottle. This data is stored in a small serial ROM chip that is attached to the large reservoir which can then be read by the microcontroller in the vaping device before commencing filling.

In addition, this ROM chip contains (i) an encrypted secret key which is used to authenticate the reservoir (capsule) and (ii) a count-down (only) counter to prevent re-filling of unknown liquids. If authentication and re-fill prevention are not required, the e-liquid characteristics could be stored optically on the capsule to reduce cost, for example as a bar code or other glyph.

Figure 33:
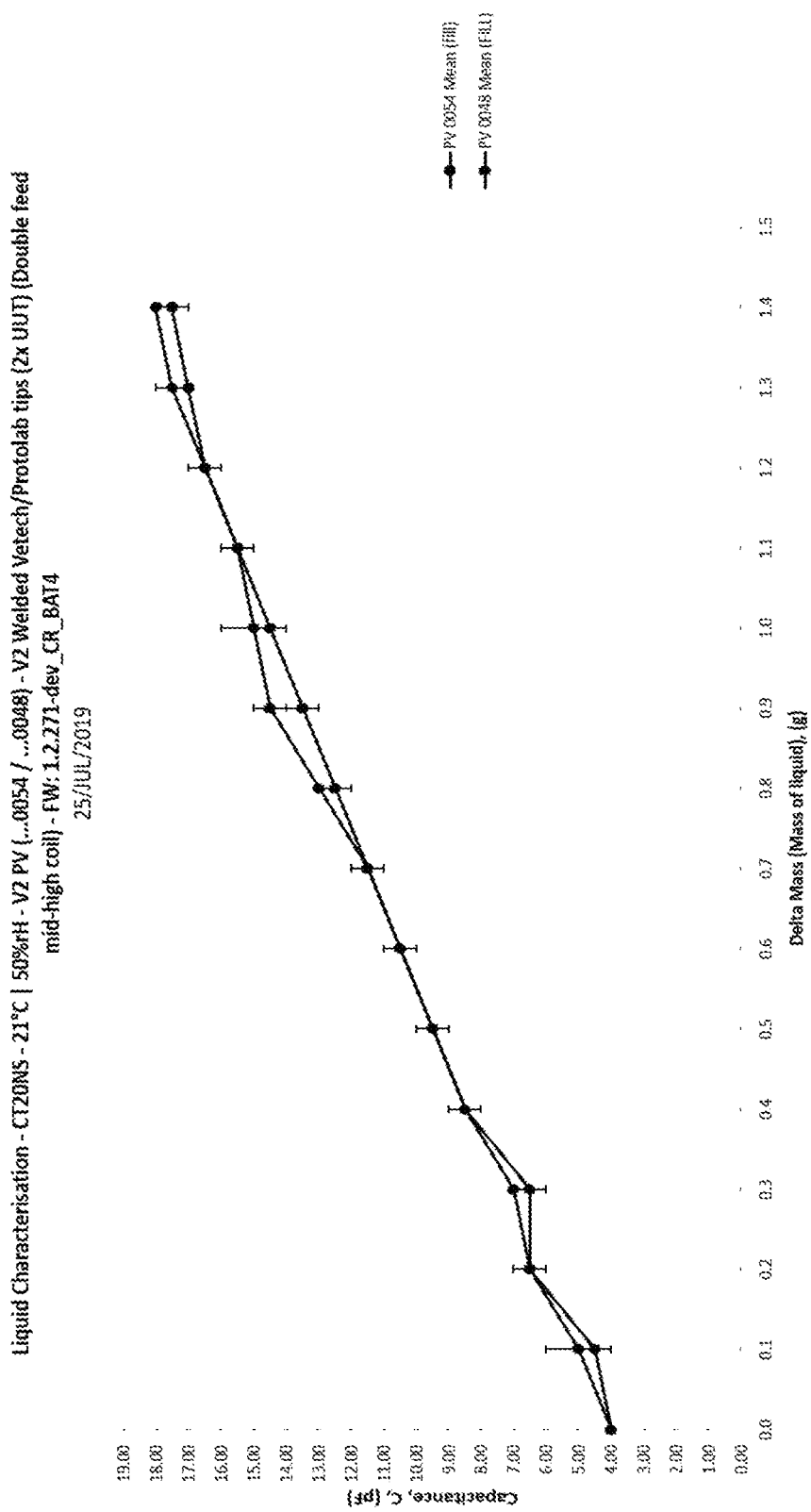
FIG. 33 is a graph showing measurements of capacitance against liquid mass achieved by the liquid level sensing system.

FIG. 33 shows test results plotting liquid mass verses sensor capacitance for two different samples of the measurement circuit system, but the same liquid. The error bars across samples are also shown. Although adequate linearity and absolute accuracy are shown these readings can be further improved with calibration steps added. But it illustrates the fundamental ability to detect with sufficient accuracy whether the liquid mass in the small liquid reservoir is above or below a threshold and to keep the pump off, or turn the pump on, respectively.

Temperature Compensation

The capacitance readings are not only dependent on the volume of the liquid in the reservoir that contains the capacitance plates, but are usually also dependent on the formulation of liquid. They may also be slightly dependent on the temperature of the liquid. To compensate for this temperature shift in the threshold that triggers the pump to remain off or turn on, there is a temperature sensor located close to the vaporiser tip which measures the ambient temperature. This is used by the microprocessor to compensate for the effect of temperature on the threshold values. These thresholds values are characterised at 5° C. and 45° C. and stored on the serial ROM on the 10 mL bottle or capsule. The microprocessor also prohibits filling of the vaporiser if the ambient temperature is outside this range.

Figure 34:
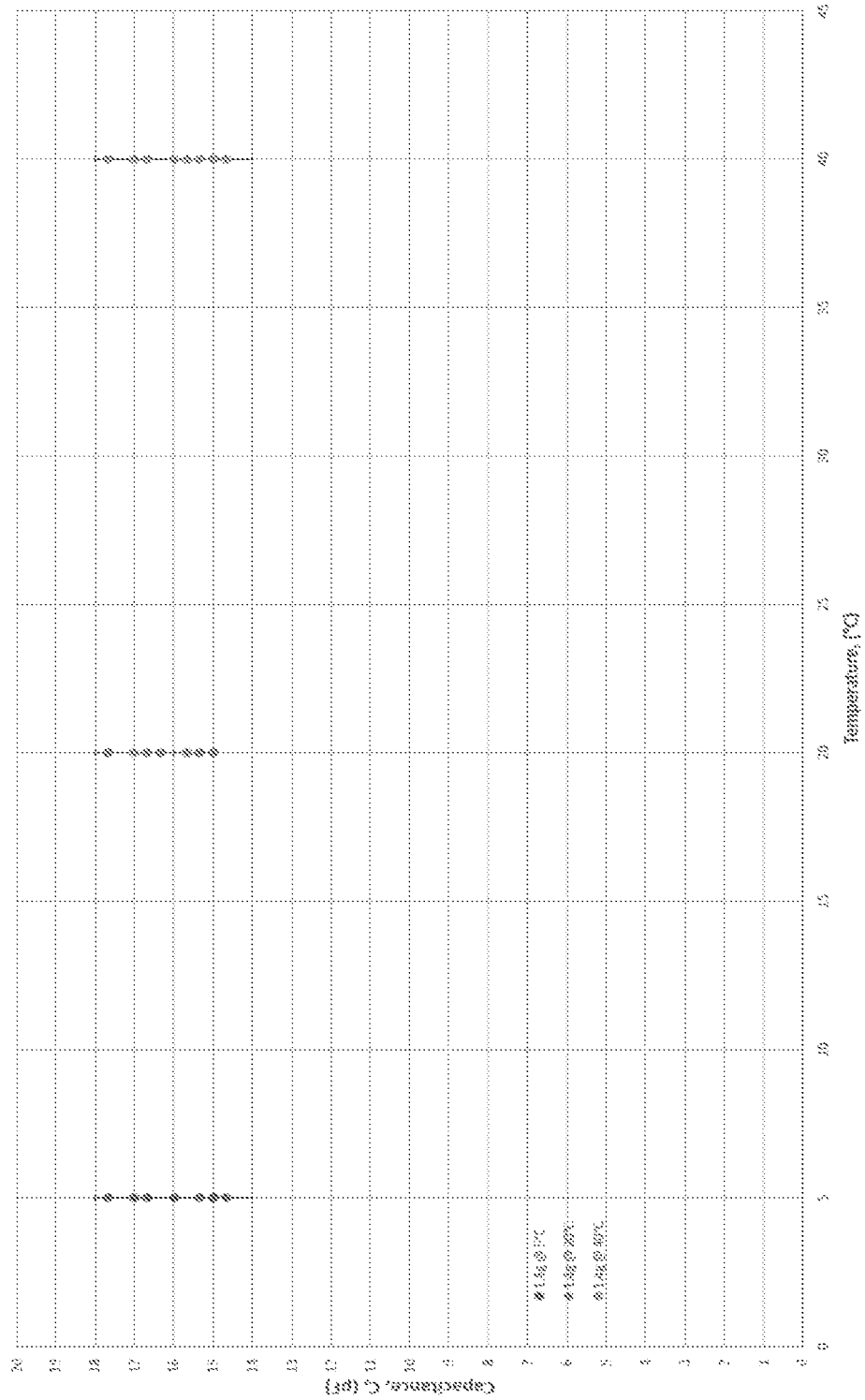
FIG. 34 is a graph showing measurements of capacitance against temperature achieved by the liquid level sensing system.

FIG. 34 shows the raw capacitance readings overlaid with the ambient temperature over time as the vaporiser is first heated to 45° C. and then cooled to 5° C. using the actual AYR capacitance-based liquid level measuring system. Readings were taken for seven tips (each circle on the plot is associated with a single device) at 5° C. and 20° C., and for eight tips at 40° C. Each tip includes 1.4 g of liquid. As can be seen, there is very little change in the range of measured capacitance as a function of temperature, and hence for the specific system used in AYR, as shown in FIG. 31, there is no requirement to compensate for purely temperature dependent capacitance changes.

Flavour Change

The peristaltic pump is bi-directional so when a liquid flavour change is required the microcontroller can reverse pump e-liquid out of the vaporiser tip and back into the main reservoir or re-fill bottle. This will not completely empty the vaporiser of all e-liquid as some will remain soaked into the heating coil but will help to reduce cross flavour contamination.

We can summarise and generalise the key features as follows:

Liquid Level Sensing

A vaping system including:

(a) an automatically re-fillable liquid reservoir that provides liquid to an atomizer;

(b) a liquid level sensing sub-system that directly or indirectly measures, infers or detects the amount of the liquid, or the level of liquid, in the liquid reservoir, by measuring electrical characteristics of the liquid reservoir that vary depending on the amount or level of liquid in the liquid reservoir; and (c) a fluid transfer system configured to automatically transfer liquid to the liquid reservoir under the control of the liquid level sensing sub-system.

Some optional features:

Electrical Characteristics Features

The electrical characteristics measured by the liquid level sensing sub-system are capacitance, or a variable, such as resonant frequency, that corresponds to capacitance.

The liquid level sensing sub-system is a capacitive sensing system that measures the capacitance using two capacitive sensors in the liquid reservoir, and that capacitance varies, approximately, in inverse proportion to the amount or level of the liquid in the reservoir.

The liquid level sensing sub-system detects the resonant frequency of an LC resonator circuit that includes capacitance sensors in the liquid reservoir, and converts this measured resonant frequency to a digital value that corresponds to capacitance, which in turn corresponds to the liquid level in the liquid reservoir a shift in the measured resonant frequency corresponds to a change in capacitance, which in turn corresponds to a change in the liquid level in the liquid reservoir.

The liquid level sensing sub-system is individually calibrated during manufacture or build time using calibration parameters that compensate for stray capacitance, and these are stored in memory in the vaping system that includes that calibrated liquid level sensing sub-system.

The liquid level sensing sub-system is connected to a sensor in or associated with the liquid reservoir and that is excited with an AC signal and capacitance is then measured using a parallel resonance circuit, that capacitance varying with the level of liquid in the liquid reservoir.

The electrical characteristics measured by the liquid level sensing sub-system include one or more of: impedance, reactance, or resistance, or a digital value that corresponds to impedance, reactance, or resistance.

The liquid level sensing sub-system is connected to a sensor in or associated with the liquid reservoir and that is excited with an AC signal and impedance is then measured using a bridge circuit, that impedance varying with the level of liquid in the liquid reservoir.

The liquid level sensing sub-system is connected to a sensor in or associated with the liquid reservoir and that is excited with an AC signal at a frequency that is sufficiently high, such as a 100 KHz signal, that capacitive reactance is the dominant component of the impedance of the liquid reservoir, reducing the significance of resistance (which is more susceptible to changes of orientation of the device); and the impedance is then measured using a bridge circuit, that impedance varying with the level of liquid in the liquid reservoir.

The liquid level sensing sub-system is connected to a sensor in or associated with the liquid reservoir and that is excited with an AC excitation signal, such as a 100 KHz signal, and the impedance is approximately proportional to the attenuation of the excitation signal.

Liquid Level Sensing Sub-System Features the liquid level sensing sub-system provide closed loop control of the fluid transfer system, which is configured to pump liquid into the reservoir until a predefined electrical characteristic threshold is reached.

predefined electrical characteristic threshold corresponds to the liquid reservoir being filled until approximately half full Liquid reservoir total capacity is approximately 2 ml predefined electrical characteristic threshold corresponds to there being approximately 1 ml of liquid in the reservoir the liquid level sensing sub-system compares the measured electrical characteristics to one or more stored values of those electrical characteristics, and controls the fluid transfer system depending on the result of that comparison.

the fluid transfer system is configured to pump liquid into the liquid reservoir, under the control of the liquid level sensing sub-system, until a pre-set electrical characteristic threshold is measured.

The liquid level sensing sub-system turns the pump on if the measured electrical characteristic falls below a predefined level and turns the pump off if the measured electrical characteristic reaches that same predefined level.

The liquid level sensing sub-system turns the pump on if the measured electrical characteristic exceeds a predefined level and turns the pump off if the measured electrical characteristic falls below approximately that same predefined level.

The liquid level sensing sub-system turns the pump on if the amount of liquid, or the level of the liquid, in the liquid reservoir is below a predefined level.

The liquid level sensing sub-system turns the pump off if the amount of liquid, or the level of the liquid, in the liquid reservoir reaches a predefined level.

The liquid level sensing sub-system turns the pump on if the amount of liquid, or the level of the liquid, in the liquid reservoir is below a predefined level and turns the pump off if the amount of liquid, or the level of the liquid, in the liquid reservoir reaches approximately that same predefined level.

The liquid level sensing sub-system measures the orientation of the reservoir or receives an input from a sub-system that measures the orientation of the reservoir, and permits measuring of the electrical characteristics, and/or re-filling, only where the orientation is within a pre-set range.

The liquid level sensing sub-system measures the orientation of the reservoir or receives an input from a sub-system that measures the orientation of the reservoir, and permits measuring of the electrical characteristics, and/or re-filling, only where the orientation is substantially vertical.

The liquid level sensing sub-system measures the orientation of the reservoir or receives an input from a sub-system that measures the orientation of the reservoir, using an ASIC that includes the measuring circuitry for the liquid level sensing sub-system.

Atomiser Features

The liquid reservoir forms part of a re-fillable tip, the entire re-fillable tip being replaceable by an end-user when it reaches the end of its life.

An atomizer with a porous wick, ceramic or other porous material is directly fed liquid from the liquid reservoir, there being no intermediary reservoirs or liquid conduits.

An atomizer with a porous wick, ceramic or other porous material is indirectly fed liquid from the liquid reservoir, via an intermediary reservoir or one or more liquid conduits, such as liquid syphons.

the liquid level sensing sub-system is operable to be used in any of the following types of vaping systems: a portable vaping device; a re-fill and re-charge case that both re-fills with liquid and re-charges a vaping device stored in the case; a docking station that both re-fills with liquid and re-charges a vaping device placed in the docking station; a one piece vaping device with a battery of at least 1000 mAh.

The vaping device uses a ceramic wick.

The vaping device uses a planar ceramic wick with a substantially flat surface with heating elements formed or positioned on that surface.

The vaping device uses a micro-engineered stainless-steel blade.

The fluid transfer system withdraws liquid from a user-replaceable, fully recyclable, closed refill capsule or bottle and pumps it to the liquid reservoir.

The fluid transfer system includes an electrical peristaltic pump.

Sensor Construction Features

The liquid level sensing sub-system is connected to a sensor that includes sensor plates or structures that are placed inside the liquid reservoir.

The liquid level sensing sub-system comprises two opposing capacitive sensor plates or other structures that each include a pair of substantially flat side sections and a central circular or curved section, the flat sections of opposing plates or other structures being substantially parallel to each other.

The central circular or curved section fits around a tube into which an atomizer is fitted.

The opposing plates or other structures sit inside the liquid reservoir.

liquid level sensing sub-system comprises the liquid level sensing sub-system comprises sensor plates or other structures mounted against one or more ribs or other physical features that are configured to ensure consistent and accurate separation of the opposing plates or other structures.

liquid level sensing sub-system comprises capacitive sensor plates or other structures mounted externally to the liquid reservoir and instead positioned in a re-filling dock.

liquid level sensing sub-system comprises two opposing capacitive sensor plates or other structures that each include a substantially flat side section, being substantially parallel to each other and are mounted externally to the liquid reservoir and instead positioned in a re-filling dock.

The liquid level sensing sub-system is connected to a sensor, in or associated with the liquid reservoir, that includes a pair of sensor plates or other structures that include substantially concentric sections.

The liquid level sensing sub-system is connected to a sensor, in or associated with the liquid reservoir, that includes a pair of sensor plates or other structures made of the same metallic material, such as stainless steel or brass.

The electrical characteristics measured by the liquid level sensing sub-system are detected by sensors that are at least in part integral with the walls of the liquid reservoir.

The capacitive sensors form at least part of the inner and outer walls of the liquid reservoir.

the outer walls of the liquid reservoir are part of the outer casing of the vaping device.

The atomizer includes a metal blade or plate and this blade or plate forms a part of one or more of the capacitive sensor plates or other structures.

Liquid Specific Features liquid level sensing sub-system compensates for or adjusts for the chemical composition or formulation of each specific flavor, strength or type of liquid.

each specific flavor, strength or type of liquid is tested and electrical characteristics of each specific liquid as a function of mass or weight of liquid in the liquid reservoir is determined and related data values are stored in a manner accessible to the liquid level sensing sub-system.

The electrical characteristics measured by the liquid level sensing sub-system are dependent on the chemical composition of the liquid in the liquid reservoir and data values specific to liquid of a specific composition, formulation or liquid type are stored on a liquid refill bottle in a memory such as a ROM or optical bar code, for that liquid and are accessible to the liquid level sensing sub-system.

Data values mapping the capacitance, or data related to capacitance, that is measured by the liquid level sensing sub-system at a threshold fill amount, for a specific liquid, is stored in the refill bottle for that specific liquid and is accessible to the to the liquid level sensing sub-system.

Data values mapping the amount or mass of a specific liquid against the capacitance, or data related to capacitance, measured by the liquid level sensing sub-system at one or more thresholds or values relating to the amount of liquid in the liquid reservoir, for that specific liquid, is stored and accessible by the vaping system.

The data values are stored on the bottle or capsule supplying the e-liquid.

The data values are stored in a serial ROM chip on the bottle or capsule.

The data values are stored in a barcode or other optically readable data.

Temperature Dependency Features liquid level sensing sub-system compensates for or adjusts for the temperature of the liquid using an ambient temperature sensor liquid level sensing sub-system prohibits filling operations if the measured temperature, measured using an ambient temperature sensor, falls outside of the pre-set operational limits, such as 5° C. and 45° C.

The data sent to the liquid level sensing sub-system enables the liquid level sensing sub-system to compensate for temperature dependent variability in characteristics of liquids with different chemical compositions.

The electrical characteristics measured by the liquid level sensing sub-system are temperature dependent and the stored values of the electrical characteristics include values at and/or between the lower and upper operating ranges of the device, such as 5° C. and 45° C.

The vaping system includes an ambient temperature sensor that provides temperature data to the liquid filling sub-system so that the sub-system can compare measured electrical characteristics with values that are appropriate for the ambient temperature of the atomizer reservoir.

The vaping system includes a temperature sensor positioned adjacent to or sufficiently close to the liquid reservoir to provide an estimation of the measure the temperature of the liquid in the reservoir.

Data vales characterising how the capacitance of a specific e-liquid or a family or type of liquids varies with temperature is stored and accessible by the vaping system.

Data values characterising how the capacitance of a specific e-liquid or a family or type of e-liquids varies between a lower temperature limit and an upper temperature limit is stored and accessible by the liquid filling sub-system.

The stored data values of the electrical characteristics are stored in or on a liquid capsule that provides liquid to the fluid transfer system.

The stored values of the electrical characteristics are stored in a ROM chip or other memory on the liquid capsule or bottle.

The pre-stored values of the electrical characteristics are stored in an optically readable barcode on the liquid capsule or bottle.

Another aspect is a method of controlling the operation of a liquid transfer sub-system that is part of a vaping system, comprising the step of measuring data that relates to electrical characteristics of a liquid reservoir in the vaping system using a liquid level sensing sub-system, the electrical characteristics varying depending on the amount or level of liquid in the liquid reservoir, and automatically controlling a fluid transfer system in dependence on that measured data.

Capsule with Liquid Type Data

As explained above, the liquid level sensing system detects changes in the electrical characteristics of the liquid reservoir that vary depending on how full the reservoir is with liquid. These electrical characteristics may also vary depending on parameters such as the type of liquid, its nicotine strength, whether it is a nicotine salt or not, whether it includes CBD or THC, its water content, its PV/VG content, and the flavours used. Data defining or relating to these chemical compositions, formulations or liquid types (more generally, 'liquid parameters') has therefore to be available to the liquid level sensing system if it is to operate accurately and reliably across different liquid compositions, formulations or liquid types. For the AYR system, we have tested each possible liquid composition, formulation or liquid and characterised each in terms of the mass or weight of liquid vs capacitance reading. These constants, for a specific liquid composition, formulation or liquid type, are then stored on the refill bottle that contains that specific composition, formulation or liquid type. The data is stored in a machine readable form, typically on a small, low cost ROM chip.

We can generalise as follows:

A capsule, bottle or other form of container configured for engaging with a fluid transfer system that automatically re-fills a liquid reservoir in a vaping device with liquid stored in the container;

the container including, or programmed with, machine readable data that relates to or is associated with the electrical characteristics of the liquid reservoir when including liquid of the chemical composition, formulation or type in the container, those electrical characteristics being relevant to the operation of a liquid level sensing sub-system that controls the fluid transfer system in dependence on measurements of the electrical characteristics, or data related to those electrical characteristics.

Some optional features:

The container includes a memory, such as a ROM chip or FLASH memory, which stores or encodes electrical characteristics, or data related to electrical characteristics, of the specific liquid stored in that capsule.

The container includes an optically machine-readable code, such as a barcode, which encodes electrical characteristics, or data related to those electrical characteristics, of the specific liquid stored in that capsule.

The liquid level sensing sub-system reads pre-stored value(s) of the electrical characteristics of or associated with the liquid reservoir in the vaping device, such as capacitance or impedance, that indicate that the liquid reservoir is sufficiently full of liquid and the liquid level sensing sub-system compares that pre-stored value(s) with the measured electrical characteristics, to determine if the fluid transfer system should be turned on or off.

The electrical characteristics are dependent on the chemical composition of the liquid and the pre-stored values are specific to liquid of a specific type, kind or flavor.

The electrical characteristics are temperature dependent and the pre-stored values of the electrical characteristics include values at the lower and upper operating ranges of the device, such as 5° C. and 45° C.

liquid level sensing sub-system compensates for or adjusts for the chemical composition or formulation of each specific flavor, strength or type of liquid each specific flavor, strength or type of liquid is tested and electrical characteristics of each specific liquid as a function of mass or weight of liquid in the liquid reservoir is determined and stored in a manner accessible to the liquid level sensing sub-system The electrical characteristics measured by the liquid level sensing sub-system are dependent on the chemical composition of the liquid in the liquid reservoir and values specific to liquid of a specific composition, formulation or liquid type are stored on a liquid refill bottle in a memory such as a ROM or optical bar code, for that liquid and are accessible to the liquid level sensing sub-system.

Data mapping the capacitance, or data related to capacitance, that is measured by the liquid level sensing sub-system at a threshold fill amount, for a specific liquid, is stored in the refill bottle for that specific liquid and is accessible to the to the liquid level sensing sub-system.

Data mapping the amount or mass of a specific liquid against the capacitance, or data related to capacitance, measured by the liquid level sensing sub-system at one or more thresholds or values relating to the amount of liquid in the liquid reservoir, for that specific liquid, is stored and accessible by the vaping system.

The data is stored on the bottle or capsule supplying the e-liquid.

The data is stored in a serial ROM chip on the bottle or capsule.

The data is stored in a barcode or other optically readable data.

The electrical characteristics include temperature dependent electrical characteristics that enable a liquid level sub-system to compensate for variations in the ambient temperature of the atomiser reservoir.

temperature dependent electrical characteristics are the signal associated with a maximum level or amount of liquid in an atomizer reservoir at the upper and lower limits of the operating temperature of the device the container is providing liquid to.

temperature dependent electrical characteristics are used by a liquid level sensing sub-system that measures, detects or infers the level of liquid in the liquid reservoir.

a temperature sensor measures the temperature in the device and the liquid level sensing sub-system is locked from operation if the device temperature, or a temperature related to the device temperature, is higher than a high temperature threshold, or is lower than a low temperature threshold.

The invention claimed is:

1. A vaping system including:
   (a) a re-fillable liquid reservoir that provides liquid to an atomizer;
   (b) a liquid level sensing sub-system that directly or indirectly measures, infers or detects the amount of the liquid, or the level of liquid, in the liquid reservoir, by measuring electrical characteristics of the liquid reservoir that vary depending on the amount or level of liquid in the liquid reservoir; and
   (c) a fluid transfer system configured to automatically transfer liquid to the liquid reservoir under the control of the liquid level sensing sub-system, wherein the electrical characteristics measured by the liquid level sensing sub-system are capacitance, or a variable, such as resonant frequency, that corresponds to capacitance.

2. The vaping system of claim 1 in which the liquid level sensing sub-system detects the resonant frequency of an LC resonator circuit that includes capacitance sensors in the liquid reservoir, and converts this measured resonant frequency to a digital value that corresponds to capacitance, which in turn corresponds to the liquid level in the liquid reservoir; and a shift in the measured resonant frequency corresponds to a change in capacitance, which in turn corresponds to a change in the liquid level in the liquid reservoir.

3. The vaping system of claim 1 in which the liquid level sensing sub-system is individually calibrated during manufacture or build time using calibration parameters that compensate for stray capacitance, and these are stored in memory in the vaping system that includes that calibrated liquid level sensing sub-system.

4. The vaping system of claim 1 in which the electrical characteristics measured by the liquid level sensing sub-system include one or more of: impedance, reactance, or resistance, or a digital value that corresponds to impedance, reactance, or resistance.

5. The vaping system of claim 4 in which the liquid level sensing sub-system is connected to a sensor in or associated with the liquid reservoir and that is excited with an AC signal and (a) impedance is measured using a bridge circuit, that impedance varying with the level of liquid in the liquid reservoir, or (b) capacitance is measured using a parallel resonance circuit, that capacitance varying with the level of liquid in the liquid reservoir.

6. The vaping system of claim 4 in which the liquid level sensing sub-system is connected to a sensor in or associated with the liquid reservoir and that is excited with an AC signal at a frequency that is sufficiently high, such as a 100 KHz signal, that capacitive reactance is the dominant component of the impedance of the liquid reservoir, reducing the significance of resistance (which is more susceptible to changes of orientation of the device); and the impedance is then measured using a bridge circuit, that impedance varying with the level of liquid in the liquid reservoir and being approximately proportional to the attenuation of the excitation signal.

7. The vaping system of claim 1 in which the liquid level sensing sub-system provide closed loop control of the fluid transfer system, which is configured to pump liquid into the reservoir until a predefined electrical characteristic threshold is reached.

8. The vaping system of claim 7 in which the predefined electrical characteristic corresponds to the liquid reservoir being filled until approximately half full such as, if the liquid reservoir total capacity is approximately 2 ml and the predefined electrical characteristic threshold corresponds to approximately 1 ml of liquid being in the liquid reservoir.

9. The vaping system of claim 1 in which the liquid level sensing sub-system compares measured electrical characteristics to one or more stored values of those electrical characteristics, and controls the fluid transfer system depending on the result of that comparison and in which the fluid transfer system is configured to pump liquid into the liquid reservoir, under the control of the liquid level sensing sub-system, until a pre-set electrical characteristic threshold is measured.

10. The vaping system of claim 1 in which the liquid level sensing sub-system turns the fluid transfer system on if the measured electrical characteristic falls below a predefined level and turns the fluid transfer system off if the measured electrical characteristic reaches that same predefined level; or the liquid level sensing sub-system turns the fluid transfer system on if the measured electrical characteristic exceeds a predefined level and turns the fluid transfer system off if the measured electrical characteristic falls below approximately that same predefined level.

11. The vaping system of claim 1 in which the liquid level sensing sub-system turns the fluid transfer system on if the amount of liquid, or the level of the liquid, in the liquid reservoir is below a predefined level and the liquid level sensing sub-system turns the fluid transfer system off if the amount of liquid, or the level of the liquid, in the liquid reservoir reaches the, or a, predefined level.

12. The vaping system of claim 1 in which the liquid level sensing sub-system measures the orientation of the reservoir, or receives an input from an sub-system that measures the orientation of the reservoir, and permits measuring of the electrical characteristics, and/or re-filling, only where the orientation is within a pre-set range, such as being substantially upright or vertical.

13. The vaping system of claim 1 in which the liquid reservoir forms part of a re-fillable tip, and the entire re-fillable tip is replaceable by an end-user when it reaches the end of its life.

14. The vaping system of claim 1 in which the liquid level sensing sub-system is operable to be used in any of the following types of vaping systems: a portable vaping device; a re-fill and re-charge case that both re-fills with liquid and re-charges a vaping device stored in the case; a docking station that both re-fills with liquid and re-charges a vaping device placed in the docking station; a one piece vaping device with a battery of at least 1000 mAh.

15. The vaping system of claim 1 in which atomiser uses a ceramic wick, or a planar ceramic wick with a substantially flat surface with heating elements formed or positioned on that surface, or a coil-less micro-engineered stainless steel blade.

16. The vaping system of claim 1 in which the fluid transfer system withdraws liquid from a user-replaceable, fully recyclable, closed refill capsule or bottle and pumps it to the liquid reservoir.

17. The vaping system of claim 1 in which the liquid level sensing sub-system is connected to a sensor that includes sensor plates or structures that are placed inside the liquid reservoir.

18. The vaping system of claim 1 in which the liquid level sensing sub-system comprises two opposing capacitive sensor plates or other structures that each include a pair of substantially flat side sections and a central circular or curved section, the flat sections of opposing plates or other structures being substantially parallel to each other.

19. The vaping system of claim 1 in which the liquid level sensing sub-system comprises sensor plates or other structures mounted against one or more ribs or other physical features that are configured to ensure consistent and accurate separation of the sensor plates or other structures.

20. The vaping system of claim 1 in which the electrical characteristics measured by the liquid level sensing sub-system are detected by sensors that are, at least in part, integral with the walls of the liquid reservoir.

21. The vaping system of claim 1 in which the atomizer includes a metal blade or plate and this blade or plate forms a part of the capacitive sensor plates or other structures.

22. The vaping system of claim 1 in which the liquid level sensing sub-system comprises capacitive sensor plates or other structures mounted externally to the liquid reservoir, such as being positioned in a re-filling dock or re-fill case.

23. The vaping system of claim 1 in which the liquid level sensing sub-system compensates for or adjusts for the chemical composition or formulation of each specific flavor, strength or type of liquid; and in which each specific flavour, strength or type of liquid is tested and electrical characteristics of each specific liquid as a function of mass or weight or liquid in the liquid reservoir is determined and related data values stored in a manner accessible to the liquid level sensing sub-system.

24. The vaping system of claim 1 in which the electrical characteristics measured by the liquid level sensing sub-system are dependent on the chemical composition of the liquid in the liquid reservoir and data values specific to liquid of a specific composition, formulation or liquid type are stored on a liquid refill bottle in a memory such as a ROM or optical bar code, for that liquid and are accessible to the liquid level sensing sub-system.

25. The vaping system of claim 1 in which data values mapping the capacitance, or data related to capacitance, that is measured by the liquid level sensing sub-system at a threshold fill amount, for a specific liquid, is stored in a refill bottle for that specific liquid and is accessible to the to the liquid level sensing sub-system from a chip, barcode or other optically readable data on the bottle.

26. The vaping system of claim 1 in which data values mapping the amount or mass of a specific liquid against the capacitance, or data related to capacitance, measured by the liquid level sensing sub-system at one or more thresholds or values relating to the amount of liquid in the liquid reservoir, for that specific liquid, is stored and accessible by the vaping system.

27. The vaping system of claim 1 in which the liquid level sensing sub-system compensates for or adjusts for the temperature of the liquid using an ambient temperature sensor and in which data sent to the liquid level sensing sub-system enables the liquid level sensing sub-system to compensate for temperature dependent variability in characteristics of liquids with different chemical compositions.

28. The vaping system of claim 1 in which the liquid level sensing sub-system prohibits filling operations if the measured temperature, measured using an ambient temperature sensor, falls outside of pre-set operational limits, such as 5° C. and 45° C.

29. The vaping system of claim 1 which includes a temperature sensor positioned adjacent to or sufficiently close to the liquid reservoir to provide an estimation of the measure the temperature of the liquid in the reservoir.

30. The vaping system of claim 1 in which data characterising how the capacitance of a specific e-liquid or a family or type of e-liquids varies with temperature is stored and accessible by the vaping system on a chip, barcode or other optically readable data on a user-replaceable, closed and not user-refillable liquid capsule or bottle that provides liquid to the fluid transfer system.

31. The vaping system of claim 1 including a handheld vaping device configured work with;
（a) a non-user refillable combined atomizer and liquid reservoir that is (i) attachable to, and removable from, a main body of the device and that is (ii) supplied to an end-user pre-filled with liquid; and to also work with:
(b) a user refillable combined atomizer and liquid reservoir that is (i) attachable to, and removable from, the main body of the device and that is (ii) configured to be automatically fillable with liquid multiple times using the fluid transfer system.

32. The vaping system of claim 1 that includes (i) a re-fillable tip or pod and (ii) a pre-filled, non-re-fillable tip or pod, that are each configured to fit in, or attach to, two or more of the following vaping devices:
(a) a portable vaping device body with no integral fluid transfer system;
(b) a portable vaping device body configured to engage with a liquid refilling dock that includes the fluid transfer system;
(c) a portable vaping device body configured to engage with a portable case that includes the fluid transfer system; and
(d) a portable vaping device body with an integral fluid transfer system.

33. The vaping system of claim 1 comprising a vaporising device that includes (i) a liquid reservoir supplying liquid to an atomizer; (ii) a port, aperture or nozzle configured to enable the device to be filled with atomisable liquid from a liquid source and (iii) a liquid path connecting the liquid reservoir to the port, aperture or nozzle; and in which the liquid path includes a channel covered with a plastics film.

34. The vaping system of claim 1 comprising a liquid re-filling bottle configured to engage with a fluid transfer system in a vaping system, the bottle including a section or recess into which an authentication chip or other authentication memory component can be physically inserted and then retained by the shape of the section or recess until physically removed to enable the bottle to be re-cycled.

35. The vaping system of claim 1 comprising an atomiser pod pre-filled with an atomisable liquid, and a vaping device main body, in which the pod includes an authentication chip or memory and the vaping device body includes a pod authentication sub-system that enables a pod to be used with that body only if certain pod criteria are met;
and the vaping device body further includes a wireless connectivity sub-system that (i) exchanges data with an application or browser running on a user's smartphone, the application or browser connecting to a web server based age verification and pod usage system and (ii) is configured to unlock the body to enable normal vaping use only if that user passes the age requirements of the age verification system and the pod is authorised for use.

36. The vaping system of claim 1 comprising a liquid re-fill bottle or container and a liquid transfer system configured to automatically transfer liquid from the bottle or container to a liquid reservoir in a vaping device; in which the container includes a counter in a memory chip that is configured to change its value when a defined type of event affects the bottle or container, so that when the counter reaches a limit, such as zero, or another value, the bottle or container is locked from further use.

37. The vaping system of claim 1 comprising a vaping system including a pre-filled pod configured for a vaping device, the pod including a counter in a memory chip that is configured to change its value when a defined type of event affects the pod, so that when the counter reaches a limit, such as zero or another value, the pod is locked from further use.

38. The vaping system of claim 1 comprising a liquid atomising system with a heating element configured to heat an atomisable liquid and to produce a vapour, atomisation or mist, and that is controlled with a constant temperature driver, the driver directly or indirectly measuring the current through a heating element using a power source with a known voltage and enabling a microcontroller or processor to (a) calculate or determine the resistance of the heating element and to (b) calculate, from stored data for the temperature coefficient of resistance of the material the heating element is made from, or (c) look up the temperature of the heating element;

and in which the driver is configured to use a closed loop temperature control algorithm to regulate the power, current or voltage to stabilize the temperature of the heating element at a pre-set level or range by adjusting the power duty ratio.

39. The vaping system of claim 1 comprising a liquid re-filling device that stores a vaping device and enables the vaping device to be ejected or withdrawn, and the re-filling device and/or vaping device includes a switch that is (a) activated as the vaping device starts to be ejected or withdrawn from the re-filling device and that (b) sends a signal to ensure that any data communications between the vaping device and the re-filling device are terminated in a controlled manner before a data connection is lost.

40. The vaping system of claim 1 comprising a vaping device that includes a series of lights that progressively extinguish as the user vapes, but can also be controlled to illuminate together or in a sequential sequence or otherwise to form a light pattern.

41. The vaping system of claim 1 configured to enable a vaping device to be used for a single session, a session being a limited time or limited extent of vaping during which the vaping device is operable and for which the vaping device provides a start and end visual, haptic and/or sonic marker;

and in which the system is configured to receive from a user a selection or indication of the type or brand of cigarette they currently smoke, and the system then automatically adjusts the time or other parameters of the single session so that the amount of nicotine generated by the vaping device, or inhaled by a user, during that session is approximately equivalent to the amount of nicotine associated with smoking a single cigarette of that specific type or brand of cigarette.

42. The vaping system of claim 1 further comprising: (i) a vaping device including a rechargeable battery and a data port; and (ii) a first charging system for that vaping device and that is configured to provide power to the rechargeable battery; and (iii) a separate, second charging system that is configured to receive the vaping device and to provide power to the rechargeable battery and to receive data from the vaping device via the data port; and (iv) a mobile website configured to be hosted on a remote server and to be accessible from an end-user's smartphone, smartwatch or other personal device; and in which the second charging system includes a Wi-Fi module, chip or unit configured to send the data received from the vaping device, to the mobile website hosted on the remote server over the internet.

43. The vaping system of claim 1 including a portable vaping device system comprising:
(i) a portable vaping device including a rechargeable battery and a data port; and
(ii) a mobile website configured to be hosted on a remote server and to be accessible from an end-user's smartphone, smartwatch or other personal device by selecting an icon that opens a weblink to the website and not a local vaping-specific application running on the device; and in which
the vaping device includes a Wi-Fi module, chip or unit configured to send data to the mobile website hosted on the remote server over the internet.

44. The vaping system of claim 1 comprising a portable vaping device including a UWB chip or ASIC integrating UWB functionality to provide geo-location and/or geo-fencing capability to prevent the operation of the portable vaping devices in defined areas.

45. The vaping system of claim 1 comprising a vaping data analysis system including a vaping system and a remote server, in which the vaping system collects usage data relating to how the device is being used by a consumer and sends that usage data directly or indirectly to a remote server using Wi-Fi connectivity to the internet; the Wi-Fi connectivity being established by the vaping device, and the server analyses the data and generates consumer or behavioural data insights based on the usage data.

* * * * *